US006348577B1

(12) United States Patent
Okado et al.

(10) Patent No.: US 6,348,577 B1
(45) Date of Patent: Feb. 19, 2002

(54) REGULATION OF AUREOBASIDIN SENSITIVITY IN FUNGUS

(75) Inventors: Takashi Okado, Kyoto-fu; Kazutoh Takesako, Shiga-ken; Ikunoshin Kato, Kyoto-fu, all of (JP)

(73) Assignee: Takara Shuzo Co., Ltd., Kyoto-fu (JP)

( * ) Notice: Subject to any disclaimer, the term of this patent is extended or adjusted under 35 U.S.C. 154(b) by 0 days.

(21) Appl. No.: 09/414,006

(22) Filed: Oct. 7, 1999

Related U.S. Application Data

(60) Division of application No. 08/492,459, filed on Jun. 29, 1995, now Pat. No. 6,015,689, which is a continuation-in-part of application No. 08/243,403, filed on May 16, 1994, now abandoned.

(30) Foreign Application Priority Data

| May 24, 1993 | (JP) | ............................................. 5-142523 |
| Dec. 28, 1993 | (JP) | ............................................. 5-348893 |
| Jun. 29, 1994 | (JP) | ............................................. 6-168611 |
| Mar. 30, 1995 | (JP) | ................................................ 7-95831 |
| Mar. 30, 1995 | (JP) | ................................................ 7-95955 |
| May 17, 1995 | (JP) | ............................................. 7-141393 |

(51) Int. Cl.[7] .................... C07K 14/00; C12N 15/00
(52) U.S. Cl. ................. 530/350; 530/371; 530/824; 435/69.1; 435/320.1; 435/440
(58) Field of Search ................. 530/350, 371, 530/824; 435/69.1, 440, 320.1

(56) References Cited

U.S. PATENT DOCUMENTS

| 5,200,505 A | | 4/1993 | Takesako ..................... 530/323 |
| 6,015,689 A | * | 1/2000 | Okado et al. ............... 435/69.1 |
| 6,022,949 A | * | 2/2000 | Okado et al. ................ 530/350 |

FOREIGN PATENT DOCUMENTS

| EP | 0 443 719 | 8/1991 |
| EP | 0 644 262 | 3/1995 |

OTHER PUBLICATIONS

Database GenBank on STN, Boyer et al., Accession No. S37815, May 3, 1994.*
Y. Yoshikawa et al., "Isolation, Structures, and Antifungal Activities of New Aureobasidins", The Journal of Antibiotics, vol. 46, No. 9, pp. 1347–1354, Sep. 1993.
EMBL/GenBank/DDBJ databases (Oct. 5, 1994) Boyer, J. et al. "S. cerevisiae chromosome XI reading frame ORF YKLOO4w" XP00201125.
EMBL/GenBank/DDBJ databanks (Jan. 6, 1994) Boyer, J. et al. "Hypothetical 45.2KD protein RPL14A–MRP17 intergenic region" XP002011027.
Haffter et al., Suppression of carboxy–terminal truncations of the yeast mitochondrial mRNA–specific translational activatory PET 122 by mutations in two new genes, MRP17 and PET127, Mol. Gen. Genet. (1992) 235: pp. 64–73.
Boyer et al. (1994) EMBL/GenBank/DDBJ Database, Accession No. Z28004.
Boyer et al. (1994) EMBL/GenBank/DDBJ Database, Accession No. P36107.
Boyer et al. (1994) EMBL/GenBank/DDBJ Database, Accession No. S37815, S71108.

* cited by examiner

*Primary Examiner*—Christopher S. F. Low
*Assistant Examiner*—Chih-Min Kam
(74) *Attorney, Agent, or Firm*—Wenderoth, Lind & Ponack, L.L.P.

(57) ABSTRACT

The present invention provides a protein regulating the sensitivity of fungus to an antimycotic aureobasidin, a gene coding for this protein, the use thereof, an antibody for the protein and the use thereof. The invention is useful in the diagnosis and treatment for diseases including mycoses. The invention also provides a novel chromosome integration vector capable of imparting a novel selective marker of a drug resistance to a fungal transformant, a transformant transformed with this vector and a process for producing the same. In particular, it provides a protein capable of imparting the resistance to aureobasidin and acting as a selective marker and a DNA coding for the same.

4 Claims, 9 Drawing Sheets

ABOUT 2.4kb

ABOUT 3.5kb

ABOUT 8.5kb

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 2385
      (B) TYPE: nucleic acid
      (C) STRANDEDNESS: double
      (D) TOPOLOGY: linear (ii) MOLECULE TYPE: genomic DNA (xi) SEQUENCE DESCRIPTION: SEQ ID NO:1:

| | | | | | |
|---|---|---|---|---|---|
| AAGCTTTTTT | GCCTCTGCAA | AAGTTCCTTT | CTCGAATTGG | TTTTTTGAGG | AAAAGCAAGT | 60 |
| TAATAAACTA | ATTATATTAT | ATATAATTAG | CAATTTTATA | AAAAAAATAA | AAAAATAGCC | 120 |
| CTGATTGCTG | GCAACTGTGA | GCTGAACATT | GGTTAATCGG | TCCATCTTTT | TTTAAATATT | 180 |
| TTACATCGCT | ACTTTTAAGT | GCTTGACACT | TGCATTTAAT | AGCTACTTTC | TTTCCTTCAT | 240 |
| AAAAATTCCT | TTTTTTTCCT | TTAGTTTTCC | GGTTAATTCC | TTACGAAATT | TTTTTCGTAC | 300 |
| GCTTCCCTTT | TTTACTCTGA | TAATTCTTTG | AAGCAATGTC | TGCTCTTTCG | ACCTTAAAAA | 360 |
| AGCGCCTTGC | TGCGTGTAAC | CGAGCATCCC | AATACAAGTT | GGAAACAAGC | TTAAACCCTA | 420 |
| TGCCTACATT | TCGTTTGCTA | CGCAATACGA | AATGGTCATG | GACACATTTG | CAATATGTGT | 480 |
| TTCTAGCAGG | TAATTTGATT | TTTGCTTGTA | TTGTCATTGA | ATCTCCTGGA | TTCTGGGGGA | 540 |
| AATTTGGCAT | TGCCTGTCTT | TTGGCCATTG | CGTTGACCGT | TCCTTTAACA | CGCCAAATTT | 600 |
| TTTTTCCTGC | CATTGTTATC | ATCACCTGGG | CAATTTTATT | TTACTCTTGT | AGGTTTATTC | 660 |
| CAGAACGCTG | GCGTCCACCC | ATATGGGTTC | GTGTTTTACC | CACACTTGAA | AATATTCTTT | 720 |
| ATGGCTCTAA | TCTTTCTAGT | CTTCTCTCGA | AAACCACGCA | TAGCATCCTT | GATATTTTGG | 780 |
| CCTGGGTTCC | ATATGGAGTC | ATGCATTATT | CGGCTCCTTT | TATCATTTCA | TTTATTCTTT | 840 |
| TCATCTTTGC | ACCTCCTGGA | ACTCTTCCAG | TTTGGGCTCG | AACTTTTGGT | TATATGAATT | 900 |
| TATTTGGTGT | TCTTATCCAA | ATGGCTTTCC | CCTGTTCTCC | TCCTTGGTAT | GAAAATATGT | 960 |
| ATGGTTTAGA | ACCTGCCACG | TATGCAGTAC | GTGGCTCTCC | TGGTGGATTG | GCCCGTATTG | 1020 |
| ATGCTCTCTT | CGGCACTAGC | ATTTACACTG | ATTGTTTTTC | TAACTCTCCG | GTTGTTTTTG | 1080 |
| GTGCCTTTCC | ATCTCTTCAC | GCTGGATGGG | CCATGCTGGA | AGCACTTTTC | CTTTCGCATG | 1140 |
| TGTTTCCTCG | ATACCGCTTC | TGCTTTTATG | GATATGTTCT | ATGGCTTTGC | TGGTGTACTA | 1200 |
| TGTACCTTAC | CCACCACTAC | TTTGTAGATT | TGGTCGGCGG | TATGTGTTTA | GCTATTATAT | 1260 |
| GCTTCGTTTT | TGCTCAAAAG | CTACGCCTCC | CACAGTTGCA | AACTGGTAAA | ATCCTTCGTT | 1320 |
| GGGAATACGA | GTTTGTTATC | CACGGTCATG | GTCTTTCCGA | AAAACCAGC | AACTCCTTGG | 1380 |
| CTCGTACCGG | CAGCCCATAC | TTACTTGGAA | GGGATTCTTT | TACTCAAAAC | CCTAATGCAG | 1440 |
| TAGCCTTCAT | GAGTGGTCTT | AACAATATGG | AACTTGCTAA | CACCGATCAT | GAATGGTCCG | 1500 |
| TGGGTTCATC | ATCACCTGAG | CCGTTACCTA | GTCCTGCTGC | TGATTTGATT | GATCGTCCTG | 1560 |
| CCAGTACCAC | TTCCTCCATC | TTTGATGCAA | GTCATCTTCC | TTAAATCAAC | GTGCTTTAAG | 1620 |
| AATATATTTC | CAAAAGCTAC | ATGATACATT | GACTAGAATC | GGTTTGATTC | ATAGTGGTAT | 1680 |
| TGGAATGATG | TTGTTCATTG | TGTTTTTTAA | CTGTTAATCT | GACATCCATT | GAGTCATTCT | 1740 |
| TTACAATTTG | TAAAATTAAT | TTGTATCACT | AATTTTGAAG | GAAGCTATTT | TGGTATTAAT | 1800 |
| ACCGCTTTTG | GTCTCCACTT | CCTTTTCGAA | ACTCTTAACA | GCGATTAGGC | CGGGTATCTT | 1860 |
| CCAGTGTGAT | GTATAGGTAT | TTGTCGTTTT | TTTATCATTT | CCGTTAATAA | AGAACTCTTT | 1920 |
| TATCCAGCTT | CTTACACTGT | CAACTGTTGT | GAAAGGAACA | CATTTAGAAT | TCATTTTCC | 1980 |
| TTATTTGTTG | TGATTAAAAT | CGTTTGACAT | AATTTTAAAT | TTGGTTTGAA | ATGTGTGTGA | 2040 |
| GAAGGCTTGT | TTTATTCATT | TAGTTTATTG | CTTGTTTGCA | CGAAAATCCA | GAACGGAGCA | 2100 |
| TTAATGTAAT | CCTTTTTTAT | TCTGTAAAGC | GTTTTTATAC | AAATGTTGGT | TATACGTTTC | 2160 |
| TAAAATAAGA | ATATTGTTAT | AATAATATAG | TTTTTTCTAT | CATTTGTTAC | ACACACTAAA | 2220 |
| GAGACATTAA | GGATAAGCAA | ATGTGTTAAA | ATGATAATAT | ATTTTGGAAA | CATTTATAAA | 2280 |

GAAATTAAGC AGCTTTGACT AACTACATTT TGTTTTTTT CCTAAGCAAA ACTGTATAGT    2340

TATACACGCG AGCTGTATTC ACTTCCATTG TAGTGACTTG AGCTC    2385

(2) INFORMATION FOR SEQ ID NO:2:

(i) SEQUENCE CHARACTERISTICS:
        (A) LENGTH:  422
        (B) TYPE:  amino acid
        (C) STRANDEDNESS:  single
        (D) TOPOLOGY:  linear (ii) MOLECULE TYPE: peptide (xi) SEQUENCE DESCRIPTION: SEQ ID NO:2:

```
Met Ser Ala Leu Ser Thr Leu Lys Lys Arg Leu Ala Ala Cys Asn
 1               5                  10                  15

Arg Ala Ser Gln Tyr Lys Leu Glu Thr Ser Leu Asn Pro Met Pro
                20                  25                  30

Thr Phe Arg Leu Leu Arg Asn Thr Lys Trp Ser Trp Thr His Leu
                35                  40                  45

Gln Tyr Val Phe Leu Ala Gly Asn Leu Ile Phe Ala Cys Ile Val
                50                  55                  60

Ile Glu Ser Pro Gly Phe Trp Gly Lys Phe Gly Ile Ala Cys Leu
                65                  70                  75

Leu Ala Ile Ala Leu Thr Val Pro Leu Thr Arg Gln Ile Phe Phe
                80                  85                  90

Pro Ala Ile Val Ile Ile Thr Trp Ala Ile Leu Phe Tyr Ser Cys
                95                 100                 105

Arg Phe Ile Pro Glu Arg Trp Arg Pro Ile Trp Val Arg Val
               110                 115                 120

Leu Pro Thr Leu Glu Asn Ile Leu Tyr Gly Ser Asn Leu Ser Ser
               125                 130                 135

Leu Leu Ser Lys Thr Thr His Ser Ile Leu Asp Ile Leu Ala Trp
               140                 145                 150

Val Pro Tyr Gly Val Met His Tyr Ser Ala Pro Phe Ile Ile Ser
               155                 160                 165

Phe Ile Leu Phe Ile Phe Ala Pro Pro Gly Thr Leu Pro Val Trp
               170                 175                 180

Ala Arg Thr Phe Gly Tyr Met Asn Leu Phe Gly Val Leu Ile Gln
               185                 190                 195

Met Ala Phe Pro Cys Ser Pro Pro Trp Tyr Glu Asn Met Tyr Gly
               200                 205                 210

Leu Glu Pro Ala Thr Tyr Ala Val Arg Gly Ser Pro Gly Gly Leu
               215                 220                 225

Ala Arg Ile Asp Ala Leu Phe Gly Thr Ser Ile Tyr Thr Asp Cys
               230                 235                 240

Phe Ser Asn Ser Pro Val Val Phe Gly Ala Phe Pro Ser Leu His
               245                 250                 255

Ala Gly Trp Ala Met Leu Glu Ala Leu Phe Leu Ser His Val Phe
               260                 265                 270

Pro Arg Tyr Arg Phe Cys Phe Tyr Gly Tyr Val Leu Trp Leu Cys
               275                 280                 285

Trp Cys Thr Met Tyr Leu Thr His His Tyr Phe Val Asp Leu Val
               290                 295                 300

Gly Gly Met Cys Leu Ala Ile Ile Cys Phe Val Phe Ala Gln Lys
```

```
                305                 310                 315
Leu Arg Leu Pro Gln Leu Gln Thr Gly Lys Ile Leu Arg Trp Glu
                320                 325                 330
Tyr Glu Phe Val Ile His Gly His Gly Leu Ser Glu Lys Thr Ser
                335                 340                 345
Asn Ser Leu Ala Arg Thr Gly Ser Pro Tyr Leu Leu Gly Arg Asp
                350                 355                 360
Ser Phe Thr Gln Asn Pro Asn Ala Val Ala Phe Met Ser Gly Leu
                365                 370                 375
Asn Asn Met Glu Leu Ala Asn Thr Asp His Glu Trp Ser Val Gly
                380                 385                 390
Ser Ser Ser Pro Glu Pro Leu Pro Ser Pro Ala Ala Asp Leu Ile
                395                 400                 405
Asp Arg Pro Ala Ser Thr Thr Ser Ser Ile Phe Asp Ala Ser His
                410                 415                 420
Leu Pro (2) INFORMATION FOR SEQ ID NO:3:

(i) SEQUENCE CHARACTERISTICS:
        (A) LENGTH: 2385
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:3:

AAGCTTTTTT GCCTCTGCAA AAGTTCCTTT CTCGAATTGG TTTTTTGAGG AAAAGCAAGT      60

TAATAAACTA ATTATATTAT ATATAATTAG CAATTTTATA AAAAAAATAA AAAAATAGCC     120

CTGATTGCTG GCAACTGTGA GCTGAACATT GGTTAATCGG TCCATCTTTT TTTAAATATT     180

TTACATCGCT ACTTTTAAGT GCTTGACACT TGCATTTAAT AGCTACTTTC TTTCCTTCAT     240

AAAAATTCCT TTTTTTTCCT TTAGTTTTCC GGTTAATTCC TTACGAAATT TTTTTCGTAC     300

GCTTCCCTTT TTTACTCTGA TAATTCTTTG AAGCAATGTC TGCTCTTTCG ACCTTAAAAA     360

AGCGCCTTGC TGCGTGTAAC CGAGCATCCC AATACAAGTT GGAAACAAGC TTAAACCCTA     420

TGCCTACATT TCGTTTGCTA CGCAATACGA AATGGTCATG GACACATTTG CAATATGTGT     480

TTCTAGCAGG TAATTTGATT TTTGCTTGTA TTGTCATTGA ATCTCCTGGA TTCTGGGGGA     540

AATTTGGCAT TGCCTGTCTT TTGGCCATTG CGTTGACCGT TCCTTTAACA CGCCAAATTT     600

TTTTTCCTGC CATTGTTATC ATCACCTGGG CAATTTTATT TTACTCTTGT AGGTTTATTC     660

CAGAACGCTG GCGTCCACCC ATATGGGTTC GTGTTTTACC CACACTTGAA AATATTCTTT     720

ATGGCTCTAA TCTTTCTAGT CTTCTCTCGA AAACCACGCA TAGCATCCTT GATATTTTGG     780

CCTGGGTTCC ATATGGAGTC ATGCATTATT CGGCTCCTTT TATCATTTCA TTTATTCTTT     840

TCATCTTTGC ACCTCCTGGA ACTCTTCCAG TTTGGGCTCG AACTTTTGGT TATATGAATT     900

TATTTGGTGT TCTTATCCAA ATGGCTTTCC CCTGTTCTCC TCCTTGGTAT GAAAATATGT     960

ATGGTTTAGA ACCTGCCACG TATGCAGTAC GTGGCTCTCC TGGTGGATTG GCCCGTATTG    1020

ATGCTCTCTT CGGCACTAGC ATTTACACTG ATGGTTTTTC TAACTCTCCG GTTGTTTTTG    1080

GTGCCTTTCC ATCTCTTCAC GCTGGATGGG CCATGCTGGA AGCACTTTTC CTTTCGCATG    1140

TGTTTCCTCG ATACCGCTTC TGCTTTTATG GATATGTTCT ATGGCTTTGC TGGTGTACTA    1200

TGTACCTTAC CCACCACTAC TTTGTAGATT TGGTCGGCGG TATGTGTTTA GCTATTATAT    1260
```

```
GCTTCGTTTT TGCTCAAAAG CTACGCCTCC CACAGTTGCA AACTGGTAAA ATCCTTCGTT      1320

GGGAATACGA GTTTGTTATC CACGGTCATG GTCTTTCCGA AAAAACCAGC AACTCCTTGG      1380

CTCGTACCGG CAGCCCATAC TTACTTGGAA GGGATTCTTT TACTCAAAAC CCTAATGCAG      1440

TAGCCTTCAT GAGTGGTCTT AACAATATGG AACTTGCTAA CACCGATCAT GAATGGTCCG      1500

TGGGTTCATC ATCACCTGAG CCGTTACCTA GTCCTGCTGC TGATTTGATT GATCGTCCTG      1560

CCAGTACCAC TTCCTCCATC TTTGATGCAA GTCATCTTCC TTAAATCAAC GTGCTTTAAG      1620

AATATATTTC CAAAAGCTAC ATGATACATT GACTAGAATC GGTTTGATTC ATAGTGGTAT      1680

TGGAATGATG TTGTTCATTG TGTTTTTTAA CTGTTAATCT GACATCCATT GAGTCATTCT      1740

TTACAATTTG TAAAATTAAT TTGTATCACT AATTTTGAAG GAAGCTATTT TGGTATTAAT      1800

ACCGCTTTTG GTCTCCACTT CCTTTTCGAA ACTCTTAACA GCGATTAGGC CGGGTATCTT      1860

CCAGTGTGAT GTATAGGTAT TTGTCGTTTT TTTATCATTT CCGTTAATAA AGAACTCTTT      1920

TATCCAGCTT CTTACACTGT CAACTGTTGT GAAAGGAACA CATTTAGAAT TCATTTTCC      1980

TTATTTGTTG TGATTTAAAT CGTTTGACAT AATTTTAAAT TTGGTTTGAA ATGTGTGTGA      2040

GAAGGCTTGT TTTATTCATT TAGTTTATTG CTTGTTTGCA CGAAAATCCA GAACGGAGCA      2100

TTAATGTAAT CCTTTTTTAT TCTGTAAAGC GTTTTTATAC AAATGTTGGT TATACGTTTC      2160

TAAAATAAGA ATATTGTTAT AATAATATAG TTTTTTCTAT CATTTGTTAC ACACACTAAA      2220

GAGACATTAA GGATAAGCAA ATGTGTTAAA ATGATAATAT ATTTTGGAAA CATTTATAAA      2280

GAAATTAAGC AGCTTTGACT AACTACATTT TTGTTTTTTT CCTAAGCAAA ACTGTATAGT      2340

TATACACGCG AGCTGTATTC ACTTCCATTG TAGTGACTTG AGCTC                     2385
```

(2) INFORMATION FOR SEQ ID NO:4:

(i) SEQUENCE CHARACTERISTICS:
  (A) LENGTH: 422
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

```
Met Ser Ala Leu Ser Thr Leu Lys Lys Arg Leu Ala Ala Cys Asn
 1               5                  10                  15

Arg Ala Ser Gln Tyr Lys Leu Glu Thr Ser Leu Asn Pro Met Pro
                20                  25                  30

Thr Phe Arg Leu Leu Arg Asn Thr Lys Trp Ser Trp Thr His Leu
                35                  40                  45

Gln Tyr Val Phe Leu Ala Gly Asn Leu Ile Phe Ala Cys Ile Val
                50                  55                  60

Ile Glu Ser Pro Gly Phe Trp Gly Lys Phe Gly Ile Ala Cys Leu
                65                  70                  75

Leu Ala Ile Ala Leu Thr Val Pro Leu Thr Arg Gln Ile Phe Phe
                80                  85                  90

Pro Ala Ile Val Ile Ile Thr Trp Ala Ile Leu Phe Tyr Ser Cys
                95                  100                 105

Arg Phe Ile Pro Glu Arg Trp Arg Pro Ile Trp Val Arg Val
                110                 115                 120

Leu Pro Thr Leu Glu Asn Ile Leu Tyr Gly Ser Asn Leu Ser Ser
                125                 130                 135
```

```
Leu Leu Ser Lys Thr Thr His Ser Ile Leu Asp Ile Leu Ala Trp
            140                 145                 150

Val Pro Tyr Gly Val Met His Tyr Ser Ala Pro Phe Ile Ile Ser
            155                 160                 165

Phe Ile Leu Phe Ile Phe Ala Pro Pro Gly Thr Leu Pro Val Trp
            170                 175                 180

Ala Arg Thr Phe Gly Tyr Met Asn Leu Phe Gly Val Leu Ile Gln
            185                 190                 195

Met Ala Phe Pro Cys Ser Pro Pro Trp Tyr Glu Asn Met Tyr Gly
            200                 205                 210

Leu Glu Pro Ala Thr Tyr Ala Val Arg Gly Ser Pro Gly Gly Leu
            215                 220                 225

Ala Arg Ile Asp Ala Leu Phe Gly Thr Ser Ile Tyr Thr Asp Gly
            230                 235                 240

Phe Ser Asn Ser Pro Val Val Phe Gly Ala Phe Pro Ser Leu His
            245                 250                 255

Ala Gly Trp Ala Met Leu Glu Ala Leu Phe Leu Ser His Val Phe
            260                 265                 270

Pro Arg Tyr Arg Phe Cys Phe Tyr Gly Tyr Val Leu Trp Leu Cys
            275                 280                 285

Trp Cys Thr Met Tyr Leu Thr His His Tyr Phe Val Asp Leu Val
            290                 295                 300

Gly Gly Met Cys Leu Ala Ile Ile Cys Phe Val Phe Ala Gln Lys
            305                 310                 315

Leu Arg Leu Pro Gln Leu Gln Thr Gly Lys Ile Leu Arg Trp Glu
            320                 325                 330

Tyr Glu Phe Val Ile His Gly His Gly Leu Ser Glu Lys Thr Ser
            335                 340                 345

Asn Ser Leu Ala Arg Thr Gly Ser Pro Tyr Leu Leu Gly Arg Asp
            350                 355                 360

Ser Phe Thr Gln Asn Pro Asn Ala Val Ala Phe Met Ser Gly Leu
            365                 370                 375

Asn Asn Met Glu Leu Ala Asn Thr Asp His Glu Trp Ser Val Gly
            380                 385                 390

Ser Ser Ser Pro Glu Pro Leu Pro Ser Pro Ala Ala Asp Leu Ile
            395                 400                 405

Asp Arg Pro Ala Ser Thr Thr Ser Ser Ile Phe Asp Ala Ser His
            410                 415                 420

Leu Pro (2) INFORMATION FOR SEQ ID NO:5:

(i) SEQUENCE CHARACTERISTICS:
        (A) LENGTH: 2340
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:5:

TTTCTTTCTG TCAAAGAATA ATAAAGTGCC CATCAGTGTT CATATTTGTT ACAAAGTGGT      60

TTTCTGATTT GGTACTACTG CAGAGGCGTA TTTTTTGCTT CAGTTACCAT AGCGTAAGAA     120

CACTAGCGAC TTTTGTTCGT GAACCAACAG AGTAGGATTT CTACTGCTAC ATCTCTTAGG    180

TAGTTGGTTA GTCCGATCGC TCACTTTTGG TTGTTGTTAA GTACTTCATA AGTTTATCCT    240
```

-continued

```
TTTCCTTTTT CACACTGAGC TACTTTGGGT ATAGCTTTTG GCCCAAGGAT CTTTGAATTT      300

TCTCCAAAAG TACTTTATTT TATATCCTAC AGGTTGCGGT TTTCATATTT TAAAAAGCTT      360

TTTAATCATT CCTTTGCGTA TGGCAAACCC TTTTTCGAGA TGGTTTCTAT CAGAGAGACC      420

TCCAAACTGC CATGTAGCCG ATTTAGAAAC AAGTTTAGAT CCCCATCAAA CGTTGTTGAA      480

GGTGCAAAAA TACAAACCCG CTTTAAGCGA CTGGGTGCAT ACATCTTCT TGGGATCCAT       540

CATGCTGTTT GTGTTCATTA CTAATCCCGC ACCTTGGATC TTCAAGATCC TTTTTTATTG     600

TTTCTTGGGC ACTTTATTCA TCATTCCAGC TACGTCACAG TTTTTCTTCA ATGCCTTGCC     660

CATCCTAACA TGGGTGGCGC TGTATTTCAC TTCATCGTAC TTTCCAGATG ACCGCAGGCC     720

TCCTATTACT GTCAAAGTGT TACCAGCGGT GGAAACAATT TTATACGGCG ACAATTTAAG     780

TGATATTCTT GCAACATCGA CGAATTCCTT TTTGGACATT TTAGCATGGT TACCGTACGG     840

ACTATTTCAT TATGGGGCCC CATTTGTCGT TGCTGCCATC TTATTCGTAT TTGGTCCACC     900

AACTGTTTTG CAAGGTTATG CTTTTGCATT TGGTTATATG AACCTGTTTG GTGTTATCAT     960

GCAAAATGTC TTTCCAGCCG CTCCCCCATG GTATAAAATT CTCTATGGAT TGCAATCAGC    1020

CAACTATGAT ATGCATGGCT CGCCTGGTGG ATTAGCTAGA ATTGATAAGC TACTCGGTAT    1080

TAATATGTAT ACTACAGCTT TTTCAAATTC CTCCGTCATT TTCGGTGCTT TTCCTTCACT    1140

GCATTCCGGG TGTGCTACTA TGGAAGCCCT GTTTTTCTGT TATTGTTTTC CAAAATTGAA    1200

GCCCTTGTTT ATTGCTTATG TTTGCTGGTT ATGGTGGTCA ACTATGTATC TGACACACCA    1260

TTATTTTGTA GACCTTATGG CAGGTTCTGT GCTGTCATAC GTTATTTTCC AGTACACAAA    1320

GTACACACAT TTACCAATTG TAGATACATC TCTTTTTTGC AGATGGTCAT ACACTTCAAT    1380

TGAGAAATAC GATATATCAA AGAGTGATCC ATTGGCTGCA GATTCAAACG ATATCGAAAG    1440

TGTCCCTTTG TCCAACTTGG AACTTGACTT TGATCTTAAT ATGACTGATG AACCCAGTGT    1500

AAGCCCTTCG TTATTTGATG GATCTACTTC TGTTTCTCGT TCGTCCGCCA CGTCTATAAC    1560

GTCACTAGGT GTAAAGAGGG CTTAATGAGT ATTTTATCTG CAATTACGGA TACGGTTGGT    1620

CTTATGTAGA TACATATAAA TATATATCTT TTTCTTTCTT TTTCTTAGTC AGGATTGTCG    1680

TTTAGCATAA TATACATGTA GTTTATTTAA TCACATACCA CTGATTATCT TTAGAATTTT    1740

ATAAATTTTT GAAATAAATG GGTGGCTTTT AATGGTGTCT ATGTTAAGTG AGGCTTTTAG    1800

AATGCTCTTC CTGCTTTGTT TATTATATGT GTATGAAAGA TATGTATGTA TTTACATGTG    1860

TTTGTAGCGT CCCCAGTCAA AACCTGTGCG CTATACCTAA ATGGATTGAT AATCTTCATT    1920

CACTAATTCT AAAATAGACT TCTTCCCCAA AGAACGGTGT AACGATGAGG CTCTATCCAG    1980

CTGCTTATCT AAATCAACTT TAACGATGGA TGATCTTATG ACACGGGGAT CTTTCTTTAA    2040

AGTTCTTAGA ATTTCAGACT GTACCGCAGC TGATGAATCA AACAGCATTA AAAGTGATA     2100

TGCTCGAAAA TGTTTTTCCT GGTCTTTCTT CATTATTTTA GGAAGATACC TTATGCCCAT    2160

GGGTACAATG TCCCTCACCA CACCTCTGTT TGAATAATC AGTTTCCCGA TTGTGGAAGA     2220

CAATTCTTTT GCTTCCAACT TGGCGCATT GGAGTTGGTT ATGCGAACAA GTCCGATCAG     2280

CTCATAAAGC ATCTTAGTGA AAAGGGTGGT TTTGCGTTAT TCTTTCCTCT GTTGAAGCTT    2340
```

(2) INFORMATION FOR SEQ ID NO:6:

(i) SEQUENCE CHARACTERISTICS:
        (A) LENGTH: 401
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Tyr Gly Ala Pro Phe Val Val Ala
               155                 160                 165

Ala Ile Leu Phe Val Phe Gly Pro Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Ala
               230                 235                 240

Phe Ser Asn Ser Ser Val Ile Phe Gly Ala Phe Pro Ser Leu His
               245                 250                 255

Ser Gly Cys Ala Thr Met Glu Ala Leu Phe Phe Cys Tyr Cys Phe
               260                 265                 270

Pro Lys Leu Lys Pro Leu Phe Ile Ala Tyr Val Cys Trp Leu Trp
               275                 280                 285

Trp Ser Thr Met Tyr Leu Thr His His Tyr Phe Val Asp Leu Met
               290                 295                 300

Ala Gly Ser Val Leu Ser Tyr Val Ile Phe Gln Tyr Thr Lys Tyr
               305                 310                 315

Thr His Leu Pro Ile Val Asp Thr Ser Leu Phe Cys Arg Trp Ser
               320                 325                 330

Tyr Thr Ser Ile Glu Lys Tyr Asp Ile Ser Lys Ser Asp Pro Leu
               335                 340                 345

Ala Ala Asp Ser Asn Asp Ile Glu Ser Val Pro Leu Ser Asn Leu
               350                 355                 360

Glu Leu Asp Phe Asp Leu Asn Met Thr Asp Glu Pro Ser Val Ser
               365                 370                 375
```

```
Pro Ser Leu Phe Asp Gly Ser Thr Ser Val Ser Arg Ser Ser Ala
            380                 385                 390

Thr Ser Ile Thr Ser Leu Gly Val Lys Arg Ala
            395                 400

(2) INFORMATION FOR SEQ ID NO:7:

(i) SEQUENCE CHARACTERISTICS:
        (A) LENGTH: 2340
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:7:
```

| | | | | | |
|---|---|---|---|---|---|
| TTTCTTTCTG | TCAAAGAATA | ATAAAGTGCC | CATCAGTGTT | CATATTTGTT | ACAAAGTGGT | 60 |
| TTTCTGATTT | GGTACTACTG | CAGAGGCGTA | TTTTTTGCTT | CAGTTACCAT | AGCGTAAGAA | 120 |
| CACTAGCGAC | TTTTGTTCGT | GAACCAACAG | AGTAGGATTT | CTACTGCTAC | ATCTCTTAGG | 180 |
| TAGTTGGTTA | GTCCGATCGC | TCACTTTTGG | TTGTTGTTAA | GTACTTCATA | AGTTTATCCT | 240 |
| TTTCCTTTTT | CACACTGAGC | TACTTTGGGT | ATAGCTTTTG | GCCCAAGGAT | CTTTGAATTT | 300 |
| TCTCCAAAAG | TACTTTATTT | TATATCCTAC | AGGTTGCGGT | TTTCATATTT | TAAAAAGCTT | 360 |
| TTTAATCATT | CCTTTGCGTA | TGGCAAACCC | TTTTTCGAGA | TGGTTTCTAT | CAGAGAGACC | 420 |
| TCCAAACTGC | CATGTAGCCG | ATTTAGAAAC | AAGTTTAGAT | CCCCATCAAA | CGTTGTTGAA | 480 |
| GGTGCAAAAA | TACAAACCCG | CTTTAAGCGA | CTGGGTGCAT | ACATCTTCT  | TGGGATCCAT | 540 |
| CATGCTGTTT | GTGTTCATTA | CTAATCCCGC | ACCTTGGATC | TTCAAGATCC | TTTTTTATTG | 600 |
| TTTCTTGGGC | ACTTTATTCA | TCATTCCAGC | TACGTCACAG | TTTTTCTTCA | ATGCCTTGCC | 660 |
| CATCCTAACA | TGGGTGGCGC | TGTATTTCAC | TTCATCGTAC | TTTCCAGATG | ACCGCAGGCC | 720 |
| TCCTATTACT | GTCAAAGTGT | TACCAGCGGT | GGAAACAATT | TTATACGGCG | ACAATTTAAG | 780 |
| TGATATTCTT | GCAACATCGA | CGAATTCCTT | TTTGGACATT | TTAGCATGGT | TACCGTACGG | 840 |
| ACTATTTCAT | TTTGGGGCCC | CATTTGTCGT | TGCTGCCATC | TTATTCGTAT | TTGGTCCACC | 900 |
| AACTGTTTTG | CAAGGTTATG | CTTTTGCATT | TGGTTATATG | AACCTGTTTG | GTGTTATCAT | 960 |
| GCAAAATGTC | TTTCCAGCCG | CTCCCCCATG | GTATAAAATT | CTCTATGGAT | GCAATCAGC  | 1020 |
| CAACTATGAT | ATGCATGGCT | CGCCTGGTGG | ATTAGCTAGA | ATTGATAAGC | TACTCGGTAT | 1080 |
| TAATATGTAT | ACTACAGCTT | TTTCAAATTC | CTCCGTCATT | TTCGGTGCTT | TTCCTTCACT | 1140 |
| GCATTCCGGG | TGTGCTACTA | TGGAAGCCCT | GTTTTTCTGT | TATTGTTTTC | CAAAATTGAA | 1200 |
| GCCCTTGTTT | ATTGCTTATG | TTTGCTGGTT | ATGGTGGTCA | ACTATGTATC | TGACACACCA | 1260 |
| TTATTTGTA  | GACCTTATGG | CAGGTTCTGT | GCTGTCATAC | GTTATTTTCC | AGTACACAAA | 1320 |
| GTACACACAT | TTACCAATTG | TAGATACATC | TCTTTTTTGC | AGATGGTCAT | ACACTTCAAT | 1380 |
| TGAGAAATAC | GATATATCAA | AGAGTGATCC | ATTGGCTGCA | GATTCAAACG | ATATCGAAAG | 1440 |
| TGTCCCTTTG | TCCAACTTGG | AACTTGACTT | TGATCTTAAT | ATGACTGATG | AACCCAGTGT | 1500 |
| AAGCCCTTCG | TTATTTGATG | GATCTACTTC | TGTTTCTCGT | TCGTCCGCCA | CGTCTATAAC | 1560 |
| GTCACTAGGT | GTAAAGAGGG | CTTAATGAGT | ATTTTATCTG | CAATTACGGA | TACGGTTGGT | 1620 |
| CTTATGTAGA | TACATATAAA | TATATATCTT | TTTCTTTCTT | TTTCTTAGTC | AGGATTGTCG | 1680 |
| TTTAGCATAA | TATACATGTA | GTTTATTTAA | TCACATACCA | CTGATTATCT | TTAGAATTTT | 1740 |
| ATAAATTTTT | GAAATAAATG | GGTGGCTTTT | AATGGTGTCT | ATGTTAAGTG | AGGCTTTTAG | 1800 |

-continued

```
AATGCTCTTC CTGCTTTGTT TATTATATGT GTATGAAAGA TATGTATGTA TTTACATGTG    1860

TTTGTAGCGT CCCCAGTCAA AACCTGTGCG CTATACCTAA ATGGATTGAT AATCTTCATT    1920

CACTAATTCT AAAATAGACT TCTTCCCCAA AGAACGGTGT AACGATGAGG CTCTATCCAG    1980

CTGCTTATCT AAATCAACTT TAACGATGGA TGATCTTATG ACACGGGGAT CTTTCTTTAA    2040

AGTTCTTAGA ATTTCAGACT GTACCGCAGC TGATGAATCA AACAGCATTA AAAAGTGATA    2100

TGCTCGAAAA TGTTTTTCCT GGTCTTTCTT CATTATTTTA GGAAGATACC TTATGCCCAT    2160

GGGTACAATG TCCCTCACCA CACCTCTGTT TTGAATAATC AGTTTCCCGA TTGTGGAAGA    2220

CAATTCTTTT GCTTCCAACT TTGGCGCATT GGAGTTGGTT ATGCGAACAA GTCCGATCAG    2280

CTCATAAAGC ATCTTAGTGA AAAGGGTGGT TTTGCGTTAT TCTTTCCTCT GTTGAAGCTT    2340
```

(2) INFORMATION FOR SEQ ID NO:8:

(i) SEQUENCE CHARACTERISTICS:
        (A) LENGTH: 401
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Phe Gly Ala Pro Phe Val Val Ala
               155                 160                 165

Ala Ile Leu Phe Val Phe Gly Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Ala
               230                 235                 240
```

Phe Ser Asn Ser Ser Val Ile Phe Gly Ala Phe Pro Ser Leu His
              245                 250                 255

Ser Gly Cys Ala Thr Met Glu Ala Leu Phe Phe Cys Tyr Cys Phe
              260                 265                 270

Pro Lys Leu Lys Pro Leu Phe Ile Ala Tyr Val Cys Trp Leu Trp
              275                 280                 285

Trp Ser Thr Met Tyr Leu Thr His His Tyr Phe Val Asp Leu Met
              290                 295                 300

Ala Gly Ser Val Leu Ser Tyr Val Ile Phe Gln Tyr Thr Lys Tyr
              305                 310                 315

Thr His Leu Pro Ile Val Asp Thr Ser Leu Phe Cys Arg Trp Ser
              320                 325                 330

Tyr Thr Ser Ile Glu Lys Tyr Asp Ile Ser Lys Ser Asp Pro Leu
              335                 340                 345

Ala Ala Asp Ser Asn Asp Ile Glu Ser Val Pro Leu Ser Asn Leu
              350                 355                 360

Glu Leu Asp Phe Asp Leu Asn Met Thr Asp Glu Pro Ser Val Ser
              365                 370                 375

Pro Ser Leu Phe Asp Gly Ser Thr Ser Val Ser Arg Ser Ser Ala
              380                 385                 390

Thr Ser Ile Thr Ser Leu Gly Val Lys Arg Ala
              395                 400

(2) INFORMATION FOR SEQ ID NO:9:

(i) SEQUENCE CHARACTERISTICS:
        (A) LENGTH: 5340
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:9:

AGCGCTTCTA TTTTCCTCCC CACCGCGAGG CGGAAATGGC ACATTTTTTT TCTTTTGCTT      60

CTGTGCTTTT GCTGTAATTT TTGGCATGTG CTATTGTATG AAGATAACGC GTGGTTCCGT     120

GGAAATAGCC GGAAATTTTG CCGGGAATAT GACGGACATG ATTTAACACC CGTGGAAATG     180

AAAAAAGCCA AGGTAAGAAA GTGGCAATAT TTTTCCTACA AATAGATCTG CTGTCCCTTA     240

GATGATTACC ATACATATAT ATATTTATTA CACACATCTG TCAGAGGTAG CTAGCGAAGG     300

TGTCACTGAA ATATTTTTTG TTCCAGTTAG TATAAATACG GAGGTAGAAC AGCTCTCCGC     360

GTGTATATCT TTTTTTGCGC TATACAAGAA CAGGAAGAAC GCATTTCCAT ACCTTTTTCT     420

CCTTACAGGT GCCCTCTGAG TAGTGTCACG AACGAGGAAA AAGATTAATA TTACTGTTTT     480

TATATTCAAA AAGAGTAAAG CCGTTGCTAT ATACGAATAT GACGATTACC GTGGGGGATG     540

CAGTTTCGGA GACGGAGCTG AAAACAAAA GTCAAACGT GGTACTATCT CCCAAGGCAT      600

CTGCTTCTTC AGACATAAGC ACAGATGTTG ATAAAGCACA ATCGTCTTCT TGGGATGACA     660

AATCTTTGCT GCCTACAGGT GAATATATTG TGGACAGAAA TAAGCCCCAA ACCTACTTGA     720

ATAGCGATGA TATCGAAAAA GTGACAGAAT CTGATATTTT CCCTCAGAAA CGTCTGTTTT     780

CATTCTTGCA CTCTAAGAAA ATTCCAGAAG TACCACAAAC CGATGACGAG AGGAAGATAT     840

ATCCTCTGTT CCATACAAAT ATTATCTCTA ACATGTTTTT TTGGTGGGTT CTACCCATCC     900

TGCGAGTTGG TTATAAGAGA ACGATACAGC CGAACGATCT CTTCAAAATG GATCCGAGGA     960

-continued

```
TGTCTATAGA GACCCTTTAT GACGACTTTG AAAAAAACAT GATTTACTAT TTTGAGAAGA    1020
CGAGGAAAAA ATACCGTAAA AGACATCCAG AAGCGACAGA AGAAGAGGTT ATGGAAAATG    1080
CCAAACTACC TAAACATACA GTTCTGAGAG CTTTATTATT CACTTTTAAG AAACAGTACT    1140
TCATGTCGAT AGTGTTTGCA ATTCTCGCTA ATTGTACATC CGGTTTTAAC CCCATGATTA    1200
CCAAGAGGCT AATTGAGTTT GTCGAAGAAA AGGCTATTTT TCATAGCATG CATGTTAACA    1260
AAGGTATTGG TTACGCTATT GGTGCATGTT TGATGATGTT CGTTAACGGG TTGACGTTCA    1320
ATCATTTCTT TCATACATCC CAACTGACTG GTGTGCAAGC TAAGTCTATT CTTACTAAAG    1380
CTGCCATGAA GAAAATGTTT AATGCATCTA ATTATGCGAG ACATTGTTTT CCTAACGGTA    1440
AAGTGACTTC TTTTGTAACA ACAGATCTCG CTAGAATTGA ATTGCCTTA TCTTTTCAGC     1500
CGTTTTTGGC TGGGTTCCCT GCAATTTTGG CTATTTGCAT TGTTTTATTG ATCGTTAACC    1560
TTGGACCCAT TGCCTTAGTT GGGATTGGTA TTTTTTTCGG TGGGTTTTTC ATATCCTTAT    1620
TTGCATTTAA GTTAATTCTG GCTTTAGAA TTGCTGCGAA CATCTTCACT GATGCTAGAG     1680
TTACCATGAT GAGAGAAGTG CTGAATAATA TAAAAATGAT TAAATATTAT ACGTGGGAGG    1740
ATGCGTATGA AAAAAATATT CAAGATATTA GGACCAAAGA GATTTCTAAA GTTAGAAAAA    1800
TGCAACTATC AAGAAATTTC TTGATTGCTA TGGCCATGTC TTTGCCTAGT ATTGCTTCAT    1860
TGGTCACTTT CCTTGCAATG TACAAAGTTA ATAAAGGAGG CAGGCAACCT GGTAATATTT    1920
TTGCCTCTTT ATCTTTATTT CAGGTCTTGA GTTTGCAAAT GTTTTTCTTA CCTATTGCTA    1980
TTGGTACTGG AATTGACATG ATCATTGGAT TGGGCCGTTT GCAAAGCTTA TTGGAGGCTC    2040
CAGAAGATGA TCCAAATCAG ATGATTGAAA TGAAGCCCTC TCCTGGCTTT GATCCAAAAT    2100
TGGCTCTAAA AATGACACAT TGCTCATTTG AGTGGGAAGA TTATGAATTA AACGACGCTA    2160
TTGAAGAAGC AAAAGGAGAA GCTAAAGATG AAGGTAAAAA GAACAAAAAA AAGCGTAAGG    2220
ATACATGGG TAAGCCATCT GCAAGTACTA ATAAGGCGAA AAGATTGGAC AATATGTTGA     2280
AAGACAGAGA CGGCCCGGAA GATTTAGAAA AAACTTCGTT TAGGGGTTTC AAGGACTTGA    2340
ACTTCGATAT TAAAAAGGGC GAATTTATTA TGATTACGGG ACCTATTGGT ACTGGTAAAT    2400
CTTCATTATT GAATGCGATG GCAGGATCAA TGAGAAAAAT TGATGGTAAG GTTGAAGTCA    2460
ACGGGACTT ATTAATGTGT GGTTATCCAT GGATTCAAAA TGCATCTGTA AGAGATAACA     2520
TCATATTCGG TTCACCATTC AATAAAGAAA AGTATGATGA AGTAGTTCGT GTTTGCTCTT    2580
TGAAAGCTGA TCTGGATATT TTACCGGCAG GCGATATGAC CGAAATTGGG AACGTGGTA    2640
TTACTTTATC TGGTGGTCAA AAGGCACGTA TCAATTTAGC CAGGTCTGTT TATAAGAAGA    2700
AGGATATTTA TGTATTCGAC GATGTCCTAA GTGCTGTCGA TTCTCGTGTT GGTAAACACA    2760
TCATGGATGA ATGTCTAACC GGAATGCTTG CTAATAAAAC CAGAATTTTA GCAACGCATC    2820
AGTTGTCACT GATTGAGAGA GCTTCTAGAG TCATCGTTTT AGGTACTGAT GGCCAAGTCG    2880
ATATTGGTAC TGTTGATGAG CTAAAAGCTC GTAATCAAAC TTTGATAAAT CTTTTACAAT    2940
TCTCTTCTCA AAATTCGGAG AAAGAGGATG AAGAACAGGA AGCGGTTGTT TCCGGTGAAT    3000
TGGGACAACT AAAATATGAA CCAGAGGTAA AGGAATTGAC TGAACTGAAG AAAAAGGCTA    3060
CAGAAATGTC ACAAACTGCA AATAGTGGTA AAATTGTAGC GGATGGTCAT ACTAGTAGTA    3120
AAGAAGAAAG AGCAGTCAAT AGTATCAGTC TGAAAATATA CCGTGAATAC ATTAAAGCTG    3180
CAGTAGGTAA GTGGGGTTTT ATCGCACTAC CGTTGTATGC AATTTTAGTC GTTGGAACCA    3240
CATTCTGCTC ACTTTTTTCT TCCGTTTGGT TATCTTACTG GACTGAGAAT AAATTCAAAA    3300
ACAGACCACC CAGTTTTTAT ATGGGTCTTT ACTCCTTCTT TGTGTTTGCT GCTTTCATAT    3360
```

```
TCATGAATGG CCAGTTCACC ATACTTTGCG CAATGGGTAT TATGGCATCG AAATGGTTAA    3420

ATTTGAGGGC TGTGAAAAGA ATTTTACACA CTCCAATGTC ATACATAGAT ACCACACCTT    3480

TGGGACGTAT TCTGAACAGA TTCACAAAAG ATACAGATAG CTTAGATAAT GAGTTAACCG    3540

AAAGTTTACG GTTGATGACA TCTCAATTTG CTAATATTGT AGGTGTTTGC GTCATGTGTA    3600

TTGTTTACTT GCCGTGGTTT GCTATCGCAA TTCCGTTTCT TTTGGTCATC TTTGTTCTGA    3660

TTGCTGATCA TTATCAGAGT TCTGGTAGAG AAATTAAAAG ACTTGAAGCT GTGCAACGGT    3720

CTTTTGTTTA CAATAATTTA AATGAAGTTT TGGGTGGGAT GGATACAATC AAAGCATACC    3780

GAAGTCAGGA ACGATTTTTG GCGAAATCAG ATTTTTTGAT CAACAAGATG AATGAGGCGG    3840

GATACCTTGT AGTTGTCCTG CAAAGATGGG TAGGTATTTT CCTTGATATG GTTGCTATCG    3900

CATTTGCACT AATTATTACG TTATTGTGTG TTACGAGAGC CTTTCCTATT TCCGCGGCTT    3960

CAGTTGGTGT TTTGTTGACT TATGTATTAC AATTGCCTGG TCTATTAAAT ACCATTTTAA    4020

GGGCAATGAC TCAAACAGAG AATGACATGA ATAGTGCCGA AGATTGGTA ACATATGCAA     4080

CTGAACTACC ACTAGAGGCA TCCTATAGAA AGCCCGAAAT GACACCTCCA GAGTCATGGC    4140

CCTCAATGGG CGAAATAATT TTTGAAAATG TTGATTTTGC CTATAGACCT GGTTTACCTA    4200

TAGTTTTAAA AAATCTTAAC TTGAATATCA AGAGTGGGGA AAAAATTGGT ATCTGTGGTC    4260

GTACAGGTGC TGGTAAGTCC ACTATTATGA GTGCCCTTTA CAGGTTGAAT GAATTGACCG    4320

CAGGTAAAAT TTTAATTGAC AATGTTGATA TAAGTCAGCT GGGACTTTTC GATTTAAGAA    4380

GAAAATTAGC CATCATTCCA CAAGATCCAG TATTATTTAG GGGTACGATT CGCAAGAACT    4440

TAGATCCATT TAATGAGCGT ACAGATGACG AATTATGGGA TGCATTGGTG AGAGGTGGTG    4500

CTATCGCCAA GGATGACTTG CCGGAAGTGA AATTGCAAAA ACCTGATGAA AATGGTACTC    4560

ATGGTAAAAT GCATAAGTTC CATTTAGATC AAGCAGTGGA AGAAGAGGGC TCCAATTTCT    4620

CCTTAGGTGA GAGACAACTA TTAGCATTAA CAAGGGCATT GGTCCGCCAA TCAAAAATAT    4680

TGATTTTGGA TGAGGCTACA TCCTCAGTGG ACTACGAAAC GGATGGCAAA ATCCAAACAC    4740

GTATTGTTGA GGAATTTGGA GATTGTACAA TTTTGTGTAT TGCTCACAGA CTGAAGACCA    4800

TTGTAAATTA TGATCGTATT CTTGTTTTAG AGAAGGGTGA AGTCGCAGAA TTCGATACAC    4860

CATGGACGTT GTTTAGTCAA GAAGATAGTA TTTTCAGAAG CATGTGTTCT AGATCTGGTA    4920

TTGTGGAAAA TGATTTCGAG AACAGAAGTT AATTTATATT ATTTGTTGCA TGATTTTTCT    4980

CTTTTATTTA TTTATATGTT GCCGATGGTA CAAATTAGTA CTAGAAAAGA AAACCCACTA    5040

CTATGACTTG CAGAAAAAGT TATGTGTGCC ATAGATAGAT ATAATTGCAT ACCCACATCG    5100

TATACTCAAA ATTCCGAAAA GAACATTTCA TTTTTTATGA GGCAAACTGA ACAACGCTTC    5160

GGTCCTTTTT TCATTCTAGA AATATATATT TATACATCAT TTTCAGAAGA TATTCAAAGA    5220

ACTTATTGGG ATGTCTATTT ACTGAATAAA GTATACACAA AAAACGAATT TAAAATGGAA    5280

GGCATAAATA GAAAACTTAG AAGTGAAAAT CCTAAAACCG AAGGATATTT CAAATACGTA    5340
```

(2) INFORMATION FOR SEQ ID NO:10:

(i) SEQUENCE CHARACTERISTICS:
        (A) LENGTH: 1477
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

-continued

```
Met Thr Ile Thr Val Gly Asp Ala Val Ser Glu Thr Glu Leu Glu
              5                  10                  15
Asn Lys Ser Gln Asn Val Val Leu Ser Pro Lys Ala Ser Ala Ser
             20                  25                  30
Ser Asp Ile Ser Thr Asp Val Asp Lys Asp Thr Ser Ser Ser Trp
             35                  40                  45
Asp Asp Lys Ser Leu Leu Pro Thr Gly Glu Tyr Ile Val Asp Arg
             50                  55                  60
Asn Lys Pro Gln Thr Tyr Leu Asn Ser Asp Asp Ile Glu Lys Val
             65                  70                  75
Thr Glu Ser Asp Ile Phe Pro Gln Lys Arg Leu Phe Ser Phe Leu
             80                  85                  90
His Ser Lys Lys Ile Pro Glu Val Pro Gln Thr Asp Asp Glu Arg
             95                 100                 105
Lys Ile Tyr Pro Leu Phe His Thr Asn Ile Ile Ser Asn Met Phe
            110                 115                 120
Phe Trp Trp Val Leu Pro Ile Leu Arg Val Gly Tyr Lys Arg Thr
            125                 130                 135
Ile Gln Pro Asn Asp Leu Phe Lys Met Asp Pro Arg Met Ser Ile
            140                 145                 150
Glu Thr Leu Tyr Asp Asp Phe Glu Lys Asn Met Ile Tyr Tyr Phe
            155                 160                 165
Glu Lys Thr Arg Lys Lys Tyr Arg Lys Arg His Pro Glu Ala Thr
            170                 175                 180
Glu Glu Glu Val Met Glu Asn Ala Lys Leu Pro Lys His Thr Val
            185                 190                 195
Leu Arg Ala Leu Leu Phe Thr Phe Lys Lys Gln Tyr Phe Met Ser
            200                 205                 210
Ile Val Phe Ala Ile Leu Ala Asn Cys Thr Ser Gly Phe Asn Pro
            215                 220                 225
Met Ile Thr Lys Arg Leu Ile Glu Phe Val Glu Glu Lys Ala Ile
            230                 235                 240
Phe His Ser Met His Val Asn Lys Gly Ile Gly Tyr Ala Ile Gly
            245                 250                 255
Ala Cys Leu Met Met Phe Val Asn Gly Leu Thr Phe Asn His Phe
            260                 265                 270
Phe His Thr Ser Gln Leu Thr Gly Val Gln Ala Lys Ser Ile Leu
            275                 280                 285
Thr Lys Ala Ala Met Lys Lys Met Phe Asn Ala Ser Asn Tyr Ala
            290                 295                 300
Arg His Cys Phe Pro Asn Gly Lys Val Thr Ser Phe Val Thr Thr
            305                 310                 315
Asp Leu Ala Arg Ile Glu Phe Ala Leu Ser Phe Gln Pro Phe Leu
            320                 325                 330
Ala Gly Phe Pro Ala Ile Leu Ala Ile Cys Ile Val Leu Leu Ile
            335                 340                 345
Val Asn Leu Gly Pro Ile Ala Leu Val Gly Ile Gly Ile Phe Phe
            350                 355                 360
Gly Gly Phe Phe Ile Ser Leu Phe Ala Phe Lys Leu Ile Leu Gly
            365                 370                 375
Phe Arg Ile Ala Ala Asn Ile Phe Thr Asp Ala Arg Val Thr Met
            380                 385                 390
```

-continued

```
Met Arg Glu Val Leu Asn Asn Ile Lys Met Ile Lys Tyr Tyr Thr
                395                 400                 405

Trp Glu Asp Ala Tyr Glu Lys Asn Ile Gln Asp Ile Arg Thr Lys
                410                 415                 420

Glu Ile Ser Lys Val Arg Lys Met Gln Leu Ser Arg Asn Phe Leu
                425                 430                 435

Ile Ala Met Ala Met Ser Leu Pro Ser Ile Ala Ser Leu Val Thr
                440                 445                 450

Phe Leu Ala Met Tyr Lys Val Asn Lys Gly Gly Arg Gln Pro Gly
                455                 460                 465

Asn Ile Phe Ala Ser Leu Ser Leu Phe Gln Val Leu Ser Leu Gln
                470                 475                 480

Met Phe Phe Leu Pro Ile Ala Ile Gly Thr Gly Ile Asp Met Ile
                485                 490                 495

Ile Gly Leu Gly Arg Leu Gln Ser Leu Leu Glu Ala Pro Glu Asp
                500                 505                 510

Asp Pro Asn Gln Met Ile Glu Met Lys Pro Ser Pro Gly Phe Asp
                515                 520                 525

Pro Lys Leu Ala Leu Lys Met Thr His Cys Ser Phe Glu Trp Glu
                530                 535                 540

Asp Tyr Glu Leu Asn Asp Ala Ile Glu Glu Ala Lys Gly Glu Ala
                545                 550                 555

Lys Asp Glu Gly Lys Lys Asn Lys Lys Arg Lys Asp Thr Trp
                560                 565                 570

Gly Lys Pro Ser Ala Ser Thr Asn Lys Ala Lys Arg Leu Asp Asn
                575                 580                 585

Met Leu Lys Asp Arg Asp Gly Pro Glu Asp Leu Glu Lys Thr Ser
                590                 595                 600

Phe Arg Gly Phe Lys Asp Leu Asn Phe Asp Ile Lys Lys Gly Glu
                605                 610                 615

Phe Ile Met Ile Thr Gly Pro Ile Gly Thr Gly Lys Ser Ser Leu
                620                 625                 630

Leu Asn Ala Met Ala Gly Ser Met Arg Lys Ile Asp Gly Lys Val
                635                 640                 645

Glu Val Asn Gly Asp Leu Leu Met Cys Gly Tyr Pro Trp Ile Gln
                650                 655                 660

Asn Ala Ser Val Arg Asp Asn Ile Ile Phe Gly Ser Pro Phe Asn
                665                 670                 675

Lys Glu Lys Tyr Asp Glu Val Val Arg Val Cys Ser Leu Lys Ala
                680                 685                 690

Asp Leu Asp Ile Leu Pro Ala Gly Asp Met Thr Glu Ile Gly Glu
                695                 700                 705

Arg Gly Ile Thr Leu Ser Gly Gly Gln Lys Ala Arg Ile Asn Leu
                710                 715                 720

Ala Arg Ser Val Tyr Lys Lys Asp Ile Tyr Val Phe Asp Asp
                725                 730                 735

Val Leu Ser Ala Val Asp Ser Arg Val Gly Lys His Ile Met Asp
                740                 745                 750

Glu Cys Leu Thr Gly Met Leu Ala Asn Lys Thr Arg Ile Leu Ala
                755                 760                 765

Thr His Gln Leu Ser Leu Ile Glu Arg Ala Ser Arg Val Ile Val
                770                 775                 780
```

```
Leu Gly Thr Asp Gly Gln Val Asp Ile Gly Thr Val Asp Glu Leu
            785                 790                 795

Lys Ala Arg Asn Gln Thr Leu Ile Asn Leu Leu Gln Phe Ser Ser
            800                 805                 810

Gln Asn Ser Glu Lys Glu Asp Glu Glu Gln Glu Ala Val Val Ser
            815                 820                 825

Gly Glu Leu Gly Gln Leu Lys Tyr Glu Pro Glu Val Lys Glu Leu
            830                 835                 840

Thr Glu Leu Lys Lys Lys Ala Thr Glu Met Ser Gln Thr Ala Asn
            845                 850                 855

Ser Gly Lys Ile Val Ala Asp Gly His Thr Ser Ser Lys Glu Glu
            860                 865                 870

Arg Ala Val Asn Ser Ile Ser Leu Lys Ile Tyr Arg Glu Tyr Ile
            875                 880                 885

Lys Ala Ala Val Gly Lys Trp Gly Phe Ile Ala Leu Pro Leu Tyr
            890                 895                 900

Ala Ile Leu Val Val Gly Thr Thr Phe Cys Ser Leu Phe Ser Ser
            905                 910                 915

Val Trp Leu Ser Tyr Trp Thr Glu Asn Lys Phe Lys Asn Arg Pro
            920                 925                 930

Pro Ser Phe Tyr Met Gly Leu Tyr Ser Phe Phe Val Phe Ala Ala
            935                 940                 945

Phe Ile Phe Met Asn Gly Gln Phe Thr Ile Leu Cys Ala Met Gly
            950                 955                 960

Ile Met Ala Ser Lys Trp Leu Asn Leu Arg Ala Val Lys Arg Ile
            965                 970                 975

Leu His Thr Pro Met Ser Tyr Ile Asp Thr Thr Pro Leu Gly Arg
            980                 985                 990

Ile Leu Asn Arg Phe Thr Lys Asp Thr Asp Ser Leu Asp Asn Glu
            995                1000                1005

Leu Thr Glu Ser Leu Arg Leu Met Thr Ser Gln Phe Ala Asn Ile
           1010                1015                1020

Val Gly Val Cys Val Met Cys Ile Val Tyr Leu Pro Trp Phe Ala
           1025                1030                1035

Ile Ala Ile Pro Phe Leu Leu Val Ile Phe Val Leu Ile Ala Asp
           1040                1045                1050

His Tyr Gln Ser Ser Gly Arg Glu Ile Lys Arg Leu Glu Ala Val
           1055                1060                1065

Gln Arg Ser Phe Val Tyr Asn Asn Leu Asn Glu Val Leu Gly Gly
           1070                1075                1080

Met Asp Thr Ile Lys Ala Tyr Arg Ser Gln Glu Arg Phe Leu Ala
           1085                1090                1095

Lys Ser Asp Phe Leu Ile Asn Lys Met Asn Glu Ala Gly Tyr Leu
           1100                1105                1110

Val Val Val Leu Gln Arg Trp Val Gly Ile Phe Leu Asp Met Val
           1115                1120                1125

Ala Ile Ala Phe Ala Leu Ile Ile Thr Leu Leu Cys Val Thr Arg
           1130                1135                1140

Ala Phe Pro Ile Ser Ala Ala Ser Val Gly Val Leu Leu Thr Tyr
           1145                1150                1155

Val Leu Gln Leu Pro Gly Leu Leu Asn Thr Ile Leu Arg Ala Met
           1160                1165                1170
```

```
Thr Gln Thr Glu Asn Asp Met Asn Ser Ala Glu Arg Leu Val Thr
        1175                1180                1185
Tyr Ala Thr Glu Leu Pro Leu Glu Ala Ser Tyr Arg Lys Pro Glu
        1190                1195                1200
Met Thr Pro Pro Glu Ser Trp Pro Ser Met Gly Glu Ile Ile Phe
        1205                1210                1215
Glu Asn Val Asp Phe Ala Tyr Arg Pro Gly Leu Pro Ile Val Leu
        1220                1225                1230
Lys Asn Leu Asn Leu Asn Ile Lys Ser Gly Glu Lys Ile Gly Ile
        1235                1240                1245
Cys Gly Arg Thr Gly Ala Gly Lys Ser Thr Ile Met Ser Ala Leu
        1250                1255                1260
Tyr Arg Leu Asn Glu Leu Thr Ala Gly Lys Ile Leu Ile Asp Asn
        1265                1270                1275
Val Asp Ile Ser Gln Leu Gly Leu Phe Asp Leu Arg Arg Lys Leu
        1280                1285                1290
Ala Ile Ile Pro Gln Asp Pro Val Leu Phe Arg Gly Thr Ile Arg
        1295                1300                1305
Lys Asn Leu Asp Pro Phe Asn Glu Arg Thr Asp Asp Glu Leu Trp
        1310                1315                1320
Asp Ala Leu Val Arg Gly Gly Ala Ile Ala Lys Asp Asp Leu Pro
        1325                1330                1335
Glu Val Lys Leu Gln Lys Pro Asp Glu Asn Gly Thr His Gly Lys
        1340                1345                1350
Met His Lys Phe His Leu Asp Gln Ala Val Glu Glu Glu Gly Ser
        1355                1360                1365
Asn Phe Ser Leu Gly Glu Arg Gln Leu Leu Ala Leu Thr Arg Ala
        1370                1375                1380
Leu Val Arg Gln Ser Lys Ile Leu Ile Leu Asp Glu Ala Thr Ser
        1385                1390                1395
Ser Val Asp Tyr Glu Thr Asp Gly Lys Ile Gln Thr Arg Ile Val
        1400                1405                1410
Glu Glu Phe Gly Asp Cys Thr Ile Leu Cys Ile Ala His Arg Leu
        1415                1420                1425
Lys Thr Ile Val Asn Tyr Asp Arg Ile Leu Val Leu Glu Lys Gly
        1430                1435                1440
Glu Val Ala Glu Phe Asp Thr Pro Trp Thr Leu Phe Ser Gln Glu
        1445                1450                1455
Asp Ser Ile Phe Arg Ser Met Cys Ser Arg Ser Gly Ile Val Glu
        1460                1465                1470
Asn Asp Phe Glu Asn Arg Ser
        1475

(2) INFORMATION FOR SEQ ID NO:11:

(i) SEQUENCE CHARACTERISTICS:
        (A) LENGTH:  26
        (B) TYPE:  nucleic acid
        (C) STRANDEDNESS:  single
        (D) TOPOLOGY:  linear (ii) MOLECULE TYPE: Other nucleic acid (synthetic DNA)

(xi) SEQUENCE DESCRIPTION: SEQ ID NO:11:

TTTGGTTAYA TGAAYYTNTT YGGNGT                                          26
```

```
(2) INFORMATION FOR SEQ ID NO:12:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:12:

TCTACAAART ARTGGTGNGT NARRTACAT                                              29

(2) INFORMATION FOR SEQ ID NO:13:

(i) SEQUENCE CHARACTERISTICS:
        (A) LENGTH: 2274
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:13:

TTATATATAT TATTGATTTG TTCCTGTTGT TATTTAGTTT AGAATCAGAC GACTACACCA            60

GAACCACAAT TCAACCAACA CTTATATAGA ACCTGGCTTG GAAAAAAGTA ACATTTATCA           120

TTCCTATACT TTTTTAGCAA ACATAATCCG TGTTTTACAT ATATTATTCA CCCAATATCA           180

TAACAAAAAC AAAACTGAATA ATGGCGTCTT CTATTTTGCG TTCCAAAATA ATACAAAAAC          240

CGTACCAATT ATTCCACTAC TATTTTCTTC TGGAGAAGGC TCCTGGTTCT ACAGTTAGTG           300

ATTTGAATTT TGATACAAAC ATACAAACGA GTTTACGTAA ATTAAAGCAT CATCATTGGA           360

CGGTGGGAGA AATATTCCAT TATGGGTTTT TGGTTTCCAT ACTTTTTTTC GTGTTTGTGG           420

TTTTCCCAGC TTCATTTTTT ATAAAATTAC CAATAATCTT AGCATTTGCT ACTTGTTTTT           480

TAATACCCTT AACATCACAA TTTTTTCTTC CTGCCTTGCC CGTTTTCACT TGGTTGGCAT           540

TATATTTTAC GTGTGCTAAA ATACCTCAAG AATGGAAACC AGCTATCACA GTTAAAGTTT           600

TACCAGCTAT GGAAACAATT TTGTACGGCG ATAATTTATC AAATGTTTTG GCAACCATCA           660

CTACCGGAGT GTTAGATATA TTGGCATGGT TACCATATGG GATTATTCAT TTCAGTTTCC           720

CATTTGTACT TGCTGCTATT ATATTTTTAT TTGGGCCACC GACGGCATTA AGATCATTTG           780

GATTTGCCTT TGGTTATATG AACTTGCTTG GAGTCTTGAT TCAAATGGCA TTCCCAGCTG           840

CTCCTCCATG GTACAAAAAC TTGCACGGAT TAGAACCAGC TAATTATTCA ATGCACGGGT           900

CTCCTGGTGG ACTTGGAAGG ATAGATAAAT TGTTAGGTGT TGATATGTAT ACCACAGGGT           960

TTTCCAATTC ATCAATCATT TTTGGGGCAT TCCCATCGTT ACATTCAGGA TGTTGTATCA          1020

TGGAAGTGTT ATTTTTGTGT TGGTTGTTTC CACGATTCAA GTTTGTGTGG GTTACATACG          1080

CATCTTGGCT TTGGTGGAGC ACGATGTATT TGACCCATCA CTACTTTGTC GATTTGATTG          1140

GTGGAGCCAT GCTATCTTTG ACTGTTTTTG AGTTCACCAA ATATAAATAT TTGCCAAAAA          1200

ACAAAGAAGG CCTTTTCTGT CGTTGGTCAT ACACTGAAAT TGAAAAAATC GATATCCAAG          1260

AGATTGACCC TTTATCATAC AATTATATCC CTGTCAACAG CAATGATAAT GAAAGCAGAT          1320

TGTATACGAG AGTGTACCAA GAGTCTCAGG TTAGTCCCCC ACAGAGAGCT GAAACACCTG          1380

AAGCATTTGA GATGTCAAAT TTTTCTAGGT CTAGACAAAG CTCAAAGACT CAGGTTCCAT          1440

TGAGTAATCT TACTAACAAT GATCAAGTGT CTGGAATTAA CGAAGAGGAT GAAGAAGAAG          1500

AAGGCGATGA AATTTCATCG AGTACTCCTT CGGTGTTTGA AGACGAACCA CAGGGTAGCA          1560
```

| | | |
|---|---|---|
| CATATGCTGC ATCCTCAGCT ACATCAGTAG ATGATTTGGA TTCCAAAAGA AATTAGTAAA | 1620 |
| ATAACAGTTT CTATTAATTT CTTTATTTCC TCCTAATTAA TGATTTTATG CTCAATACCT | 1680 |
| ACACTATCTG TTTTTAATTT CCTACTTTTT TTTTATTATT GTTGAGTTCA TTTGCTGTTC | 1740 |
| ATTGAATATT TACAATTTTG CATTAATTAC CATCAATATA GAATGGGCAC AGTTTTTTTA | 1800 |
| AGTTTTTTTG TTTTTGTGTT TGTCTTTCTT TTTTTACATT AATGTGTTTG GATTGTTTTA | 1860 |
| GGTTCCTTTA TCCCTTAGCC CCCTCAGAAT ACTATTTTAT CTAATTAATT TGTTTTTATT | 1920 |
| TTCTGATATT TACCAATTGC TTTTTCTTTT GGATATTTAT AATAGCATCC CCTAATAATT | 1980 |
| AATATACAAC TGTTTCATAT ATATACGTGT ATGTCCTGTA GTGGTGGAAA CTGGAGTCAA | 2040 |
| CATTTGTATT AATGTGTACA AGAAAGCAGT GTTAATGCTA CTATTATAAT TTTTGAGGTG | 2100 |
| CAAATCAAGA GGTTGGCAGC TTTCTTATGG CTATGACCGT GAATGAAGGC TTGTAAACCA | 2160 |
| CGTAATAAAC AAAAGCCAAC AAGTTTTTTT AGAGCCTTTA ACAACATACG CAATGAGAGT | 2220 |
| GATTGCAATA CTACAAGATA TAGCCCAAAA AATTGAATGC ATTTCAACAA CAAC | 2274 |

(2) INFORMATION FOR SEQ ID NO:14:

(i) SEQUENCE CHARACTERISTICS:
        (A) LENGTH: 471
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Ala Ser Ser Ile Leu Arg Ser Lys Ile Ile Gln Lys Pro Tyr
               5                      10                 15

Gln Leu Phe His Tyr Tyr Phe Leu Ser Glu Lys Ala Pro Gly Ser
              20                   25                30

Thr Val Ser Asp Leu Asn Phe Asp Thr Asn Ile Gln Thr Ser Leu
              35                   40                45

Arg Lys Leu Lys His His His Trp Thr Val Gly Glu Ile Phe His
              50                   55                60

Tyr Gly Phe Leu Val Ser Ile Leu Phe Val Phe Val Val Phe
              65                   70                75

Pro Ala Ser Phe Phe Ile Lys Leu Pro Ile Ile Leu Ala Phe Ala
              80                   85                90

Thr Cys Phe Leu Ile Pro Leu Thr Ser Gln Phe Phe Leu Pro Ala
              95                  100              105

Leu Pro Val Phe Thr Trp Leu Ala Leu Tyr Phe Thr Cys Ala Lys
             110                  115              120

Ile Pro Gln Glu Trp Lys Pro Ala Ile Thr Val Lys Val Leu Pro
             125                  130              135

Ala Met Glu Thr Ile Leu Tyr Gly Asp Asn Leu Ser Asn Val Leu
             140                  145              150

Ala Thr Ile Thr Thr Gly Val Leu Asp Ile Leu Ala Trp Leu Pro
             155                  160              165

Tyr Gly Ile Ile His Phe Ser Phe Pro Phe Val Leu Ala Ala Ile
             170                  175              180

Ile Phe Leu Phe Gly Pro Pro Thr Ala Leu Arg Ser Phe Gly Phe
             185                  190              195

Ala Phe Gly Tyr Met Asn Leu Leu Gly Val Leu Ile Gln Met Ala
             200                  205              210

```
Phe Pro Ala Ala Pro Pro Trp Tyr Lys Asn Leu His Gly Leu Glu
                215                 220                 225
Pro Ala Asn Tyr Ser Met His Gly Ser Pro Gly Gly Leu Gly Arg
            230                 235                 240
Ile Asp Lys Leu Leu Gly Val Asp Met Tyr Thr Thr Gly Phe Ser
            245                 250                 255
Asn Ser Ser Ile Ile Phe Gly Ala Phe Pro Ser Leu His Ser Gly
            260                 265                 270
Cys Cys Ile Met Glu Val Leu Phe Leu Cys Trp Leu Phe Pro Arg
            275                 280                 285
Phe Lys Phe Val Trp Val Thr Tyr Ala Ser Trp Leu Trp Trp Ser
            290                 295                 300
Thr Met Tyr Leu Thr His His Tyr Phe Val Asp Leu Ile Gly Gly
            305                 310                 315
Ala Met Leu Ser Leu Thr Val Phe Glu Phe Thr Lys Tyr Lys Tyr
            320                 325                 330
Leu Pro Lys Asn Lys Glu Gly Leu Phe Cys Arg Trp Ser Tyr Thr
            335                 340                 345
Glu Ile Glu Lys Ile Asp Ile Gln Glu Ile Asp Pro Leu Ser Tyr
            350                 355                 360
Asn Tyr Ile Pro Val Asn Ser Asn Asp Asn Glu Ser Arg Leu Tyr
            365                 370                 375
Thr Arg Val Tyr Gln Glu Ser Gln Val Ser Pro Pro Gln Arg Ala
            380                 385                 390
Glu Thr Pro Glu Ala Phe Glu Met Ser Asn Phe Ser Arg Ser Arg
            395                 400                 405
Gln Ser Ser Lys Thr Gln Val Pro Leu Ser Asn Leu Thr Asn Asn
            410                 415                 420
Asp Gln Val Ser Gly Ile Asn Glu Glu Asp Glu Glu Glu Glu Gly
            425                 430                 435
Asp Glu Ile Ser Ser Ser Thr Pro Ser Val Phe Glu Asp Glu Pro
            440                 445                 450
Gln Gly Ser Thr Tyr Ala Ala Ser Ser Ala Thr Ser Val Asp Asp
            455                 460                 465
Leu Asp Ser Lys Arg Asn
            470
```

(2) INFORMATION FOR SEQ ID NO:15:

(i) SEQUENCE CHARACTERISTICS:
        (A) LENGTH: 243
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:15:

```
TTTGAAAAAT TGAATTTTA AAATTAATCC AATGGAAAAA ATTGGTATTT GTGGAAGAAC    60
CGGTGCTGGT AAATCATCAA TTATGACAGC ATTATATCGA TTATCAGAAT TAGAACTGGG   120
GAAAATTATT ATTGATGATA TTGATATTTC AACTTTGGGT TTAAAAGATC TTCGATCAAA   180
ATTATCAATT ATTCCTCAAG ATCCAGTATT ATTCCGAGGT TCAATTCGGA AAAACTTGGA   240
TCC                                                                243
```

(2) INFORMATION FOR SEQ ID NO:16:

(i) SEQUENCE CHARACTERISTICS:
    (A) LENGTH: 80
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:16:

```
Leu Lys Asn Leu Asn Phe Lys Ile Asn Pro Met Glu Lys Ile Gly
              5                  10                  15
Ile Cys Gly Arg Thr Gly Ala Gly Lys Ser Ser Ile Met Thr Ala
             20                  25                  30
Leu Tyr Arg Leu Ser Glu Leu Glu Leu Gly Lys Ile Ile Ile Asp
             35                  40                  45
Asp Ile Asp Ile Ser Thr Leu Gly Leu Lys Asp Leu Arg Ser Lys
             50                  55                  60
Leu Ser Ile Ile Pro Gln Asp Pro Val Leu Phe Arg Gly Ser Ile
             65                  70                  75
Arg Lys Asn Leu Asp
             80
```

(2) INFORMATION FOR SEQ ID NO:17:

(i) SEQUENCE CHARACTERISTICS:
        (A) LENGTH: 1601
        (B) TYPE: nucleic acid
        (C) STRANDEDNESS: double
        (D) TOPOLOGY: linear (ii) MOLECULE TYPE: genomic DNA (iv) ANTI-SENSE: Yes (xi) SEQUENCE DESCRIPTION: SEQ ID NO:17:

```
AGGAAGATGA CTTGCATCAA AGATGGAGGA AGTGGTACTG GCAGGACGAT CAATCAAATC      60
AGCAGCAGGA CTAGGTAACG GCTCAGGTGA TGATGAACCC ACGGACCATT CATGATCGGT     120
GTTAGCAAGT TCCATATTGT TAAGACCACT CATGAAGGCT ACTGCATTAG GGTTTTGAGT     180
AAAAGAATCC CTTCCAAGTA AGTATGGGCT GCCGGTACGA GCCAAGGAGT TGCTGGTTTT     240
TTCGGAAAGA CCATGACCGT GGATAACAAA CTCGTATTCC CAACGAAGGA TTTTACCAGT     300
TTGCAACTGT GGGAGGCGTA GCTTTTGAGC AAAAACGAAG CATATAATAG CTAAACACAT     360
ACCGCCGACC AAATCTACAA AGTAGTGGTG GGTAAGGTAC ATAGTACACC AGCAAAGCCA     420
TAGAACATAT CCATAAAAGC AGAAGCGGTA TCGAGGAAAC ACATGCGAAA GGAAAAGTGC     480
TTCCAGCATG GCCCATCCAG CGTGAAGAGA TGGAAAGGCA CCAAAAACAA CCGGAGAGTT     540
AGAAAAACCA TCAGTGTAAA TGCTAGTGCC GAAGAGAGCA TCAATACGGG CCAATCCACC     600
AGGAGAGCCA CGTACTGCAT ACGTGGCAGG TTCTAAACCA TACATATTTT CATACCAAGG     660
AGGAGAACAG GGGAAAGCCA TTTGGATAAG AACACCAAAT AAATTCATAT AACCAAAAGT     720
TCGAGCCCAA ACTGGAAGAG TTCCAGGAGG TGCAAAGATG AAAAGAATAA ATGAAATGAT     780
AAAAGGAGCC GAATAATGCA TGACTCCATA TGGAACCCAG GCCAAAATAT CAAGGATGCT     840
ATGCGTGGTT TTCGAGAGAA GACTAGAAAG ATTAGAGCCA TAAAGAATAT TTTCAAGTGT     900
GGGTAAAACA CGAACCCATA TGGGTGGACG CCAGCGTTCT GGAATAAACC TACAAGAGTA     960
AAATAAAATT GCCCAGGTGA TGATAACAAT GGCAGGAAAA AAAATTTGGC GTGTTAAAGG    1020
AACGGTCAAC GCAATGGCCA AAAGACAGGC AATGCCAAAT TTCCCCCAGA ATCCAGGAGA    1080
```

-continued

```
TTCAATGACA ATACAAGCAA AAATCAAATT ACCTGCTAGA AACACATATT GCAAATGTGT    1140

CCATGACCAT TTCGTATTGC GTAGCAAACG AAATGTAGGC ATAGGGTTTA AGCTTGTTTC    1200

CAACTTGTAT TGGGATGCTC GGTTACACGC AGCAAGGCGC TTTTTTAAGG TCGAAAGAGC    1260

AGACATTGCT TCAAAGAATT ATCAGAGTAA AAAAGGGAAG CGTACGAAAA AAATTTCGTA    1320

AGGAATTAAC CGGAAAACTA AGGAAAAAA AAGGAATTTT TATGAAGGAA AGAAAGTAGC    1380

TATTAAATGC AAGTGTCAAG CACTTAAAAG TAGCGATGTA AAATATTTAA AAAAAGATGG    1440

ACCGATTAAC CAATGTTCAG CTCACAGTTG CCAGCAATCA GGGCTATTTT TTTATTTTTT    1500

TTATAAAATT GCTAATTATA TATAATATAA TTAGTTTATT AACTTGCTTT TCCTCAAAAA    1560

ACCAATTCGA GAAAGGAACT TTTGCAGAGG CAAAAAAGCT T                        1601
```

(2) INFORMATION FOR SEQ ID NO:18:

(i) SEQUENCE CHARACTERISTICS:
        (A) LENGTH: 1601
        (B) TYPE: nucleic acid
        (C) STRANDEDNESS: double
        (D) TOPOLOGY: linear (ii) MOLECULE TYPE: mRNA (iv) ANTI-SENSE: Yes (xi) SEQUENCE DESCRIPTION: SEQ ID NO:18:

```
AGGAAGAUGA CUUGCAUCAA AGAUGGAGGA AGUGGUACUG GCAGGACGAU CAAUCAAAUC      60

AGCAGCAGGA CUAGGUAACG GCUCAGGUGA UGAUGAACCC ACGGACCAUU CAUGAUCGGU     120

GUUAGCAAGU UCCAUAUUGU UAAGACCACU CAUGAAGGCU ACUGCAUUAG GGUUUUGAGU     180

AAAAGAAUCC CUUCCAAGUA AGUAUGGGCU GCCGGUACGA GCCAAGGAGU UGCUGGUUUU     240

UUCGGAAAGA CCAUGACCGU GGAUAACAAA CUCGUAUUCC CAACGAAGGA UUUUACCAGU     300

UUGCAACUGU GGGAGGCGUA GCUUUUGAGC AAAAACGAAG CAUAUAAUAG CUAAACACAU     360

ACCGCCGACC AAAUCUACAA AGUAGUGGUG GGUAAGGUAC AUAGUACACC AGCAAAGCCA     420

UAGAACAUAU CCAUAAAAGC AGAAGCGGUA UCGAGGAAAC ACAUGCGAAA GGAAAAGUGC     480

UUCCAGCAUG GCCCAUCCAG CGUGAAGAGA UGGAAAGGCA CCAAAAACAA CCGGAGAGUU     540

AGAAAAACCA UCAGUGUAAA UGCUAGUGCC GAAGAGAGCA UCAAUACGGG CCAAUCCACC     600

AGGAGAGCCA CGUACUGCAU ACGUGGCAGG UUCUAAACCA UACAUAUUUU CAUACCAAGG     660

AGGAGAACAG GGGAAAGCCA UUUGGAUAAG AACACCAAAU AAAUUCAUAU AACCAAAAGU     720

UCGAGCCCAA ACUGGAAGAG UUCCAGGAGG UGCAAAGAUG AAAAGAAUAA AUGAAAUGAU     780

AAAAGGAGCC GAAUAAUGCA UGACUCCAUA UGGAACCCAG GCCAAAAUAU CAAGGAUGCU     840

AUGCGUGGUU UUCGAGAGAA GACUAGAAAG AUUAGAGCCA UAAAGAAUAU UUCAAGUGU     900

GGGUAAAACA CGAACCCAUA UGGGUGGACG CCAGCGUUCU GGAAUAAACC UACAAGAGUA     960

AAAUAAAAUU GCCCAGGUGA UGAUAACAAU GGCAGGAAAA AAAAUUUGGC GUGUUAAAGG    1020

AACGGUCAAC GCAAUGGCCA AAAGACAGGC AAUGCCAAAU UCCCCCAGA AUCCAGGAGA     1080

UUCAAUGACA AUACAAGCAA AAAUCAAAUU ACCUGCUAGA AACACAUAUU GCAAAUGUGU    1140

CCAUGACCAU UUCGUAUUGC GUAGCAAACG AAAUGUAGGC AUAGGGUUUA AGCUUGUUUC    1200

CAACUUGUAU UGGGAUGCUC GGUUACACGC AGCAAGGCGC UUUUUUAAGG UCGAAAGAGC    1260

AGACAUUGCU UCAAAGAAUU AUCAGAGUAA AAAAGGGAAG CGUACGAAAA AAAUUUCGUA    1320

AGGAAUUAAC CGGAAAACUA AGGAAAAAA AAGGAAUUUU UAUGAAGGAA AGAAAGUAGC    1380
```

```
UAUUAAAUGC AAGUGUCAAG CACUUAAAAG UAGCGAUGUA AAAUAUUUAA AAAAAGAUGG    1440

ACCGAUUAAC CAAUGUUCAG CUCACAGUUG CCAGCAAUCA GGGCUAUUUU UUUAUUUUUU    1500

UUAUAAAAUU GCUAAUUAUA UAUAAUAUAA UUAGUUUAUU AACUUGCUUU UCCUCAAAAA    1560

ACCAAUUCGA GAAAGGAACU UUUGCAGAGG CAAAAAAGCU U                        1601
```

(2) INFORMATION FOR SEQ ID NO:19:

(i) SEQUENCE CHARACTERISTICS:
        (A) LENGTH: 12
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Cys Phe Thr Ser Ser Tyr Phe Pro Asp Asp Arg Arg
                5                   10
```

(2) INFORMATION FOR SEQ ID NO:20:

(i) SEQUENCE CHARACTERISTICS:
        (A) LENGTH: 19
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Cys Tyr Thr Ser Ile Glu Lys Tyr Asp Ile Ser Lys Ser Asp Pro
                5                   10                  15
Leu Ala Ala Asp
```

(2) INFORMATION FOR SEQ ID NO:21:

(i) SEQUENCE CHARACTERISTICS:
        (A) LENGTH: 1553
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:21:

```
TTTTACATAT ATTATTCACC CAATATCATA ACAAAAACAA ACTGAATGAT GGCATCTTCT      60

ATTTTGCGTT CCAAAATAAT ACAAAAACCG TACCAATTAT TCCACTACTA TTTTCTTCTG     120

GAGAAGGCTC CTGGTTCTAC AGTTAGTGAT TTGAATTTTG ATACAAACAT ACAAACGAGT     180

TTACGTAAAT TAAAGCATCA TCATTGGACG GTGGGAGAAA TATTCCATTA TGGGTTTTTG     240

GTTTCCATAC TTTTTTTCGT GTTTGTGGTT TTCCCAGCTT CATTTTTTAT AAAATTACCA     300

ATAATCTTAG CATTTGCTAC TTGTTTTTTA ATACCCTTAA CATCACAATT TTTTCTTCCT     360

GCCTTGCCCG TTTTCACTTG GTTGGCATTA TATTTTACGT GTGCTAAAAT ACCTCAAGAA     420

TGGAAACCAG CTATCACAGT TAAAGTTTTA CCAGCTATGG AAACAATTTT GTACGGCGAT     480

AATTTATCAA ATGTTTTGGC AACCATCACT ACCGGAGTGT TAGATATATT GGCATGGTTA     540

CCATATGGGA TTATTCATTT CAGTTTCCCA TTTGTACTTG CTGCTATTAT ATTTTTATTT     600

GGGCCACCGA CGGCATTAAG ATCATTTGGA TTTGCCTTTG GTTATATGAA CTTGCTTGGA     660

GTCTTGATTC AAATGGCATT CCCAGCTGCT CCTCCATGGT ACAAAAACTT GCACGGATTA     720
```

-continued

```
GAACCAGCTA ATTATTCAAT GCACGGGTCT CCTGGTGGAC TTGGAAGGAT AGATAAATTG     780
TTAGGTGTTG ATATGTATAC CACAGGGTTT TCCAATTCAT CAATCATTTT TGGGGCATTC     840
CCATCGTTAC ATTCAGGATG TTGTATCATG GAAGTGTTAT TTTTGTGTTG GTTGTTTCCA     900
CGATTCAAGT TTGTGTGGGT TACATACGCA TCTTGGCTTT GGTGGAGCAC GATGTATTTG     960
ACCCATCACT ACTTTGTCGA TTTGATTGGT GGAGCCATGC TATCTTTGAC TGTTTTTGAA    1020
TTCACCAAAT ATAAATATTT GCCAAAAAAC AAAGAAGGCC TTTTCTGTCG TTGGTCATAC    1080
ACTGAAATTG AAAAAATCGA TATCCAAGAG ATTGACCCTT TATCATACAA TTATATCCCT    1140
GTCAACAGCA ATGATAATGA AAGCAGATTG TATACGAGAG TGTACCAAGA GCCTCAGGTT    1200
AGTCCCCCAC AGAGAGCTGA AACACCTGAA GCATTTGAGA TGTCAAATTT TTCTAGGTCT    1260
AGACAAAGCT CAAAGACTCA GGTTCCATTG AGTAATCTTA CTAACAATGA TCAAGTGCCT    1320
GGAATTAACG AAGAGGATGA AGAAGAAGAA GGCGATGAAA TTTCGTCGAG TACTCCTTCG    1380
GTGTTTGAAG ACGAACCACA GGGTAGCACA TATGCTGCAT CCTCAGCTAC ATCAGTAGAT    1440
GATTTGGATT CCAAAAGAAA TTAGTAAAAC AGCAGTTTCT ATTAATTTCT TTATTTCCTC    1500
CTAATTAATG ATTTTATGTT CAATACCTAC ACTATCTGTT TTTAATTTCC TAC           1553
```

(2) INFORMATION FOR SEQ ID NO:22:

(i) SEQUENCE CHARACTERISTICS:
  (A) LENGTH: 472
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:22:

```
Met Met Ala Ser Ser Ile Leu Arg Ser Lys Ile Ile Gln Lys Pro
 1               5                  10                  15

Tyr Gln Leu Phe His Tyr Tyr Phe Leu Glu Lys Ala Pro Gly
                20                  25                  30

Ser Thr Val Ser Asp Leu Asn Phe Asp Thr Asn Ile Gln Thr Ser
                35                  40                  45

Leu Arg Lys Leu Lys His His His Trp Thr Val Gly Glu Ile Phe
                50                  55                  60

His Tyr Gly Phe Leu Val Ser Ile Leu Phe Phe Val Phe Val Val
                65                  70                  75

Phe Pro Ala Ser Phe Ile Lys Leu Pro Ile Ile Leu Ala Phe
                80                  85                  90

Ala Thr Cys Phe Leu Ile Pro Leu Thr Ser Gln Phe Phe Leu Pro
                95                 100                 105

Ala Leu Pro Val Phe Thr Trp Leu Ala Leu Tyr Phe Thr Cys Ala
               110                 115                 120

Lys Ile Pro Gln Glu Trp Lys Pro Ala Ile Thr Val Lys Val Leu
               125                 130                 135

Pro Ala Met Glu Thr Ile Leu Tyr Gly Asp Asn Leu Ser Asn Val
               140                 145                 150

Leu Ala Thr Ile Thr Thr Gly Val Leu Asp Ile Leu Ala Trp Leu
               155                 160                 165

Pro Tyr Gly Ile Ile His Phe Ser Phe Pro Phe Val Leu Ala Ala
               170                 175                 180

Ile Ile Phe Leu Phe Gly Pro Pro Thr Ala Leu Arg Ser Phe Gly
```

-continued

```
                185                 190                 195
Phe Ala Phe Gly Tyr Met Asn Leu Leu Gly Val Leu Ile Gln Met
                200                 205                 210
Ala Phe Pro Ala Ala Pro Pro Trp Tyr Lys Asn Leu His Gly Leu
                215                 220                 225
Glu Pro Ala Asn Tyr Ser Met His Gly Ser Pro Gly Leu Gly
                230                 235                 240
Arg Ile Asp Lys Leu Leu Gly Val Asp Met Tyr Thr Thr Gly Phe
                245                 250                 255
Ser Asn Ser Ser Ile Ile Phe Gly Ala Phe Pro Ser Leu His Ser
                260                 265                 270
Gly Cys Cys Ile Met Glu Val Leu Phe Leu Cys Trp Leu Phe Pro
                275                 280                 285
Arg Phe Lys Phe Val Trp Val Thr Tyr Ala Ser Trp Leu Trp Trp
                290                 295                 300
Ser Thr Met Tyr Leu Thr His His Tyr Phe Val Asp Leu Ile Gly
                305                 310                 315
Gly Ala Met Leu Ser Leu Thr Val Phe Glu Phe Thr Lys Tyr Lys
                320                 325                 330
Tyr Leu Pro Lys Asn Lys Glu Gly Leu Phe Cys Arg Trp Ser Tyr
                335                 340                 345
Thr Glu Ile Glu Lys Ile Asp Ile Gln Glu Ile Asp Pro Leu Ser
                350                 355                 360
Tyr Asn Tyr Ile Pro Val Asn Ser Asn Asp Asn Glu Ser Arg Leu
                365                 370                 375
Tyr Thr Arg Val Tyr Gln Glu Pro Gln Val Ser Pro Pro Gln Arg
                380                 385                 390
Ala Glu Thr Pro Glu Ala Phe Glu Met Ser Asn Phe Ser Arg Ser
                395                 400                 405
Arg Gln Ser Ser Lys Thr Gln Val Pro Leu Ser Asn Leu Thr Asn
                410                 415                 420
Asn Asp Gln Val Pro Gly Ile Asn Glu Glu Asp Glu Glu Glu
                425                 430                 435
Gly Asp Glu Ile Ser Ser Ser Thr Pro Ser Val Phe Glu Asp Glu
                440                 445                 450
Pro Gln Gly Ser Thr Tyr Ala Ala Ser Ser Ala Thr Ser Val Asp
                455                 460                 465
Asp Leu Asp Ser Lys Arg Asn
                470
```

(2) INFORMATION FOR SEQ ID NO:23:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:23:

GACTATTTCA TTATGGGGCC CC                                    22

(2) INFORMATION FOR SEQ ID NO:24:

(i) SEQUENCE CHARACTERISTICS:
        (A) LENGTH: 30

```
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO:24:

GTTAACTCGA GAAAGTGCCC ATCAGTGTTC                                   30

(2) INFORMATION FOR SEQ ID NO:25:

(i) SEQUENCE CHARACTERISTICS:
            (A) LENGTH: 29
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO:25:

GTTAACGGTA CCTCATCGTT ACACCGTTC                                    29

(2) INFORMATION FOR SEQ ID NO:26:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO:26:

GCTAAACGAC AATCCTGAC                                               19

(2) INFORMATION FOR SEQ ID NO:27:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: Other nucleic acid (synthetic DNA)

(xi) SEQUENCE DESCRIPTION: SEQ ID NO:27:

CGTTGGCCGA TTCATTAATG C                                            21

(2) INFORMATION FOR SEQ ID NO:28:

(i) SEQUENCE CHARACTERISTICS:
            (A) LENGTH: 401
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60
```

```
Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Phe Gly Ala Pro Phe Val Val Ala
               155                 160                 165

Ala Ile Leu Phe Val Phe Gly Pro Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Cys
               230                 235                 240

Phe Ser Asn Ser Ser Val Ile Phe Gly Ala Phe Pro Ser Leu His
               245                 250                 255

Ser Gly Cys Ala Thr Met Glu Ala Leu Phe Phe Cys Tyr Cys Phe
               260                 265                 270

Pro Lys Leu Lys Pro Leu Phe Ile Ala Tyr Val Cys Trp Leu Trp
               275                 280                 285

Trp Ser Thr Met Tyr Leu Thr His His Tyr Phe Val Asp Leu Met
               290                 295                 300

Ala Gly Ser Val Leu Ser Tyr Val Ile Phe Gln Tyr Thr Lys Tyr
               305                 310                 315

Thr His Leu Pro Ile Val Asp Thr Ser Leu Phe Cys Arg Trp Ser
               320                 325                 330

Tyr Thr Ser Ile Glu Lys Tyr Asp Ile Ser Lys Ser Asp Pro Leu
               335                 340                 345

Ala Ala Asp Ser Asn Asp Ile Glu Ser Val Pro Leu Ser Asn Leu
               350                 355                 360

Glu Leu Asp Phe Asp Leu Asn Met Thr Asp Glu Pro Ser Val Ser
               365                 370                 375

Pro Ser Leu Phe Asp Gly Ser Thr Ser Val Ser Arg Ser Ser Ala
               380                 385                 390

Thr Ser Ile Thr Ser Leu Gly Val Lys Arg Ala
               395                 400
```

(2) INFORMATION FOR SEQ ID NO:29:

(i) SEQUENCE CHARACTERISTICS:
        (A) LENGTH: 401
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO:29:

```
Met Ala Asn Pro Phe Ser Arg Trp Phe Leu Ser Glu Arg Pro Pro
 1               5                  10                  15

Asn Cys His Val Ala Asp Leu Glu Thr Ser Leu Asp Pro His Gln
                20                  25                  30

Thr Leu Leu Lys Val Gln Lys Tyr Lys Pro Ala Leu Ser Asp Trp
                35                  40                  45

Val His Tyr Ile Phe Leu Gly Ser Ile Met Leu Phe Val Phe Ile
                50                  55                  60

Thr Asn Pro Ala Pro Trp Ile Phe Lys Ile Leu Phe Tyr Cys Phe
                65                  70                  75

Leu Gly Thr Leu Phe Ile Ile Pro Ala Thr Ser Gln Phe Phe Phe
                80                  85                  90

Asn Ala Leu Pro Ile Leu Thr Trp Val Ala Leu Tyr Phe Thr Ser
                95                 100                 105

Ser Tyr Phe Pro Asp Asp Arg Arg Pro Pro Ile Thr Val Lys Val
               110                 115                 120

Leu Pro Ala Val Glu Thr Ile Leu Tyr Gly Asp Asn Leu Ser Asp
               125                 130                 135

Ile Leu Ala Thr Ser Thr Asn Ser Phe Leu Asp Ile Leu Ala Trp
               140                 145                 150

Leu Pro Tyr Gly Leu Phe His Tyr Gly Ala Pro Phe Val Val Ala
               155                 160                 165

Ala Ile Leu Phe Val Phe Gly Pro Pro Thr Val Leu Gln Gly Tyr
               170                 175                 180

Ala Phe Ala Phe Gly Tyr Met Asn Leu Phe Gly Val Ile Met Gln
               185                 190                 195

Asn Val Phe Pro Ala Ala Pro Pro Trp Tyr Lys Ile Leu Tyr Gly
               200                 205                 210

Leu Gln Ser Ala Asn Tyr Asp Met His Gly Ser Pro Gly Gly Leu
               215                 220                 225

Ala Arg Ile Asp Lys Leu Leu Gly Ile Asn Met Tyr Thr Thr Cys
               230                 235                 240

Phe Ser Asn Ser Ser Val Ile Phe Gly Ala Phe Pro Ser Leu His
               245                 250                 255

Ser Gly Cys Ala Thr Met Glu Ala Leu Phe Phe Cys Tyr Cys Phe
               260                 265                 270

Pro Lys Leu Lys Pro Leu Phe Ile Ala Tyr Val Cys Trp Leu Trp
               275                 280                 285

Trp Ser Thr Met Tyr Leu Thr His His Tyr Phe Val Asp Leu Met
               290                 295                 300

Ala Gly Ser Val Leu Ser Tyr Val Ile Phe Gln Tyr Thr Lys Tyr
               305                 310                 315

Thr His Leu Pro Ile Val Asp Thr Ser Leu Phe Cys Arg Trp Ser
               320                 325                 330

Tyr Thr Ser Ile Glu Lys Tyr Asp Ile Ser Lys Ser Asp Pro Leu
               335                 340                 345

Ala Ala Asp Ser Asn Asp Ile Glu Ser Val Pro Leu Ser Asn Leu
               350                 355                 360

Glu Leu Asp Phe Asp Leu Asn Met Thr Asp Glu Pro Ser Val Ser
               365                 370                 375
```

```
Pro Ser Leu Phe Asp Gly Ser Thr Ser Val Ser Arg Ser Ser Ala
            380                 385                 390

Thr Ser Ile Thr Ser Leu Gly Val Lys Arg Ala
            395                 400
```

(2) INFORMATION FOR SEQ ID NO:30:

(i) SEQUENCE CHARACTERISTICS:
        (A) LENGTH: 1206
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:30:

```
ATGGCAAACC CTTTTTCGAG ATGGTTTCTA TCAGAGAGAC CTCCAAACTG CCATGTAGCC      60
GATTTAGAAA CAAGTTTAGA TCCCCATCAA ACGTTGTTGA AGGTGCAAAA ATACAAACCC     120
GCTTTAAGCG ACTGGGTGCA TTACATCTTC TTGGGATCCA TCATGCTGTT TGTGTTCATT     180
ACTAATCCCG CACCTTGGAT CTTCAAGATC CTTTTTTATT GTTTCTTGGG CACTTTATTC     240
ATCATTCCAG CTACGTCACA GTTTTTCTTC AATGCCTTGC CCATCCTAAC ATGGGTGGCG     300
CTGTATTTCA CTTCATCGTA CTTTCCAGAT GACCGCAGGC CTCCTATTAC TGTCAAAGTG     360
TTACCAGCGG TGGAAACAAT TTTATACGGC GACAATTTAA GTGATATTCT TGCAACATCG     420
ACGAATTCCT TTTTGGACAT TTTAGCATGG TTACCGTACG GACTATTTCA TTTTGGGGCC     480
CCATTTGTCG TTGCTGCCAT CTTATTCGTA TTTGGTCCAC CAACTGTTTT GCAAGGTTAT     540
GCTTTTGCAT TTGGTTATAT GAACCTGTTT GGTGTTATCA TGCAAAATGT CTTTCCAGCC     600
GCTCCCCCAT GGTATAAAAT TCTCTATGGA TTGCAATCAG CCAACTATGA TATGCATGGC     660
TCGCCTGGTG GATTAGCTAG AATTGATAAG CTACTCGGTA TTAATATGTA TACTACATGT     720
TTTTCAAATT CCTCCGTCAT TTTCGGTGCT TTTCCTTCAC TGCATTCCGG GTGTGCTACT     780
ATGGAAGCCC TGTTTTTCTG TTATTGTTTT CCAAAATTGA AGCCCTTGTT TATTGCTTAT     840
GTTTGCTGGT TATGGTGGTC AACTATGTAT CTGACACACC ATTATTTTGT AGACCTTATG     900
GCAGGTTCTG TGCTGTCATA CGTTATTTTC CAGTACACAA AGTACACACA TTTACCAATT     960
GTAGATACAT CTCTTTTTTG CAGATGGTCA TACACTTCAA TTGAGAAATA CGATATATCA    1020
AAGAGTGATC CATTGGCTGC AGATTCAAAC GATATCGAAA GTGTCCCTTT GTCCAACTTG    1080
GAACTTGACT TTGATCTTAA TATGACTGAT GAACCCAGTG TAAGCCCTTC GTTATTTGAT    1140
GGATCTACTT CTGTTTCTCG TTCGTCCGCC ACGTCTATAA CGTCACTAGG TGTAAAGAGG    1200
GCTTAA                                                              1206
```

(2) INFORMATION FOR SEQ ID NO:31:

(i) SEQUENCE CHARACTERISTICS:
        (A) LENGTH: 1206
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:31:

```
ATGGCAAACC CTTTTTCGAG ATGGTTTCTA TCAGAGAGAC CTCCAAACTG CCATGTAGCC      60
GATTTAGAAA CAAGTTTAGA TCCCCATCAA ACGTTGTTGA AGGTGCAAAA ATACAAACCC     120
GCTTAAGCG ACTGGGTGCA TTACATCTTC TTGGGATCCA TCATGCTGTT TGTGTTCATT     180
```

```
ACTAATCCCG CACCTTGGAT CTTCAAGATC CTTTTTTATT GTTTCTTGGG CACTTTATTC      240

ATCATTCCAG CTACGTCACA GTTTTTCTTC AATGCCTTGC CCATCCTAAC ATGGGTGGCG      300

CTGTATTTCA CTTCATCGTA CTTTCCAGAT GACCGCAGGC CTCCTATTAC TGTCAAAGTG      360

TTACCAGCGG TGGAAACAAT TTTATACGGC GACAATTTAA GTGATATTCT TGCAACATCG      420

ACGAATTCCT TTTTGGACAT TTTAGCATGG TTACCGTACG GACTATTTCA TTATGGGGCC      480

CCATTTGTCG TTGCTGCCAT CTTATTCGTA TTTGGTCCAC CAACTGTTTT GCAAGGTTAT      540

GCTTTTGCAT TTGGTTATAT GAACCTGTTT GGTGTTATCA TGCAAAATGT CTTTCCAGCC      600

GCTCCCCCAT GGTATAAAAT TCTCTATGGA TTGCAATCAG CCAACTATGA TATGCATGGC      660

TCGCCTGGTG GATTAGCTAG AATTGATAAG CTACTCGGTA TTAATATGTA TACTACATGT      720

TTTTCAAATT CCTCCGTCAT TTTCGGTGCT TTTCCTTCAC TGCATTCCGG GTGTGCTACT      780

ATGGAAGCCC TGTTTTTCTG TTATTGTTTT CCAAAATTGA AGCCCTTGTT TATTGCTTAT      840

GTTTGCTGGT TATGGTGGTC AACTATGTAT CTGACACACC ATTATTTTGT AGACCTTATG      900

GCAGGTTCTG TGCTGTCATA CGTTATTTTC CAGTACACAA AGTACACACA TTTACCAATT      960

GTAGATACAT CTCTTTTTTG CAGATGGTCA TACACTTCAA TTGAGAAATA CGATATATCA     1020

AAGAGTGATC CATTGGCTGC AGATTCAAAC GATATCGAAA GTGTCCCTTT GTCCAACTTG     1080

GAACTTGACT TTGATCTTAA TATGACTGAT GAACCCAGTG TAAGCCCTTC GTTATTTGAT     1140

GGATCTACTT CTGTTTCTCG TTCGTCCGCC ACGTCTATAA CGTCACTAGG TGTAAAGAGG     1200

GCTTAA                                                                1206
```

(2) INFORMATION FOR SEQ ID NO:32:

(i) SEQUENCE CHARACTERISTICS:
        (A) LENGTH: 1206
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:32:

```
ATGGCAAACC CTTTTTCGAG ATGGTTTCTA TCAGAGAGAC CTCCAAACTG CCATGTAGCC       60

GATTTAGAAA CAAGTTTAGA TCCCCATCAA ACGTTGTTGA AGGTGCAAAA ATACAAACCC      120

GCTTTAAGCG ACTGGGTGCA TTACATCTTC TTGGGATCCA TCATGCTGTT TGTGTTCATT      180

ACTAATCCCG CACCTTGGAT CTTCAAGATC CTTTTTTATT GTTTCTTGGG CACTTTATTC      240

ATCATTCCAG CTACGTCACA GTTTTTCTTC AATGCCTTGC CCATCCTAAC ATGGGTGGCG      300

CTGTATTTCA CTTCATCGTA CTTTCCAGAT GACCGCAGGC CTCCTATTAC TGTCAAAGTG      360

TTACCAGCGG TGGAAACAAT TTTATACGGC GACAATTTAA GTGATATTCT TGCAACATCG      420

ACGAATTCCT TTTTGGACAT TTTAGCATGG TTACCGTACG GACTATTTCA TTATGGGGCC      480

CCATTTGTCG TTGCTGCCAT CTTATTCGTA TTTGGTCCAC CAACTGTTTT GCAAGGTTAT      540

GCTTTTGCAT TTGGTTATAT GAACCTGTTT GGTGTTATCA TGCAAAATGT CTTTCCAGCC      600

GCTCCCCCAT GGTATAAAAT TCTCTATGGA TTGCAATCAG CCAACTATGA TATGCATGGC      660

TCGCCTGGTG GATTAGCTAG AATTGATAAG CTACTCGGTA TTAATATGTA TACTACAGCT      720

TTTTCAAATT CCTCCGTCAT TTTCGGTGCT TTTCCTTCAC TGCATTCCGG GTGTGCTACT      780

ATGGAAGCCC TGTTTTTCTG TTATTGTTTT CCAAAATTGA AGCCCTTGTT TATTGCTTAT      840

GTTTGCTGGT TATGGTGGTC AACTATGTAT CTGACACACC ATTATTTTGT AGACCTTATG      900
```

```
GCAGGTTCTG TGCTGTCATA CGTTATTTTC CAGTACACAA AGTACACACA TTTACCAATT      960

GTAGATACAT CTCTTTTTTG CAGATGGTCA TACACTTCAA TTGAGAAATA CGATATATCA     1020

AAGAGTGATC CATTGGCTGC AGATTCAAAC GATATCGAAA GTGTCCCTTT GTCCAACTTG     1080

GAACTTGACT TTGATCTTAA TATGACTGAT GAACCCAGTG TAAGCCCTTC GTTATTTGAT     1140

GGATCTACTT CTGTTTCTCG TTCGTCCGCC ACGTCTATAA CGTCACTAGG TGTAAAGAGG     1200

GCTTAA                                                                1206

(2) INFORMATION FOR SEQ ID NO:33:

(i) SEQUENCE CHARACTERISTICS:
        (A) LENGTH:  1206
        (B) TYPE:  nucleic acid
        (C) STRANDEDNESS:  double
        (D) TOPOLOGY:  linear (ii) MOLECULE TYPE: Genomic DNA (xi) SEQUENCE DESCRIPTION: SEQ ID NO:33:

ATGGCAAACC CTTTTTCGAG ATGGTTTCTA TCAGAGAGAC CTCCAAACTG CCATGTAGCC       60

GATTTAGAAA CAAGTTTAGA TCCCCATCAA ACGTTGTTGA AGGTGCAAAA ATACAAACCC      120

GCTTTAAGCG ACTGGGTGCA TTACATCTTC TTGGGATCCA TCATGCTGTT TGTGTTCATT      180

ACTAATCCCG CACCTTGGAT CTTCAAGATC CTTTTTTATT GTTTCTTGGG CACTTTATTC      240

ATCATTCCAG CTACGTCACA GTTTTTCTTC AATGCCTTGC CCATCCTAAC ATGGGTGGCG      300

CTGTATTTCA CTTCATCGTA CTTTCCAGAT GACCGCAGGC CTCCTATTAC TGTCAAAGTG      360

TTACCAGCGG TGGAAACAAT TTTATACGGC GACAATTTAA GTGATATTCT TGCAACATCG      420

ACGAATTCCT TTTTGGACAT TTTAGCATGG TTACCGTACG GACTATTTCA TTTTGGGGCC      480

CCATTTGTCG TTGCTGCCAT CTTATTCGTA TTTGGTCCAC CAACTGTTTT GCAAGGTTAT      540

GCTTTTGCAT TGGTTATAT GAACCTGTTT GGTGTTATCA TGCAAAATGT CTTTCCAGCC      600

GCTCCCCCAT GGTATAAAAT TCTCTATGGA TTGCAATCAG CCAACTATGA TATGCATGGC      660

TCGCCTGGTG GATTAGCTAG AATTGATAAG CTACTCGGTA TTAATATGTA TACTACAGCT      720

TTTTCAAATT CCTCCGTCAT TTTCGGTGCT TTTCCTTCAC TGCATTCCGG GTGTGCTACT      780

ATGGAAGCCC TGTTTTTCTG TTATTGTTTT CCAAAATTGA AGCCCTTGTT TATTGCTTAT      840

GTTTGCTGGT TATGGTGGTC AACTATGTAT CTGACACACC ATTATTTTGT AGACCTTATG      900

GCAGGTTCTG TGCTGTCATA CGTTATTTTC CAGTACACAA AGTACACACA TTTACCAATT      960

GTAGATACAT CTCTTTTTTG CAGATGGTCA TACACTTCAA TTGAGAAATA CGATATATCA     1020

AAGAGTGATC CATTGGCTGC AGATTCAAAC GATATCGAAA GTGTCCCTTT GTCCAACTTG     1080

GAACTTGACT TTGATCTTAA TATGACTGAT GAACCCAGTG TAAGCCCTTC GTTATTTGAT     1140

GGATCTACTT CTGTTTCTCG TTCGTCCGCC ACGTCTATAA CGTCACTAGG TGTAAAGAGG     1200

GCTTAA                                                                1206

(2) INFORMATION FOR SEQ ID NO:34:

(i) SEQUENCE CHARACTERISTICS:
        (A) LENGTH:  30
        (B) TYPE:  nucleic acid
        (C) STRANDEDNESS:  single
        (D) TOPOLOGY:  linear (ii) MOLECULE TYPE: Other nucleic acid (synthetic DNA)
```

-continued (xi) SEQUENCE DESCRIPTION: SEQ ID NO:34:

AATATGTATA CTACATGTTT TTCAAATTCC                                30

(2) INFORMATION FOR SEQ ID NO:35:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:35:

GTTAACTCGA GAAAGTGCCC ATCAGTGTTC                                30

(2) INFORMATION FOR SEQ ID NO:36:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO:36:

GTTAACGGTA CCAGAGGAAA GAATAACGC                                 29

REGULATION OF AUREOBASIDIN SENSITIVITY IN FUNGUS

This application is a divisional of application Ser. No. 08/492,459 filed Jun. 29, 1995, now issued as U.S. Pat. No. 6,015,689, which is a continuation-in-part of now abandoned application Ser. No. 08/243,403 filed May 16, 1994.

BACKGROUND OF THE INVENTION

1. Field of the Invention

This invention relates to a protein regulating the sensitivity of fungi to an antimycotic aureobasidin and to a gene coding for this protein, namely, a gene coding for a protein regulating aureobasidin sensitivity. The present invention further relates to a series of the uses of the protein and the gene. Furthermore, it relates to an antibody against this protein and the use of the same.

In addition, this invention relates to a vector capable of imparting a novel dominant genetic marker to a host fungi, which can be integrated into the chromosome of fungal cells and by which a transformant can be easily detected from these cells inoculated into a specific medium, a process for producing a transformant having a marker imparted thereto with the use of the above mentioned vector, and a transformant transformed by this vector.

The present invention further relates to a mutant of a protein capable of imparting sensitivity of fungi to an antimycotic aureobasidin, a mutant mutated into an aureobasidin resistant protein, and a DNA coding for this protein.

2. Description of Related Art

Systemic mycoses including candidiasis have increased with an increase in immunocompromised patients in recent years due to, for example, the extended use of immunosuppressive drugs and acquired immunodeficiency syndrome (AIDS), and as opportunistic infection due to microbial substitution caused by the frequent use of widespectrum antibacterial antibiotics. Although drugs for treating mycoses such as amphotericin B, flucytosine and azole drugs (for example, fluconazole and miconazole) are now used to cope with this situation, none of them can achieve a satisfactory effect. Also, known diagnostic drugs are insufficient. For candidiasis, in particular, although there have been known several diagnostic drugs (for example, CAND-TEC for detection of candida antigen and LABOFIT for detection of D-arabinitol), none of them gives any satisfactory results in specificity or sensitivity.

The reasons for the delay in the development of remedies and diagnostic drugs for mycoses as described above are that fungi causing the mycoses are eukaryotic organisms similar to the host (i.e., man) and thus are not largely different from man and that knowledges of fungi, in particular, pathogenic fungi are insufficient. Therefore it is difficult to distinguish fungi from man or to selectively kill fungi, which is responsible for the delay in the development of drugs for mycoses.

Recently the application of genetic engineering techniques such as antisense or PCR to the treatment and diagnosis of mycoses has been expected. However known genes which are applicable thereto and/or proteins coded for by these genes are rare (PCT Pamphlet WO92/03455). Regarding pathogenic fungi, there have been cloned in recent years an acid protease gene, which has been assumed to participate in the pathogenicity of *Candida albicans* (hereinafter referred to simply as *C. albicans*) and *Candida trogicalis* (hereinafter referred to as *C. tropicalis*) causing candidiasis [B. Hube et al., J. Med. Vet. Mycol., 29, 129–132 (1991); Japanese Patent Laid-Open No. 49476/1993; and G. Togni et al., FEBS Letters, 286, 181–185 (1991)], a calmodulin gene of *C. albicans* [S. M. Saporito et al., Gene, 106, 43–49 (1991)] and a glycolytic pathway enzyme enolase gene of *C. albicans* [P. Sundstrom et al., J. Bacteriology, 174, 6789–6799 (1991)]. However, each of these genes and proteins coded for thereby is either indistinguishable from nonpathogenic fungi and eukaryotic organisms other than fungi or, if distinguishable therefrom, cannot serve as a definite action point for exhibiting any selective toxicity.

Aureobasidin [Japanese Patent Laid-Open No. 138296/1990, No. 22995/1991, No. 220199/1991 and No. 279384/1993, Japanese Patent Application No. 303177/1992, J. Antibiotics, 44 (9), 919–924, ibid., 44 (9), 925–933, ibid., 44 (11), 1187–1198 (1991)] is a cyclic depsipeptide obtained as a fermentation product of a strain *Aureobasidium pullulans* No. R106. It is completely different in structure from other antimycotics. As Tables 1 and 2 show below, aureobasidin A, which is a typical aureobasidin compound, exerts a potent antimycotic activity on various yeasts of the genus Candida including *C. albicans* which is a pathogenic fungus, *Cryptococcus neoformans, Histoplasma capsulatum, Blastomyces dermatitidis* and fungi of the genus Asperfillus (Japanese Patent Laid-Open No. 138296/1990) but has an extremely low toxicity in mammal. Thus this compound is expected to be useful as an antimycotic being excellent in selective toxicity.

Hereinafter, Candida, Cryptococcus and Aspercillus will be abbreviated respectively as C., Cr. and A.

TABLE 1

| Test strain | TIMM No. | MIC (µg/ml) |
| --- | --- | --- |
| C. albicans | 0136 | ≦0.04 |
| C. aibicans var. stellatoidea | 1308 | ≦0.04 |
| C. tropicalis | 0312 | 0.08 |
| C. kefyr | 0298 | 0.16 |
| C. parapsilosis | 0287 | 0.16 |
| C. krusei | 0270 | ≦0.04 |
| C. quilliermondii | 0257 | 0.08 |
| C. glabrata | 1062 | ≦0.04 |
| Cr. neoformans | 0354 | 0.63 |
| Cr. terreus | 0424 | 0.31 |
| Rhodotorula rubra | 0923 | 0.63 |
| A. fumigatus | 0063 | 20 |
| A. clavatus | 0056 | 0.16 |

TABLE 2

| Test strain | TIMM No. | MIC (µg/ml) |
| --- | --- | --- |
| A. nidulans | 0112 | 0.16 |
| A. terreus | 0120 | 5 |
| Penicillium commune | 1331 | 1.25 |
| Trichophyton mentagrophytes | 1189 | 10 |
| Epidermophyton floccosum | 0431 | 2.5 |
| Fonsecaea pedrosoi | 0482 | 0.31 |
| Exophiala werneckii | 1334 | 1.25 |
| Cladosporium bantianum | 0343 | 0.63 |
| Histoplasma capsulatum | 0713 | 0.16 |
| Paracoccidioides brasiliensis | 0880 | 0.31 |
| Geotrichum candidum | 0694 | 0.63 |
| Blastomyces dermatitidis | 0126 | 0.31 |

Each of the conventional antimycotics with a weak toxicity shows only a fungistatic effect, which has been regarded as a clinical problem. In contrast, aureobasidin has a fungicidal effect. From this point of view, it has been urgently required to clarify the mechanism of the selective toxicity to fungi of aureobasidin. However this mechanism still remains unknown.

There have been known techniques for introducing useful genes into monoploid fungal cells to be used in a laboratory, for example, *Saccharomyces cerevisiae* (hereinafter referred to simply as *S. cerevisiae*), *Schizosaccharomyces pombe* (hereinafter referred to simply as *Schizo. pombe*) and *Aspergillus nidulans* (hereinafter referred to simply as *A. nidulans*). Since the incorporation and fixation of plasmid DNAs into fungal cells are relatively scarcely successful, it is required to use selective markers in the identification of transformants. In the most common case, selection can be achieved by introducing an auxotrophic mutation into host cells. Examples of the mutation generally employed in, for example, *S. cerevisiae* include ura3, leu2, trp1 and his3. A plasmid carries a wild type copy of one of these genes. Since the wild type copy on the plasmid is dominant over the chromosomal allele of the host, cells having the plasmid introduced thereinto can be screened in a minimal medium which contains no nutrient required by the auxotrophic host cells. Also there have been published some reports, though in a small number, relating to the use of drug resistance in the screening of transformants. Namely, there have been reported replication vectors and chromosome integration vectors containing genes which are resistant against antibiotics such as a neomycin homologue G418, hygromycin and cerulenin. A replication vector has a DNA replication origin acting in a cell. This plasmid is held outside the chromosome as a cyclic episome and continuously reduced at a ratio of several percent with the proliferation of the cells. An integration vector is inserted into the chromosome of a host cell and thus held in a stable state. In this case, therefore, it is unnecessary to further add a drug to the medium in order to exert the selection function for maintaining the sequence of the vector.

In the case of industrial fungi, it is required to sustain the useful character, which has been imparted thereto, in a stable state. A chromosome integration vector is useful for this purpose.

Fungi have been widely applied to the production of liquors such as sake, beer and wine and fermented foods such as miso (fermented soy bean paste) and soy sauce. For breeding these fungi to be used for industrial purposes, genetic engineering techniques are also highly effective in order to impart useful characteristics thereto. Thus there have been required selective markers which are usable in efficiently screening transformants. Industrial yeasts are usually di- or polyploid cells. It is therefore difficult to introduce an auxotrophic marker, which is effective in monoploid cells of, for example, yeasts to be used in a laboratory, into these industrial yeasts. In addition, since there is a high possibility that a mutagenesis induces mutation in other genes, accordingly, it is highly difficult to create a mutant having the desired auxotrophic mutation alone introduced thereinto. The use of a drug resistance makes it possible to screen a stable transformant of an arbitrary yeast regardless of the number of chromosomes or the occurrence of specific mutation. However many of these industrial fungi are insensitive to antibiotics such as G-418 and hygromycin, which makes it impossible to use genes resistant against these antibiotics therefor. Moreover, these resistant genes are genes or proteins derived from bacteria which are procaryotes, and none of them corresponding to these genes is present in fungi such as yeasts. The use of fungal cells having these foreign genes integrated therein is seriously restricted. A cerulenin resistant gene (PDR4) originating in *S. cerevisiae* is usable in the transformation of *S. cerevisiae* including brewing yeast. However it also conferred resistances against drugs other than cerulenin, which might bring about some problems in the practical use. Therefore PDR4 cannot fully satisfy the requirements for breeding industrial fungi including *S. cerevisiae* having improved characters in the future. Thus it has been required to develop drug resistant markers with the use of genes which are inherently carried by fungi.

Under these circumstances, the present invention aims at finding a novel protein regulating aureobasidin sensitivity through the clarification of the mechanism of the selective toxicity to fungi of aureobasidin. Accordingly, the present invention aims at finding a gene coding for a protein regulating aureobasidin sensitivity, providing a process for cloning this gene and the protein regulating aureobasidin sensitivity which is encoded by this gene, further providing an antisense DNA and an antisense RNA of this gene, providing a nucleic acid probe being hybridizable with this gene, providing a process for detecting this gene with the use of the nucleic acid probe, providing a process for producing the protein regulating aureobasidin sensitivity by using this gene and providing an antibody against the protein regulating aureobasidin sensitivity, and a process for detecting the protein regulating aureobasidin sensitivity by using this antibody.

In addition, the present invention aims at providing a novel chromosome integration vector capable of imparting a novel selective marker of a drug resistance to a fungal transformant, and a transformant transformed by this vector.

The present invention further aims at providing a protein capable of imparting the aureobasidin resistance and acting as a selective marker which is usable in genetic engineering of fungi, and a DNA coding for this protein.

SUMMARY OF THE INVENTION

The present invention may be summarized as follows. Namely, the first invention of the present invention relates to an isolated gene coding for a protein regulating aureobasidin sensitivity, that is, a gene regulating aureobasidin sensitivity. The second invention relates to a process for cloning a gene regulating aureobasidin sensitivity which is characterized by using the gene regulating aureobasidin sensitivity of the first invention or a part thereof as a probe. The third invention relates to a nucleic acid probe which is hybridizable with a gene regulating aureobasidin sensitivity and comprises a sequence consisting of 15 or more bases. The fourth invention relates to an antisense DNA of a gene regulating aureobasidin sensitivity. The fifth invention relates to an antisense RNA of a gene regulating aureobasidin sensitivity. The sixth invention relates to a recombinant plasmid having a gene regulating aureobasidin sensitivity contained therein. The seventh invention relates to a transformant having the above-mentioned plasmid introduced thereinto. The eighth invention relates to a process for producing a protein regulating aureobasidin sensitivity by using the above-mentioned transformant. The ninth invention relates to an isolated protein regulating aureobasidin sensitivity. The tenth invention relates to an antibody against a protein regulating aureobasidin sensitivity. The eleventh invention relates to a process for detecting a protein regulating aureobasidin sensitivity by using the above-mentioned antibody. The twelfth invention relates to a process for detecting a gene regulating aureobasidin sensitivity by the hybridization which is characterized by using the nucleic acid probe of the third invention of the present invention. The thirteenth invention relates to a process for screening an antimycotic by using the above-mentioned transformant or a protein regulating aureobasidin sensitivity. The fourteenth invention of the present invention relates to a chromosome integration vector for a host fungus which is characterized by containing an aureobasidin resistant gene. This chromosome integration vector sometimes contains a foreign gene. The fifteenth invention relates to a process for producing an aureobasidin resistant transformant characterized by comprising:

(1) the step of obtaining a replication vector which contains an aureobasidin resistant gene, (2) the step of cleaving the aureobasidin resistant gene in the replication vector obtained in the above step at one site to give a chromosome integration vector for a host fungus;

(3) the step of integrating the chromosome integration vector for a host fungus obtained in the above step into the chromosome of the host fungus; and (4) the step of selecting a host which has been transformed into an aureobasidin resistant one in the presence of aureobasidin.

In this process for producing an aureobasidin resistant transformant, the replication vector sometimes contains a foreign gene. The sixteenth invention relates to a transformant characterized by being one obtained by the process of the fifteenth invention.

The seventeenth invention relates to a protein capable of imparting aureobasidin resistance, wherein at least the 240th amino acid residue Ala in the protein capable of imparting aureobasidin sensitivity represented by SEQ ID No. 8 in the Sequence Listing has been replaced by another amino acid residue, or another protein capable of imparting aureobasidin resistance which has an amino acid sequence obtained by subjecting the above-mentioned protein to at least one modification selected from replacement, insertion and deletion of amino acid residue(s) and shows a biological activity comparable to that of the above-mentioned protein. The eighteenth invention relates to a DNA which codes for the protein capable of imparting the aureobasidin resistance of the seventeenth invention.

As described in Japanese Patent Application No.106158/1994, the present inventors have previously found out that fungi such as Schizo. pombe and S. cerevisiae and, further, mammalian cells such as mouse lymphoma EL-4 cells, are sensitive to aureobasidin, as Table 3 shows.

TABLE 3

| Test strain or cell | MIC (µg/ml) |
| --- | --- |
| Schizo. pombe | 0.08 |
| S. cerevisiae | 0.31 |
| mouse lymphoma EL-4 | 10 |
| mouse lymphoma L5178Y | 100 |
| NRK-49F | 12.5 |

The present inventors have mutagenized a wild-type strain of Schizo. pombe or S. cerevisiae, sensitive to aureobasidin, to thereby give resistant mutants. We have further successfully isolated a gene capable of confering aureobasidin resistance (a resistant gene) from these resistant mutants and another gene capable of imparting aureobasidin sensitivity (a sensitive gene) from the corresponding sensitive cells. Furthermore, we have disclosed the existence of a protein encoded by each of these genes. By culturing cells which have been transformed by introducing the above-mentioned gene, we have succeeded in the expression of this gene. Furthermore, we have successfully found out a novel gene regulating aureobasidin sensitivity from another fungus being sensitive to aureobasidin by using a DNA fragment of the above-mentioned gene as a probe. In addition, we have clarified that the gene regulating aureobasidin sensitivity is essentially required for the growth of the cells and found out that the detection of this gene or a protein which is a gene product thereof with an antibody enables the diagnosis of diseases caused by these cells, for example, mycoses induced by fungi, and that an antisense DNA or an antisense RNA, which inhibits the expression of the gene regulating aureobasidin sensitivity being characteristic to the cells, is usable as a remedy for diseases caused by these cells, for example, mycoses induced by fungi, thus completing the present invention. The present inventors have also succeeded in the expression of this gene by preparing a replication vector containing this gene and incubating cells transformed by using this vector. By using a DNA fragment of this gene as a probe, they have further successfully found a novel gene regulating the aureobasidin sensitivity from another fungus which is sensitive to aureobasidin.

The pathogenic fungi listed in Tables 1 and 2 and fungi and mammalian cells listed in Table 3, each having a sensitivity to aureobasidin, each carries a protein regulating aureobasidin sensitivity and a gene coding for this protein. The term "a protein regulating aureobasidin sensitivity" as used herein means a protein which is contained in an organism, particularly a fungus, having a sensitivity to aureobasidin. This protein is required for the expression of the sensitivity or resistance to aureobasidin. As a matter of course, a protein having 35% or more homology with the above-mentioned protein and having a similar function is also a member of the protein regulating aureobasidin sensitivity according to the present invention. Furthermore, proteins obtained by modifying these proteins by the genetic engineering procedure are members of the protein regulating aureobasidin sensitivity according to the present invention. A gene regulating aureobasidin sensitivity means a gene which codes for such a protein regulating aureobasidin sensitivity as those described above and involves both of sensitive genes and resistant genes.

The first invention of the present invention relates to a gene regulating aureobasidin sensitivity. This gene can be isolated in the following manner. First, aureobasidin sensitive cells (a wild-type strain) are mutagenized to thereby induce a resistant strain. From chromosome DNA or cDNA of this resistant strain, a DNA library is prepared and a gene capable of confering resistance (a resistant gene) is cloned from this library. Then a DNA library of a wild strain is prepared and a DNA molecule being hybridizable with the resistant gene is isolated from this library and cloned. Thus a sensitive gene can be isolated.

The mutagenesis is performed by, for example, treating with a chemical such as ethylmethane sulfonate (EMS) or N-methyl-N'-nitro-N-nitrosoguanidine (MNNG) or by ultraviolet or other radiation. The cell that has acquired the resistance can be screened by culturing the mutagenized cells in a nutritional medium containing aureobasidin at an appropriate concentration under appropriate conditions. The resistant strain thus obtained may vary depending on the method and conditions selected for the mutagenesis. Also, strains differing in the extent of resistance from each other can be separated by changing the aureobasidin concentration or a temperature-sensitive resistant strain can be isolated by changing the temperature in the step of screening. There are a number of mechanisms of resistance to aureobasidin. Accordingly, a number of resistant genes can be isolated by genetically classifying these various resistant strains. In the case of a yeast, the classification may be performed by the complementation test. Namely, resistant strains are prepared from haploid cells. Next, diploid cells can be obtained by crossing resistant strains differing in mating type from each other. Then spores formed from these diploids are examined by the tetrad analysis.

As typical examples of the genes regulating aureobasidin sensitivity(named aur) according to the present invention, aur1 and aur2 genes may be cited. Typical examples of the aur1 gene include spaur1 gene isolated from *Schizo. pombe* and scaur1 gene isolated from *S. cerevisiae*, while typical examples of the aur2 gene include scaur2 gene isolated from *S. cerevisiae*. Now, resistant genes (spaur1$^R$, scaur1$^R$ and scaur2$^R$) isolated from resistant mutants by the present inventors and sensitive genes (spaur1$^S$, scaur1$^S$ and scaur2$^S$) isolated from sensitive wild-type strains will be described.

FIG. 1 shows a restriction enzyme map of the genes spaur1$^R$ and spaur1$^S$ regulating aureobasidin sensitivity, FIG. 2 shows a restriction enzyme map of scaur1$^R$ and scaur1$^S$ and FIG. 3 shows a restriction enzyme map of scaur2$^R$ and scaur2$^S$.

*Schizo. pombe*, which is sensitive to aureobasidin, is mutagenized with EMS and a genomic library of the resistant stain thus obtained is prepared. From this library, a DNA fragment containing a resistant gene (spaur1$^R$) and having the restriction enzyme map of FIG. 1 is isolated. This gene has a nucleotide sequence represented by SEQ ID No. 1 in Sequence Listing. The amino acid sequence of a protein encoded by this gene, which is estimated on the basis of this nucleotide sequence, is the one represented by SEQ ID No. 2 in Sequence Listing. By the hybridization with the use of this resistant gene as a probe, a DNA fragment containing a sensitive gene (spaur1$^S$) and having the restriction enzyme map of FIG. 1 is isolated from a sensitive strain. This gene has a nucleotide sequence represented by SEQ ID No. 3 in Sequence Listing. The amino acid sequence of a protein encoded by this gene, which is estimated on the basis of this nucleotide sequence, is the one represented by SEQ ID No. 4 in Sequence Listing. A comparison between the sequences of SEQ ID No. 3 and SEQ ID No. 1 reveals that a mutation from G to T occurs at the base at the position 1053, while a comparison between the sequences of SEQ ID No. 4 and SEQ ID No. 2 reveals that glycine at the residue 240 is converted into cysteine at the amino acid level, thus giving rise to the resistance.

Also, *S. cerevisiae*, which is sensitive to aureobasidin, is mutagenized with EMS and genomic libraries of two resistant strains thus obtained are prepared. From one of these libraries, a DNA fragment containing a resistant gene (scaur1$^R$) as a dominant mutant and having the restriction enzyme map of FIG. 2 is isolated, while a DNA fragment containing a resistant gene (scaur2$^R$) and having the restriction enzyme map of FIG. 3 is isolated from another library.

The nucleotide sequence of the coding region for the protein of the scaur1$^R$ gene is the one represented by SEQ ID No. 5 in Sequence Listing. The amino acid sequence of the protein encoded by this gene, which is estimated on the basis of the above nucleotide sequence, is the one represented by SEQ ID No. 6 in Sequence Listing. By the hybridization with the use of this resistant gene scaur1$^R$ as a probe, a DNA fragment containing a sensitive gene (scaur1$^S$) and having the restriction enzyme map of FIG. 2 is isolated from a sensitive strain. This gene has a nucleotide sequence represented by SEQ ID No. 7 in Sequence Listing. The amino acid sequence of a protein encoded by this gene, which is estimated on the basis of this nucleotide sequence, is the one represented by SEQ ID No. 8 in Sequence Listing. A comparison between the sequences of SEQ ID No. 7 and SEQ ID No. 5 reveals that a mutation from T to A occurs at the base at the position 852, while a comparison between the sequences of SEQ ID No. 8 and SEQ ID No. 6 reveals that phenylalanine at the residue 158 is converted into tyrosine at the amino acid level, thus giving rise to the resistance. The spaur1 gene has a 58% homology with the scaur1 gene at the amino acid level. Thus it is obvious that they are genes coding for proteins having similar functions to each other. When genes and proteins being homologous in sequence with the spaur1 and scaur1 genes and with the proteins encoded thereby are searched from a data base, none having a homology of 35% or above is detected. Accordingly, it is clear that these genes and the proteins encoded thereby are novel molecules which have never been known hitherto.

By the hybridization with the use of the DNA fragment of the resistant gene scaur2$^R$ as a probe, a DNA fragment containing a sensitive gene (scaur2$^S$) and having the restriction enzyme map of FIG. 3 is isolated from a sensitive strain.

The nucleotide sequence of this sensitive gene is the one represented by SEQ ID No. 9 in Sequence Listing and the amino acid sequence of the protein encoded by this gene, which is estimated on the basis of this nucleotide sequence, is the one represented by SEQ ID No. 10 in Sequence Listing. As the result of the homology search with the scaur2$^S$ gene and the protein encoded thereby, it has been found out that cystic fibrosis transmembrane conductance regulator (CFTR) of mammals alone has a homology as low as 31%. Compared with this CFTR, however, the part having a high homology is limited to the region around the domain of the nucleotide binding. It is therefore obvious that the protein encoded by the scaur2$^S$ gene is a protein which is completely different from CFTR in function and has never been known hitherto.

In order to prove the importance of the aur1 gene in the growth of cells, genes for disrupting the aur1 as shown in FIG. 4 and FIG. 5, in which genes coding for orotidine-5'-phosphate decarboxylase (ura4+ in the case of *Schizo. pombe*, while URA3 in the case of *S. cerevisiae*) have been introduced midway in the aur1 gene, are prepared. When these aur1 disrupted genes are introduced into *Schizo. pombe* and *S. cerevisiae* respectively, the cells having the aur1 disrupted genes cannot grow at all. Thus it has been revealed that these genes and the proteins encoded thereby are essentially required for the growth of the yeast cells.

As the above examples clearly show, a gene regulating aureobasidin sensitivity can be isolated by using a organism having sensitivity to aureobasidin as a starting material and by carrying out the cloning with the use of various mutagenesis methods and/or screening methods depending on the organisms or the methods. Also, genes being hybridizable with the above-mentioned genes are involved in the scope of the first invention of the present invention. A gene regulating aureobasidin sensitivity can be isolated by the following method. The genomic DNA library of an organism having sensitivity to aureobasidin is integrated into, for example, a high-expression vector of a yeast and transformed into the yeast. Then a clone having aureobasidin resistance is selected from the transformants and DNA is recovered from this clone. Thus the resistant gene can be obtained. As a matter of course, genes obtained by modifying some part of the gene regulating aureobasidin sensitivity thus obtained by some chemical or physical methods are involved in the scope of the first invention of the present invention.

The second invention of the present invention relates to a process for cloning a gene regulating aureobasidin sensitivity which is characterized by using the gene regulating aureobasidin sensitivity of the first invention of the present invention or a part thereof as a probe. Namely, by screening by the hybridization method or the polymerase chain reaction (PCR) method with the use of a part (consisting of at least 15 oligonucleotides) or the whole of the gene as obtained above, a gene coding for a protein having a similar function can be isolated.

For example, a pair of primers of SEQ ID No. 11 and SEQ ID No. 12 in Sequence Listing are synthesized on the basis of the DNA nucleotide sequence of the spaur1$^R$ gene represented by SEQ ID No. 1. Then PCR is performed by using cDNA of *C. albicans*, which is a pathogenic fungus, as a template with the use of the above-mentioned primers. The PCR is carried out and the PCR products are electrophoresed on an agarose gel and stained with ethidium bromide. In FIG. 6, the lanes 1, 2 and 3 show the results obtained by using cDNA of *C. albicans*, cDNA of *S. cerevisiae* and cDNA of *Schizo. pombe* as a template, respectively. As shown in FIG. 6, a certain DNA fragment is specifically amplified.

By screening the genomic DNA library of *C. albicans* with the use of this DNA fragment as a probe, a DNA molecule having a gene (caaur1), which has the same function as that of the spaur1 and scaur1 genes and having the restriction enzyme map of FIG. 7 is obtained. The nucleotide sequence of this caaur1 gene is the one represented by SEQ ID No. 13 in Sequence Listing and the amino acid sequence of the protein encoded by this gene, which has been estimated on the basis of the above nucleotide sequence, is the one represented by SEQ ID No. 14 in Sequence Listing. It has a high homology with the proteins encoded by the spaur1 and scaur1 genes.

By screening the genomic DNA library of *C. albicans* with the use of a DNA fragment comprising the whole length or a part of the scaur2$^S$ gene represented by SEQ ID No. 9 in Sequence Listing as a probe, a DNA fragment containing gene (caaur2), which has the same function as that of the scaur2 gene, and having the restriction enzyme map of FIG. 8 is obtained. The nucleotide sequence of a part of this caaur2 gene is the one represented by SEQ ID No. 15 in Sequence Listing and the amino acid sequence of the region encoded by this gene, which has been estimated on the basis of this nucleotide sequence, is the one represented by SEQ ID No. 16 in Sequence Listing. It has a high homology with the corresponding region of the protein encoded by the scaur2 gene.

The third invention of the present invention relates to an oligonucleotide comprising 15 or more bases which serves as the above-mentioned nucleic acid probe and is hybridizable with the gene regulating aureobasidin sensitivity, for example, the DNA fragment having the restriction enzyme map as shown in FIG. 1, FIG. 2 or FIG. 3. This nucleic acid probe is usable in, for example, the hybridization in situ, the identification of a tissue wherein the above-mentioned gene can be expressed, and the confirmation of the presence of a gene or mRNA in various vital tissues. This nucleic acid probe can be prepared by ligating the above-mentioned gene or a gene fragment to an appropriate vector, introducing it into a bacterium, allowing it to replicate in the bacterium, extracting from a disrupted cell suspension, cleaving with a restriction enzyme capable of recognizing the vector-ligating site, electrophoresing and then excising from the gel. Alternatively, this nucleic acid probe can be constructed by the chemical synthesis with the use of a DNA synthesizer or gene amplification techniques by PCR on the basis of the nucleotide sequence of SEQ ID. Nos. 1, 3, 5, 7, 9, 13, 15 or 21 in Sequence Listing. This nucleic acid probe can be labeled with a radioisotope or a fluorescent substance to thereby elevate the detection sensitivity during use.

The fourth invention of the present invention relates to an antisense DNA of the above-mentioned gene regulating aureobasidin sensitivity, while the fifth invention of the present invention relates to an antisense RNA thereof. The introduction of the antisense DNA or antisense RNA into cells makes it possible to control the expression of the gene regulating aureobasidin sensitivity.

As examples of the antisense DNA to be introduced, antisense DNAs corresponding to the genes regulating aureobasidin sensitivity of SEQ ID Nos. 1, 3, 5, 7, 9, 13, 15 or 21 in Sequence Listing and some parts thereof may be cited. SEQ ID No. 17 in Sequence Listing shows an example of this antisense DNA. It represents the sequence of an antisense DNA of the gene regulating aureobasidin sensitivity of SEQ ID No. 1 in Sequence Listing. A fragment obtained by appropriately cleaving some part of such an antisense DNA, and a DNA synthesized depending on such an antisense DNA sequence may be used as the antisense DNA.

As examples of the antisense RNA to be introduced, antisense RNAs corresponding to the genes regulating aureobasidin sensitivity of SEQ ID Nos. 1, 3, 5, 7, 9, 13, 15 or 21 in Sequence Listing and some parts thereof may be cited. SEQ ID No. 18 in Sequence Listing shows an example of this antisense RNA. It represents the sequence of an antisense RNA of the gene regulating aureobasidin sensitivity of SEQ ID No. 1 in Sequence Listing. A fragment obtained by appropriately cleaving some part of such an antisense RNA, an RNA synthesized depending on such an antisense RNA sequence, and an RNA prepared with RNA polymerase in an in vitro transcription system by using the DNA corresponding to the gene regulating aureobasidin sensitivity of SEQ ID No. 1 or SEQ ID No. 3 in Sequence Listing or a part thereof may be used as the antisense RNA.

These antisense DNA and antisense RNA may be chemically modified so as to prevent degradation in vivo or to facilitate passage through a cell membrane. A substance capable of inactivating mRNA, for example, ribozyme may be linked thereto. The antisense DNA and antisense RNA thus prepared are usable in the treatment of various diseases such as mycoses accompanied by an increase in the amount of mRNA coding for a protein regulating aureobasidin sensitivity.

The sixth invention of the present invention relates to a recombinant plasmid having a gene coding for a protein regulating aureobasidin sensitivity being integrated into an appropriate vector. For example, a plasmid, in which a gene regulating aureobasidin sensitivity gene has been integrated into an appropriate yeast vector, is highly useful as a selection marker gene, since a transformant can be easily selected thereby with the guidance of the chemical resistance by using aureobasidin.

Also, the recombinant plasmid can be stably carried by, for example, *Escherichia coli*. Examples of vectors which are usable in this case include pUC118, pWH5, pAU-PS, Traplex119 and pTV118. PAU-PS having the spaur1$^S$ gene integrated therein is named pSPAR1. pWH5 having the spaur1$^S$ gene integrated therein is named pSCAR1. pWH5 having the scaur2$^R$ gene integrated therein is named pSCAR$^2$. Traplexll9 vector having the caaur1 gene integrated therein is named pCAAR1. pTV118 vector having a part of the caaur2 gene integrated therein is named pCAAR2N. Each of these recombinant plasmids is transformed into *E. coli*. It is also possible to express these plasmids in an appropriate host. Such a gene is reduced exclusively into the open reading frame (ORF) to be translated into a protein by cleaving with an appropriate restriction enzyme, if necessary, and then bound to an appropriate vector. Thus an expression recombinant plasmid can be obtained. When *E. coli* is used as the host, plasmids such as pTV118 may be used as a vector for the expression plasmid. When a yeast is used as the host, plasmids such as pYES2 may be used as the vector. When mammalian cells are used as the host, plasmids such as pMAMneo may be used as the vector.

The seventh invention of the present invention relates to a transformant having the above-mentioned recombinant plasmid which has been introduced into an appropriate host. As the host, *E. coli*, yeasts and mammalian cells are usable. *E. coli* JM109 transformed by PSPAR1 having the spaur1$^S$ gene integrated therein has been named and designated as *Escherichia coli* JM109/pSPAR1 and deposited at National Institute of Bioscience and Human-Technology, Agency of Industrial Science and Technology (1–3, Higashi 1 chome Tsukuba-shi Ibaraki-ken 305, JAPAN), in accordance with the Budapest Treaty under the accession number FERM BP-4485. *E. coli* HB101 transformed by pSCAR1 having the scaur1$^S$ gene integrated therein has been named and designated as *Escherichia coli* HB101/pSCAR1 and deposited at National Institute of Bioscience and Human-Technology, Agency of Industrial Science and Technology in accordance with the Budapest Treaty under the accession number FERM BP-4483. *E. coli* HB101 transformed by pSCAR2 having the scaur2$^R$ gene integrated therein has been named and designated as *Escherichia coli* HB101/pSCAR2 and deposited at National Institute of Bioscience and Human-Technology, Agency of Industrial Science and Technology in accordance with the Budapest Treaty under the accession number FERM BP-4484. *E. coli* HB101 transformed by pCAAR1 having the caaur1$^S$ gene integrated therein has been named and designated as Escherichia coli HB101/pCAAR1 and deposited at National Institute of Bioscience and Human-Technology, Agency of Industrial Science and Technology in accordance with the Budapest Treaty under the accession number FERM BP-4482. *E. coli* HB101 transformed by pCAAR2N having a part of the caaur2 gene integrated therein has been named and designated as *Escherichia coli* HB101/pCAAR2N and deposited at National Institute of Bioscience and Human-Technology, Agency of Industrial Science and Technology in accordance with the Budapest Treaty under the accession number FERM BP-4481.

A transformant capable of expressing a protein regulating aureobasidin sensitivity can be obtained by transforming a expression recombinant plasmid into an appropriate host, as described above. For example, a yeast having a recombinant plasmid as shown in FIG. 9 introduced thereinto is usable for this purpose.

The eighth invention of the present invention relates to a process for producing a protein regulating aureobasidin sensitivity which comprises incubating a transformant according to the sixth invention of the present invention, which contains a gene coding for this protein, in an appropriate nutritional medium, allowing the expression of the protein, then recovering the protein from the cells or the medium and purifying the same. For the expression of the gene coding for this protein, *E. coli*, a yeast or mammalian cells are employed as a host. When the yeast having the recombinant plasmid of FIG. 9 is incubated in a medium containing galactose, for example, the protein regulating aureobasidin sensitivity which is encoded by the scaur1$^S$ gene can be expressed.

The ninth invention of the present invention relates to an isolated protein regulating aureobasidin sensitivity. As examples of such a protein, those encoded by the above-mentioned spaur1, scaur1, scaur2, caaur1 and caaur2 genes can be cited.

The spaur1$^S$ gene codes for a protein having an amino acid sequence represented by SEQ ID No. 4 in Sequence Listing, while the scaur1$^S$ gene codes for a protein having an amino acid sequence represented by SEQ ID No. 8 in Sequence Listing. By the northern hybridization with the use of a DNA fragment of the spaur1 gene as a probe, mRNAs are detected from a sensitive strain (FIG. 10). Thus the expression of the spaur1 gene is confirmed.

FIG. 10 is an autoradiogram showing the results of the northern hybridization wherein mRNAs obtained from cells of a sensitive strain of *Schizo. pombe* in the logarithmic growth phase (lane 1), cells of a resistant strain in the logarithmic growth phase (lane 2), cells of the sensitive strain in the stationary phase (lane 3) and cells of the resistant strain in the stationary phase (lane 4) are electrophoresed on a 1.2% agarose gel containing formaldehyde.

The tenth invention of the present invention relates to an antibody against the above-mentioned protein regulating aureobasidin sensitivity. For example proteins having amino acid sequences of SEQ ID Nos. 2, 4, 6, 8, 10, 14, 16 or 22 in Sequence Listing and peptides comprising some parts of these amino acid sequences may be used as an antigen. The former antigens can be prepared through the expression in a transformant followed by purification, while the latter antigens can be synthesized on, for example, a marketed synthesizer. The antibody is produced by the conventional method. For example, an animal such as a rabbit is immunized with the above-mentioned protein or a peptide fragment together with an adjuvant to thereby give a polyclonal antibody. A monoclonal antibody can be produced by fusing antibody-producing B cells, which have been obtained by immunizing with an antigen, with myeloma cells, screening hybridomas producing the target antibody, and incubating these cells. As will be described hereinafter, these antibodies are usable in the treatment and diagnosis for animal and human diseases in which the above-mentioned proteins participate, such as mycoses.

For example, a peptide corresponding to the part of the 103- to 113-positions in the amino acid sequence of SEQ ID No. 8 is synthesized on a synthesizer and then bound to a carrier protein. Then a rabbit is immunized therewith and thus a polyclonal antibody is obtained. In the present invention, keyhole limpet hemocyanin (KLH) is used as the carrier protein. Alternatively, bovine serum albumin and ovalbumin are usable therefor.

The eleventh invention of the present invention relates to a process for detecting a protein regulating aureobasidin sensitivity by using the above-mentioned antibody. The detection can be carried is out by detecting the binding of the antibody to the protein or measuring the amount of binding. For example, the protein or the cells producing the same can be detected by treating with a fluorescence-labeled antibody and then observing under a fluorescence microscope. The amount of the antibody bound to the protein can be measured by various known methods. For example, *S. cerevisiae* cells are stained by the immunofluorescent antibody technique by using the above-mentioned antibody and a secondary antibody such as FITC-labeled anti-rabbit antibody. Thus it is clarified that the protein encoded by the scaur1 gene is distributed all over the cells. Further, a yeast having the recombinant plasmid of FIG. 9 introduced thereinto is incubated in a medium containing glucose or galactose. The cells thus obtained are disrupted with glass beads and proteins are solubilized. Then these proteins are separated by SDS-polyacrylamide gel electrophoresis (SDS-PAGE) and the western blotting is carried out in the conventional manner by using the above-mentioned polyclonal antibody and peroxidase-labeled anti-rabbit antibody. Consequently, the protein encoded by the scaur1 gene can be detected, as FIG. 11 shows.

FIG. 11 shows the results of the western blotting wherein the proteins prepared from the cells obtained by the incubation in the presence of glucose (lane 1) or galactose (lane 2) are subjected to SDS-PAGE. A main band binding to the polyclonal antibody of the present invention is detected at around 38 kDa.

The twelfth invention of the present invention relates to a process for detecting a gene regulating aureobasidin sensitivity, for example, mRNA at the expression of a protein, by using the above-mentioned oligonucleotide as a nucleic acid probe. This process is applicable to the diagnosis for various diseases, including mycoses, associated with an abnormal amount of mRNA coding for the protein. For example, nucleic acids are precipitated from disrupted cells and mRNA is hybridized with a radioisotope-labeled nucleic acid probe on a nitrocellulose membrane. The amount of binding can be measured by autoradiography (FIG. 10) or with a scintillation counter.

The thirteenth invention of the present invention relates to a process for efficient screening of a novel antimycotic by using the transformant of the seventh invention of the present invention or the protein regulating aureobasidin sensitivity of the ninth invention of the present invention. For example, a drug exerting its effect on the protein or the gene of the present invention can be efficiently found out through a comparison of the activity on a transformant containing a sensitive gene with the activity on a transformant containing a resistant gene or a comparison between the activities on transformants differing in expression level from each other. Also, the screening can be efficiently carried out by measuring the affinity for the protein of the present invention, for example, the activity of inhibiting the binding of radiolabeled-aureobasidin to the protein.

As the above-mentioned examples clearly show, a gene regulating the aureobasidin sensitivity corresponding to each organism or each method can be isolated by employing a starting material, which is an organism having the sensitivity to aureobasidin, and effecting cloning by conducting various mutagenesis and/or screening treatments in the same manner as the one described above. Moreover, genes hybridizable with these genes can be isolated. As a matter of course, it is possible to prepare modified genes by partly altering the genes regulating the aureobasidin sensitivity obtained above by chemical, physical or genetic engineering techniques.

In the present invention, an aureobasidin resistant gene refers to a gene which is capable of imparting the resistance to an antimycotic aureobasidin when integrated into a host fungus. This gene codes for a protein imparting an aureobasidin resistance.

The aureobasidin resistant gene is exemplified typically by the above-mentioned spaur1$^R$ and scaur1$^R$. Such a gene acts predominantly and the resistance conferred by this gene is selective to aureobasidin. That is to say, it does not cause any substantial change in the sensitivity to other drugs.

The aureobasidin resistant gene also involves genes which are hybridizable with spaur1$^R$ and scaur1$^R$ and impart the aureobasidin resistance to a host fungus (for example, genes prepared by partly altering the spaur1$^R$ or scaur1$^R$ gene by chemical, enzymatic, physical or genetic engineering techniques).

Furthermore, the aureobasidin resistant gene involves a gene coding for a protein, which has an amino acid sequence obtained by subjecting a protein (Aur1$^R$p) capable of imparting the aureobasidin resistance to at least one modification selected from replacement, insertion and deletion of amino acid residue(s) and shows the activity of imparting the aureobasidin resistance.

The replacement, insertion and deletion of amino acid residue(s) from Aur1$^R$p can be effected by a site-specific mutagenesis. A DNA coding for the isolated Aur1$^R$p or a DNA coding for the protein capable of imparting the aureobasidin sensitivity (Aur1$^S$p) can be easily modified by effecting at least one of the replacement, insertion and deletion of nucleotide(s) and thus a novel DNA coding for a mutant of Aur1$^R$p can be obtained. Regarding the replacement, insertion and deletion of amino acid residue(s), the conversion of the amino acid(s) is based on one which can be effected by genetic engineering techniques without deteriorating the biological activity. In order to appropriately effect the mutation on the residue at a specific site, the target codon is subjected to random mutagenesis and a mutant having the desired activity is screened from the ones thus expressed. The mutant obtained by insertion involves a fused protein wherein Aur1$^R$p or its fragment is bound to another protein or polypeptide at the amino terminal and/or the carboxyl terminal of the Aur1$^R$p or its fragment via a peptide bond. In order to delete amino acid residue(s), it is also possible to replace an arbitrary amino acid codon in the amino acid sequence with a termination codon by the gapped duplex method to thereby delete the region on the carboxyl terminal side of the replaced amino acid residue from the amino acid sequence. Alternatively, a DNA coding for a protein, from which the amino terminal and/or carboxyl terminal regions in an arbitrary length have been deleted, can be obtained by the deletion method comprising degrading the coding DNA from the region(s) corresponding to the amino terminal and/or the carboxyl terminal of the amino acid sequence [*Gene*, 33, 103–119 (1985)] or a PCR method with the use of primers containing an initiation codon and/or a termination codon. Known examples of the site-specific mutagenesis method include the gapped duplex method with the use of oligonucleotide(s) [*Methods in Enzymology*, 154, 350–367 (1987)], the uracil DNA method with the use of oligonucleotide(s) [*Methods in Enzymoloay*, 154, 367–382 (1987)], the nitrous acid mutation method [*Proc. Natl. Acad. Sci. USA*, 79, 7258–7262 (1982)] and the cassette mutation method [*Gene*, 34, 315–323 (1985)].

The present inventors have found out that Aur1$^S$p represented by SEQ ID No. 8 in the Sequence Listing can be converted into Aur1$^R$p by replacing the 240th residue Ala by another amino acid residue, thus completing the seventeenth and eighteenth inventions.

The Aur1$^R$p of the seventeenth invention is one wherein the 240th residue Ala of Aur1$^S$p represented by SEQ ID No. 8 in the Sequence Listing has been replaced by another amino acid residue. Other amino acid residues may be replaced, inserted or deleted by using chemical, physical or genetic engineering techniques, so long as the biological activity is not deteriorated thereby. The Aur1$^R$p of the seventeenth invention may be appropriately prepared through genetic engineering techniques by using a DNA coding for Aur1$^S$p represented by SEQ ID No. 33 in the Sequence Listing. Its biological activity can be assayed by measuring the activity of converting aureobasidin sensitive cells into resistant cells. The Aur1$^S$p of the seventeenth invention is one having an enhanced activity of converting aureobasidin sensitive cells into resistant cells compared with Aur1$^R$p represented by SEQ ID No. 6 in the Sequence Listing.

A preferable Aur1$^R$p is one having an enhanced activity of converting aureobasidin sensitive cells into resistant cells compared with Aur1$^R$p represented by SEQ ID No. 6 in the Sequence Listing. A DNA coding for this Aur1$^R$p can be appropriately used in the present invention.

In an example of particularly preferable embodiment of Aur1$^R$p, a mutant can be obtained by replacing the 240th residue Ala by Cys. The amino acid sequence of an example of such a mutant is shown in SEQ ID No. 28 in the Sequence Listing. This mutant is referred to as Aur1$^R$p (A240C). It is also possible to obtain a mutant wherein the 158th residue Phe and the 240th residue Ala of Aur1$^S$p have been replaced respectively by Tyr and Cys. The amino acid sequence of this mutant is shown in SEQ ID No. 29 in the Sequence Listing. This mutant is referred to as Aur1$^R$p (F158Y, A240C). Each of these mutants has a stronger ability to impart aureobasidin resistance than that of the protein represented by SEQ ID No. 26 in the Sequence Listing [Aur1$^R$p (F158Y)] wherein the 158th residue Phe of Aur1$^S$p has been replaced by Tyr.

The aureobasidin resistant gene to be used in the present invention is exemplified by the DNAs represented by SEQ ID Nos. 30 to 32 in the Sequence Listing. The DNA represented by SEQ ID No. 32 in the Sequence Listing is one coding for Aur1$^R$p (F158Y), the DNA represented by SEQ ID No. 30 in the Sequence Listing is one coding for Aur1$^R$p (A240C), and the DNA represented by SEQ ID No. 31 in the Sequence Listing is one coding for Aur1$^R$p (F158Y, A240C).

A replication plasmid can be prepared by integrating a gene, which coded for a protein regulating the aureobasidin sensitivity, into an appropriate vector. For example, a plasmid prepared by integrating an aureobasidin resistant gene into an appropriated yeast vector is highly useful as a selective marker gene, since a transformant can be easily selected thereby depending on the drug resistance with the use of aureobasidin. As the vector for yeasts, use can be made of ones of YR$_p$, YC$_p$, YE$_p$ and YI$_p$ types.

Also, the replication plasmid can be stably carried by, for example, *Escherichia coli*, as described above. Examples of vectors which are usable in this case include pUC118, pWH5, pAU-PS, Traplex119 and pTV118.

The integration vector containing the aureobasidin resistant gene of the present invention is a linear vector which can be usually prepared by cleaving a replication plasmid containing the aureobasidin resistant gene into a linear form. The cleavage point in the replication plasmid will be described hereinbelow.

FIG. 13 shows a process wherein an aureobasidin resistant gene in a chromosome integration vector undergoes homologous recombination with the host chromosome being homologous therewith (i.e., an aureobasidin sensitive gene) and thus aureobasidin sensitive cells are converted into aureobasidin resistant cells. A replication plasmid containing the aureobasidin resistant gene is cleaved into a linear form at one position in the aureobasidin resistant gene sequence with an appropriate restriction enzyme. The vector thus linearized undergoes homologous recombination with the aureobasidin sensitive gene in the host chromosome being homologous therewith. Thus the aureobasidin resistance is imparted to the host cells. When the replication plasmid contains a foreign gene, then the aureobasidin resistance and the foreign gene are imparted to the host cells. For example, a replication vector pAUR1aare for preparing a linear vector, which contains scaur1$^R$ and human acylamino acid releasing enzyme (AARE) described in Japanese Patent Laid-Open No. 254680/1991, is prepared. *Escherichia coli* JM109 strain having this vector introduced therein was named and indicated as *Escherichia coli* JM109/pAUR1aare and has been deposited at National Institute of Bioscience and Human-Technology, Agency of Industrial Science and Technology under the accession number FERM P-14366. To linearize a replication vector, use can be effectively made of a restriction enzyme cleavage site which exists not in the target foreign gene moiety but in the aureobasidin resistant gene. In the cases of, for example, scaur1$^R$ originating in *S. cerevisiae* and spaur1$^R$ originating in *Schizo. pombe*, restriction enzyme sites of StuI, etc. and BalI, etc. are usable respectively.

In a preferable form, the vector of the present invention may contain an aureobasidin resistant gene and a foreign gene and other genes originating in replication vectors may be eliminated therefrom. Promoters, terminators, etc. for expressing the aureobasidin resistant gene and the foreign gene may be selected depending on the characters of the host. As a matter of course, the promoter parts of the DNAs represented by SEQ ID Nos. 1 and 5 in the Sequence Listing can be used as a promoter for expressing the function of the aureobasidin resistant gene. In the case of *S. cerevisiae*, use can be made of, for example, promoters of alcohol dehydrogenase gene (ADH1) and glyceraldehyde-3-phosphate dehydrogenase gene (GPD) and the terminator of cytochrome C1 gene (CYC1). These promoters and terminators may be different from those for expressing the aureobasidin resistant gene.

In the present invention, the term "foreign gene" refers to a gene which is foreign to the host fungal cells, i.e., an alien gene. Examples thereof include a nonfungal gene, a modified gene, a gene of a fungal species different from the host and a self-cloned gene. More particularly, genes participating in fermentation, alcohol resistance, saccharification and the formation of taste components or aroma components fall within this category.

The fifteenth invention relates to a process for producing an aureobasidin resistant transformant. An aureobasidin resistant transformant can be created by, for example, preparing a replication vector containing the above-mentioned aureobasidin resistant gene, cleaving it at one position in the aureobasidin resistant gene in the replication vector to give a linear chromosome integration vector for a host fungus, adding this vector to aureobasidin sensitive host fungal cells under such conditions as to allow the transformation of the fungal cells, thus integrating the vector into the host chromosome, incubating the transformant in a medium suitable for the proliferation of the host cells containing the antibiotic aureobasidin, and screening the aureobasidin resistant transformant thus proliferating. The transformation may be effected in accordance with publicly known methods such as the protoplast generation procedure, the lithium acetate procedure or the electroporation procedure. The medium to be used herein is not particularly restricted, so long as it is usable in the proliferation of fungi. Examples of such a medium commonly employed include Sabouraud's dextrose medium, a YPD medium, a czapek medium and a YNBG medium. The concentration of the aureobasidin added varies depending on the host fungal cells having the sensitivity and usually ranges from 0.05 to 80 μg/ml.

The transformant of the sixteenth invention can be obtained by the process of the fifteenth invention.

As an example of the transformant according to the present invention, Sake yeast Kyokai K-701 having scaur1$^R$ and AARE gene integrated into the chromosome has been deposited at National Institute of Bioscience and Human-Technology, Agency of Industrial Science and Technology under the accession number FERM P-1437. The transformant thus obtained by using the chromosome integration vector of the present invention has an aureobasidin resistance imparted thereto and the foreign gene integrated thereinto which is held on the chromosome in a stable state. These characteristics make it highly useful in industrial uses, etc.

The Aurl$^R$p of the seventeenth invention can impart the aureobasidin resistance to monoploid yeasts and diploid yeasts, in particular, practically usable ones. Namely, it is highly useful in breeding *S. cerevisiae* which has been widely applied to liquors such as sake, shochu, beer and wine and fermented foods such as bread. Further, the Aurl$^R$p of the seventeenth invention is applicable to fungi other than *S. cerevisiae* and useful in, for example, breeding and genetic engineering application of other fungi.

For example, the Aurl$^R$p of the seventeenth invention is capable of imparting the aureobasidin resistance to *C. albicans*. A vector having the DNA coding for this Aurl$^R$p is the first vector for genetic engineering uses provided for *C. albicans*.

It is known that *C. albicans* is a fungus causative of mycosis. With the recent increase in opportunistic infection, it has been needed to conduct studies for clarifying the causes of the pathogenicity. The Aurl$^R$p of the seventeenth invention and the above-mentioned vector are highly useful in genetic studies on *C. albicans*.

Figure 1:
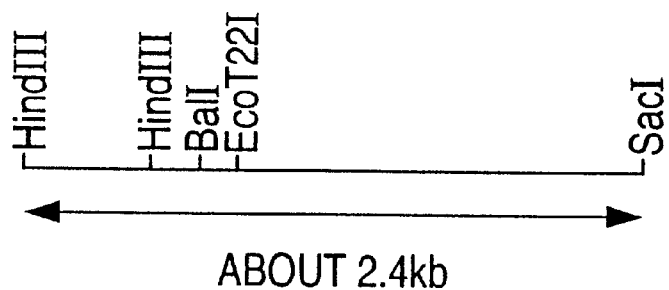
FIG. 1 is a restriction enzyme map of the genes spaurl$^R$ and spaurl$^S$ regulating aureobasidin sensitivity.

To further illustrate the present invention in greater detail, the following Examples will be given. However it is to be understood that the present invention is not restricted thereto.

DESCRIPTION OF THE PREFERRED EMBODIMENTS

EXAMPLE 1

Cloning of a Gene Regulating Aureobasidin Sensitivity Originating in Fission Yeast *Schizo. pombe*

1-a) Separation of aureobasidin-resistant mutant of *Schizo. pombe*

About 1×10$^8$ cells of a *Schizo. pombe* haploid cell strain JY745 (mating type h$^-$, genotype ade6-M210, leu1, ura4-D18) exhibiting a sensitivity to aureobasidin at a concentration of 0.08 μg/ml were suspended in 1 ml of a phosphate buffer containing 0.9% NaCl. Then the cells were mutagenized with EMS at a final concentration of 3% at 30° C. for 90 minutes. After neutralizing by adding 8 ml of 5% sodium thiosulfate, the cells thus treated were harvested by centrifugation (2500 r.p.m., 5 minutes), washed twice with 6 ml of physiological saline and then suspended in 2 ml of a YEL medium (3% of glucose, 0.5% of yeast extract). The suspension was incubated at 30° C. for 5 hours under stirring and then spreaded on a YEA plate (the YEL medium containing 1.5% of agar) containing 5 μg/ml of aureobasidin A. After incubating at 30° C. for 3 to 4 days, two or three aureobasidin-resistant colonies were formed per 1×10$^8$ cells. After carrying out the mutagenesis several times, five clone mutants, i.e., THR01, THR04, THR05, THR06 and THR07 were obtained. These mutants were resistant to more than 25 μg/ml of aureobasidin A but the same as the parent strain in the sensitivity to cycloheximide and amphotericin B. Therefore it is estimated that they are not mutants having a multiple drug resistance but ones having a resistance specific to aureobasidin. 1-b) Genetic analysis Each of the above-mentioned resistant strains THR01, THR04, THR05, THR06 and THR07 was crossed with normal cells of *Schizo. pombe* LH121 strain (mating type h$^+$, genotype ade6-M216, ura4-D18) differing in mating type. Diploid cells obtained were examined about the resistance to aureobasidin. Similar to the resistant strains, the five diploids formed by crossing the resistant strains with the normal one were resistant to 25 μg/ml of aureobasidin A, thus proving that these resistant mutations were dominant. To perform the tetrad analysis, the above-mentioned diploids were subsequently inoculated on an MEA medium (3% of malt extract, 2.5% of agar) for sporulation and incubated at 25° C. for 2 days. Prior to the meiosis, the diploid cells replicated DNA on the MEA medium and then underwent the meiosis to form asci each containing four ascospores of the haploid. These spores were separated with a micromanipulator and allowed to germinate on the YEA plate, followed by the formation of colonies. Then the resistance to aureobasidin of these colonies was examined. Among four spores contained in an ascus, the separation of the sensitivity versus the resistance showed 2:2. This result indicates that the aureobasidin resistant mutation was induced by a mutation in single gene. Further, the complementation test was performed in order to confirm whether the resistant genes of the above-mentioned five mutants were identical with each other or not. For example, a mutant of the mating type h$^+$, which had been obtained by crossing the mutant THR01 with the LH121 strain in the above tetrad analysis, was crossed with another variant THR04 (mating type h$^-$) on the MEA plate as described above and, after sporulation, the tetrad analysis was carried out. As a result, all of the colonies formed from four ascospores showed resistance to aureobasidin, which indicates that the mutational genes of THR01 and THR04 are the same with each other. Similarly, the five mutants were examined and it was thus found out that all mutations occurred on the same gene. This gene regulating aureobasidin sensitivity is named spaurl, the normal gene (sensitive gene) is named spaurl$^S$ and the mutational gene (resistant gene) is named spaurl$^R$.

1-c) Preparation of genomic library of aureobasidin resistant strain

Genomic DNA was extracted and purified from the aureobasidin resistant strain THR01 by the method of P. Philippsen et al. [Methods in Enzymology, 194, 169–175 (1991)]. The purified genomic DNA (8 μg) was partially digested by treating with 5 U of a restriction enzyme HindIII at 37° C. for 10 minutes, deproteinized with phenol/chloroform and precipitated with ethanol. The partially digested DNA was electrophoresed on a 0.8% agarose gel and DNA in the region of 3 to 15 kb was extracted. The DNA thus obtained was ligated with a yeast-*E. coli* shuttle vector PAU-PS (2 μg) which had been completely digested with HindIII by using a DNA ligation kit (manufactured by Takara Shuzo Co., Ltd.) and then transformed into *E. coli* HB101. Thus a genomic library of the aureobasidin resistant strain was formed. *E. coli* containing this genomic library was incubated in 50 ml of an LB medium (1% of bacto trypton, 0.5% of bacto yeast extract, 0.5% of sodium chloride) containing 100 μg/ml of ampicillin and 25 μg/ml of tetracycline at 37° C. overnight. Then a plasmid was recovered and purified from the *E. coli* cells.

1-d) Expression and cloning of aureobasidin resistant gene spaur1$^R$.

The plasmid originating in the genomic library of the aureobasidin resistant strain as prepared above was transformed into a strain *Schizo. pombe* JY745 by the method of Okazaki et al. [Nucleic Acid Research, 18, 6485–6489 (1990)]. The transformed cells were spreaded on a minimum medium SD plate [0.67% of yeast nitrogen base without amino acids (manufactured by Difco), 2% of glucose, 2% of agar] containing 75 μg/ml of adenine sulfate and 50 μg/ml of leucine. After incubating at 30° C. for 3 to 4 days, the colonies thus formed were replicated onto an SD plate containing 5 μg/ml of aureobasidin A, 75 μg/ml of adenine sulfate and 50 μg/ml of leucine. It is conceivable that a colony propagated on this plate may have the plasmid containing the aureobasidin resistant gene. This colony was inoculated into 5 ml of a liquid SD medium containing 75 μg/ml of adenine sulfate and 50 μg/ml of leucine. After incubating at 30° C. for 2 days, the plasmid was recovered from the propagated cells by the method of I. Hagan et al. [J. Cell Sci., 91, 587–595 (1988)] Namely, the cells were harvested from the culture (5 ml) by centrifugation and then suspended in 1.5 ml of 50 mM citrate/phosphate buffer containing 1.2 M of sorbitol and 2 mg/ml of Zymolyase. Then the suspension was maintained at 37° C. for 60 minutes. The cells were collected by centrifuging at 3,000 r.p.m. for 30 seconds and suspended in 300 μl of a TE [10 mM of Tris-HCl, pH 8, 1 mM of EDTA] solution. After adding 35 μl of 10% SDS, the mixture was maintained at 65° C. for 5 minutes. After adding 100 μl of 5 M potassium acetate, the mixture was allowed to stand in ice for 30 minutes. Then it was centrifuged at 10,000 r.p.m. at 4° C. for 10 minutes and a plasmid DNA was purified from the supernatant by using EASYTRAP™ (manufactured by Takara Shuzo Co., Ltd.).

Figure 12:
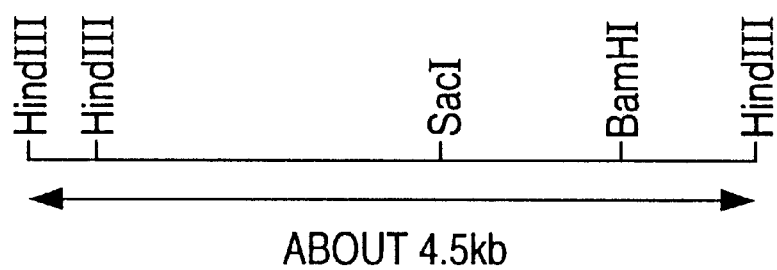
FIG. 12 is a restriction enzyme map of pAR25.
Figure 13:
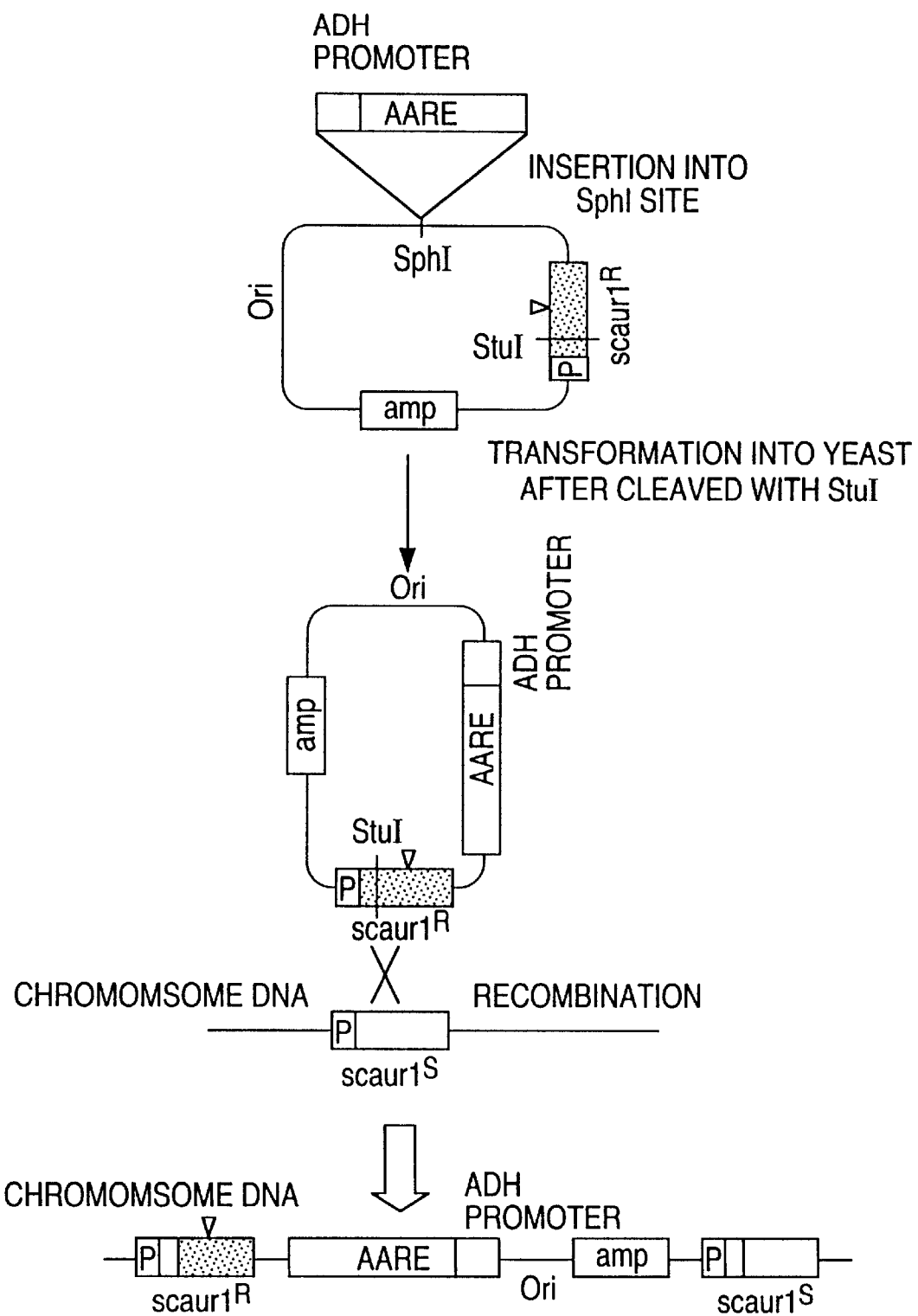
FIG. 13 shows a construction of the vector which is a example of the present invention, and integration of the vector into the chromosome.

This plasmid was transformed into *E. coli* HB101 and a plasmid DNA was prepared from *E. coli* colonies formed on an LB medium containing ampicillin and tetracycline. This plasmid, which contained a DNA of 4.5 kb, was named pAR25. FIG. 12 shows the restriction enzyme map of the DNA of 4.5 kb in pAR25. To specify the gene region, HindIII fragments or SacI fragments of various sizes were subcloned into the pAU-PS vector. These DNAs were transformed into normal JY745 cells by the above-mentioned method of Okazaki et al. and the acquisition of aureobasidin resistance was examined. As a result, it is revealed that a HindIII-SacI 2.4 kb DNA fragment contains the spaur1$^R$ gene. The restriction enzyme map of this DNA segment containing the aureobasidin resistant gene spaur1$^R$ is shown in FIG. 1. This fragment was cloned into a pUC118 vector (named pUARS2R) and then the DNA nucleotide sequence was identified (SEQ ID No. 1 in Sequence Listing). From this nucleotide sequence, it is revealed that the spaur1$^R$ gene code for a protein having an amino acid sequence represented by SEQ ID No. 2 in Sequence Listing.

1-e) Cloning of aureobasidin sensitive gene spaur1$^S$

By the same method as the one employed in the above c), genomic DNA was extracted and purified from normal cells. After partially digesting with HindIII, a genomic library of the normal cells was constructed. An *E. coli* stock containing this library DNA was spreaded on an LB agar medium containing ampicillin and tetracycline and incubated overnight at 37° C. The colonies thus formed were transferred onto a nylon membrane (Hybond™-N, manufactured by Amersham) and the colony hybridization was performed.

As a probe, the above-mentioned DNA fragment (2.4 kb) obtained by cleaving the spaur1$^R$ gene with HindIII-SacI and labeled with [α-$^{23}$P] dCTP by using a random primer DNA labeling kit (manufactured by Takara Shuzo Co., Ltd.) was used. As the results of screening of 5×10$^4$ colonies, five clones being hybridizable with the probe were obtained. Plasmids were purified from *E. coli* cells of these five clones. As the result of the cleavage with restriction enzymes, it was found out that all of these clones contained the same DNA fragment of 4.5 kb (named pARN1). The restriction enzyme map of the DNA of 4.5 kb in pARN1 was identical with that of pAR25 shown in FIG. 10. Therefore, a HindIII-SacI 2.4 kb DNA fragment which was a region containing the spaur1$^S$ gene was prepared from pARN1. Then it was cloned into the pAU-PS vector and this plasmid was named pSPAR1.

By using this plasmid pSPAR1, a strain *E. coli* JM109 was transformed and the transformant thus obtained was named and designated as *Escherichia coli* JM109/pSPAR1. It has been deposited at National Institute of Bioscience and Human-Technology, Agency of Industrial Science and Technology in accordance with the Budapest Treaty under the accession number FERM BP-4485. This DNA fragment containing the aureobasidin sensitive gene spaur1$^S$ had the restriction enzyme map shown in FIG. 1 and the DNA nucleotide sequence thereof was the one represented by SEQ ID No. 3 in Sequence Listing. Based on this nucleotide sequence, it has been revealed that the spaur1$^S$ gene codes for a protein having the amino acid sequence represented by SEQ ID No. 4 in Sequence Listing and, when compared with the resistant gene spaur1$^R$, the amino acid at the residue 240 has been changed from glycine into cysteine.

EXAMPLE 2

Cloning of Aureobasidin Sensitive Genes scaur1 and scaur2 Originating in Budding Yeast *S. cerevisiae*

2-a) Separation of aureobasidin resistant mutant of *S. cerevisiae*

A strain *S. cerevisiae* DKD5D (mating type a, genotype leu2-3 112, trp1, his3) having a sensitivity to aureobasidin at a concentration of 0.31 μg/ml was mutagenized with EMS in the same manner as the one employed in the case of *Schizo. pombe*. Then resistant mutants were separated on an agar plate of a complete nutritional medium YPD (1% of yeast extract, 2% of polypeptone, 2% of glucose) containing 5 μg/ml or 1.5 μg/ml of aureobasidin A. After repeating the mutagenesis several times, 34 mutant clones were obtained. These mutants were resistant to more than 25 μg/ml of aureobasidin A and estimated as having not a multiple drug resistance mutation but a aureobasidin-specific resistance mutation.

2-b) Genetic analysis

Similar to the above-mentioned case of *Schizo. pombe*, the genetic analysis using the tetrad analysis and the complementation test was performed. As a result, the genes could be classified into two types. These genes regulating aureobasidin sensitivity were named scaur1 and scaur2, the resistant genes isolated from the resistant mutant were named scaur1$^R$ and scaur2$^R$, and the sensitive genes isolated from the sensitive wild-type strain were named scaur1$^S$ and scaur2$^S$, respectively.

The R94A strain had a gene with dominant mutation (scaur1$^R$). It has been further clarified that the scaur1 gene is located in the neighborhood of the met14 gene of the eleventh chromosome.

2-c) Preparation of genomic library of aureobasidin resistant strain having aureobasidin resistant gene scaur1$^R$.

Genomic DNA was extracted and purified from the aureobasidin resistant strain R94A by the above-mentioned method of P. Philippsen et al. The purified genomic DNA (8 µg) was partially digested by treating with 5 U of a restriction enzyme HindIII at 37° C. for 10 minutes, deproteinized with phenol/chloroform and precipitated with ethanol. The partially digested DNA thus obtained was electrophoresed on a 0.8% agarose gel and DNA in the region of 3 to 15 kb was extracted. The DNA thus obtained was ligated with a yeast-*E. coli* shuttle vector pWH5 (2 µg) which had been completely digested with HindIII by using a DNA ligation kit and then transformed into *E. coli* HB101. Thus a genomic library was formed. *E. coli* containing this genomic library was cultured in 50 ml of an LB medium containing ampicillin and tetracycline at 37° C. overnight. Then a plasmid was recovered and purified from the *E. coli* cells.

2-d) Expression and cloning of aureobasidin resistant gene scaur1$^R$.

Figure 2:
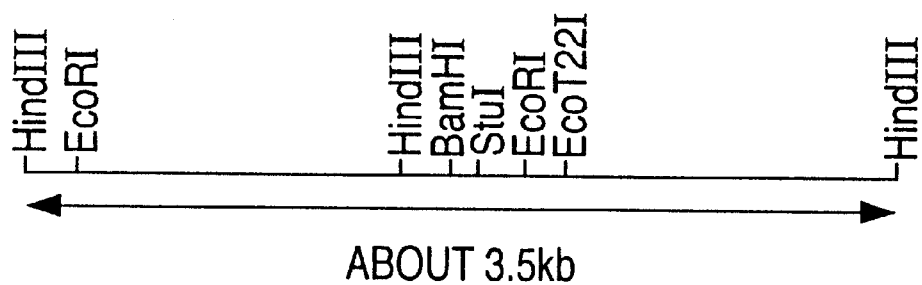
FIG. 2 is a restriction enzyme map of scaurl$^R$ and scaurl$^S$.

The above-mentioned genomic library of the R94A strain was transformed into *S. cerevisiae* SH3328 (mating type α, genotype ura3-52, his4, thr4, leu2-3. 112) in accordance with the method of R. H. Schiestl et al. [Current Genetics, 16, 339–346 (1989)]. The transformed cells were spread on a minimum medium SD plate [0.67% of yeast nitrogen base without amino acids, 2% of glucose, 2% of agar] containing 25 µg/ml of uracil, 35 µg/ml of histidine and 500 µg/ml of threonine. After incubating at 30° C. for 3 to 4 days, the colonies thus formed were replicated onto a YPD agar plate containing 1.5 µg/ml of aureobasidin A. A colony thus formed was inoculated into 5 ml of a liquid YPD medium. After incubating at 30° C. for 2 days, a plasmid DNA was recovered from the propagated cells by the above-mentioned method of I. Hagan et al. This plasmid was transformed into a yeast again and it was confirmed that the obtained transformant had acquired aureobasidin resistance. This plasmid, which contained a DNA of 3.5 kb, was named pWTCR3. Neither the DNA fragment of 2.0 kb nor the DNA fragment of 1.5 kb obtained by cleaving with HindIII exhibited any aureobasidin resistant activity alone. Thus it is confirmed that the gene is contained in the DNA fragment of 3.5 kb. FIG. 2 shows the restriction enzyme map of this DNA fragment of 3.5 kb containing the aureobasidin resistant gene scaur1$^R$. The HindIII fragments of 1.5 kb and 2 kb were each cloned into pUC118, followed by the determination of the DNA nucleotide sequence (SEQ ID No. 5 in Sequence Listing). From this nucleotide sequence, it has been revealed that the scaur1$^R$ gene codes for a protein having an amino acid sequence represented by SEQ ID No. 6 in Sequence Listing.

2-e) Cloning of aureobasidin sensitive gene scaur1$^S$ corresponding to aureobasidin resistant gene scaur1$^R$.

By the same method as the one employed in the above Example 2-c), genomic DNA was extracted and purified from the parent strain *S. cerevisiae* DKD5D. After partially digesting with HindIII, the DNA was ligated with pWH5 and transformed into *E. coli* HB101. Thus a genomic library of the normal cells was formed. An *E. coli* stock containing this library DNA was spreaded on an LB agar medium containing ampicillin and tetracycline and incubated overnight at 37° C. The colonies thus formed were transferred onto a nylon membrane (Hybond™-N) and the colony hybridization was carried out. As a probe, the DNA fragment of 3.5 kb obtained in the above Example 2-d) and labeled with [α-$^{32}$p] dCTP by using a random primer DNA labeling kit (manufactured by Takara Shuzo Co., Ltd.) was used. As the results of screening of 2×10$^4$ colonies, seven clones being hybridizable with the probe were obtained. Plasmids were purified from *E. coli* cells of these clones. As the result of the cleavage with restriction enzymes, one of these clones contained a DNA fragment of 3.5 kb. This DNA fragment had the restriction enzyme map of FIG. 2 and thus judged as containing the scaur1$^S$ gene. The plasmid containing this DNA fragment was named pSCAR1, while *E. coli* HB101 having this plasmid introduced therein was named and designated as *Escherichia coli* HB101/pSCAR1. This strain has been deposited at National Institute of Bioscience and Human-Technology, Agency of Industrial Science and Technology in accordance with the Budapest Treaty under the accession number FERM BP-4483. The DNA fragment of 3.5 kb obtained by partially digesting pSCAR1 with HindIII was subcloned into pUC118 and the nucleotide sequence thereof was determined (SEQ ID No. 7 in Sequence Listing). A comparison with the resistant gene indicates that the base at the position 852 has been changed from T into A and, due to this replacement, the amino acid has been converted from phenylalanine into tyrosine (SEQ ID No. 8 in Sequence Listing).

2-f) Preparation of genomic library of aureobasidin resistant strain having aureobasidin resistant gene scaur2$^R$.

A genomic library was prepared from an aureobasidin resistant strain L22-8B by the same method as the one described in Example 2-c). *E. coli* containing this genomic library was cultured in an LB medium (50 ml) containing ampicillin and tetracycline at 37° C. overnight. Then plasmids were recovered and purified from the *E. coli* cells.

2-g) Expression and cloning of aureobasidin resistant gene scaur2$^R$

Figure 3:
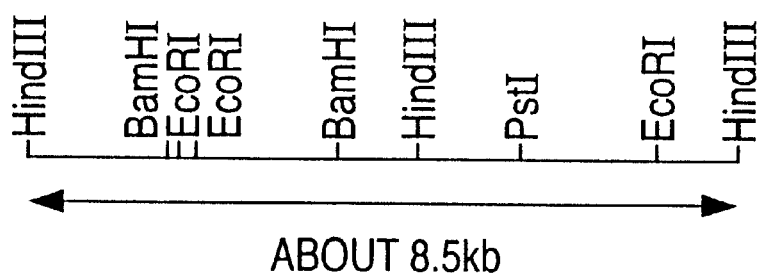
FIG. 3 is a restriction enzyme map of scaur2$^R$ and scaur2$^S$.

The above-mentioned plasmids originating in the genomic library of the L22-8B strain were transformed into *S. cerevisiae* SH3328 by the above-mentioned method of R. H. Schiestl. From the transformed strains, an aureobasidin resistant strain was isolated. Then a plasmid DNA containing the scaur2$^R$ gene was recovered from this transformant by the above-mentioned method of I. Hagan et al. This plasmid was transformed into a yeast again and it was confirmed that the transformant had acquired aureobasidin resistance. This plasmid, which contained a DNA of 8.5 kb, was named pSCAR2. FIG. 3 shows the restriction enzyme map of the DNA fragment of 8.5 kb containing this aureobasidin resistant gene scaur2$^R$. *E. coli* HB101 having this plasmid pSCAR2 introduced therein was named and designated as *Escherichia coli* HB101/pSCAR2. This strain has been deposited at National Institute of Bioscience and Human-Technology, Agency of Industrial Science and Technology in accordance with the Budapest Treaty under the accession number FERM BP-4484. By using BamHI, EcoRI, HindIII and PstI, DNA fragments of various sizes were prepared and cloned into the pWH5 vector. These plasmids were transformed into S. cerevisiae DKD5D in accordance with the above-mentioned method of R. H. Schiestl et al. Then it was examined whether these transformants had acquired aureobasidin resistance or not. As a result, none of the transformants of the DNA fragments was a resistant one. Thus it has been clarified that the DNA fragment of the full length is necessary for the expression of the aureobasidin resistance.

2-h) Isolation of aureobasidin sensitive gene scaur2$^S$ corresponding to aureobasidin resistant gene scaur2$^R$.

An E. coli stock containing the genomic library of Example 2-e) prepared from normal cells of S. cerevisiae DKD5D was spreaded on an LB agar medium containing ampicillin and tetracycline and incubated at 37° C. overnight. The colonies thus formed were transferred onto a nylon membrane (Hybond™-N) and the colony hybridization was performed. As a probe the DNA fragment of 8.5 kb obtained in the above Example 2-g) and labeled with [α-$^{32}$P] dCTP by using a random primer DNA labeling kit was used. As the results of screening of 2×10$^4$ colonies, several clones being hybridizable with the probe were obtained. Some of these clones contained a DNA fragment of 4.6 kb while others contained a DNA fragment of 3.9 kb. From the restriction enzyme maps of these DNA fragments, it was found out that these DNA fragments were each a part of the scaur2$^S$ gene shown in FIG. 3. These DNA fragments were ligated together to thereby give a scaur2$^S$ fragments shown in FIG. 3. The DNA fragment of 8.5 kb thus obtained was subcloned into pUC118 and then the DNA nucleotide sequence was determined (SEQ ID No. 9 in Sequence Listing). Based on the nucleotide sequence of SEQ ID No. 9 in Sequence Listing, the amino acid sequence represented by SEQ ID No. 10 in Sequence Listing was estimated.

EXAMPLE 3

Figure 4:
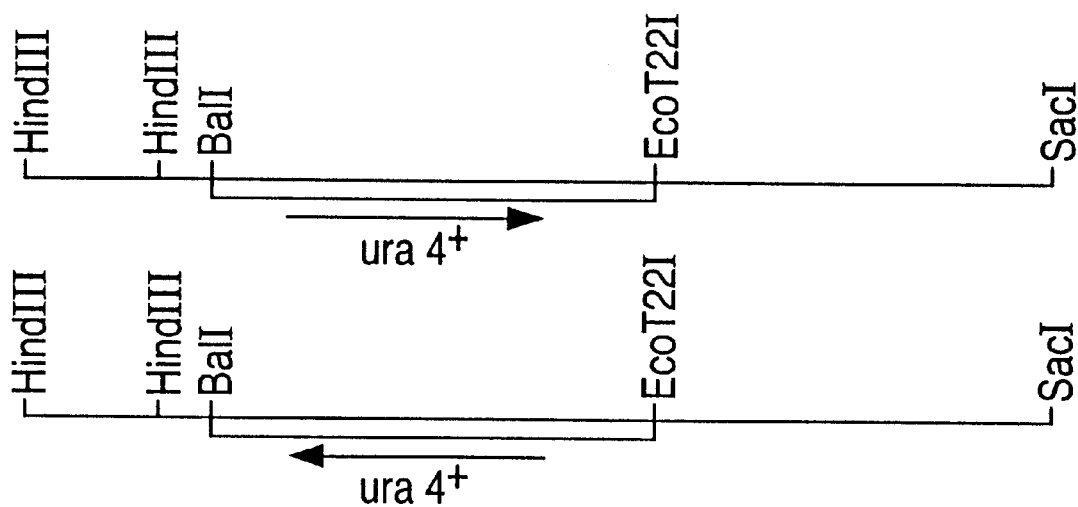
FIG. 4 shows the structure of a DNA for disrupting the *Schizo. pombe* spaurl$^S$ gene.

Gene Disruption Test on Spaur1$^S$ and Scaur1$^S$ Genes 3-a) Gene disruption test on spaur1$^S$ gene In order to examine whether the aureobasidin sensitive gene spaur1$^S$ is necessary in the cell growth by the gene disruption test, the plasmid pUARS2R prepared in Example 1-d) was first cleaved with BalI and EcoT22I. After eliminating a DNA fragment of 240 bp, the residual DNA fragment was blunted by using a DNA blunting kit (manufactured by Takara Shuzo Co., Ltd.). Then this DNA was ligated with a DNA containing ura4$^+$gene of 1.7 kb, which had been obtained by excising from a pUC8ura4 plasmid [Mol. Gen. Genet., 215, 81–86 (1988)] by cleaving with HindIII and blunting, to thereby give a plasmid pUARS2RBT22::ura4-1 and another plasmid pUARS2RBT22::ura4-6 in which the ura4 DNA had been inserted in the opposite direction. Both of these disrupted genes were excised from the vector pUC118 by cleaving with SacI and HindIII and ARS2RBT22::ura4-1 and ARS2RBT22::ura4-6 (FIG. 4), which were spaur1$^S$ DNA fragments containing ura4$^+$, were purified. The purified DNA fragments were transformed into diploid cells Schizo. pombe C525 (h$^{90}$/h$^{90}$, ura4-D18/ura4-D18, leu1/leu1, ade6-M210/ade6-M216) by the above-mentioned method of Okazaki et al. and then a transformant was screened on an SD agar plate containing leucine. In the transformant thus obtained, one of a pair of spaur1 genes on the chromosome had been replaced by the disrupted gene ARS2RBT22::ura4-1 or ARS2RBT22::ura4-6 introduced thereinto. These cells were allowed to undergo sporulation on a sporulation medium MEA and subjected to the tetrad analysis. As a result, it was found out that two of the four ascospores formed colonies but the residual two spores formed no colony. That is to say, the spores suffering from the replacement of the normal spaur1$^S$ gene by the disrupted gene ARS2RBT22::ura4-1 were not propagated. It has been thus revealed that the spauris gene is essentially required for the growth of the cells.

3-b) Gene disruption test on scaur1$^S$ gene

Figure 5:
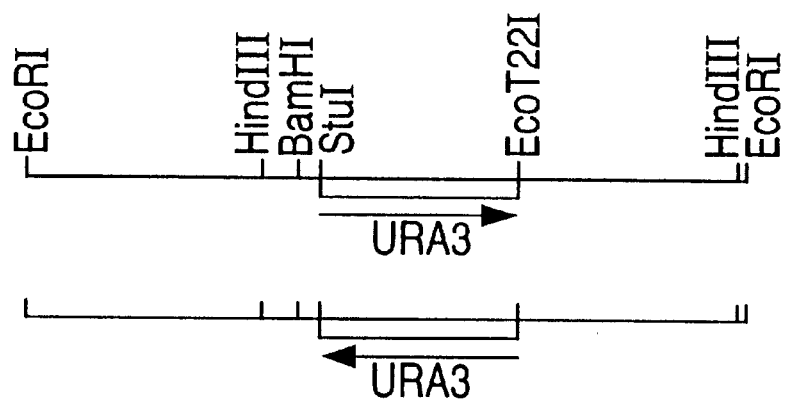
FIG. 5 shows the structure of a DNA for disrupting the *S. cerevisiae* scaurl$^S$ gene.

The plasmid pSCAR1 prepared in Example 2-e) was partially digested with HindIII to thereby give a DNA fragment of 3.5 kb shown in FIG. 2. This DNA fragment was cloned into the HindIII site of pUC119 and the obtained product was named pSCAR3. The obtained pSCAR3 was cleaved with StuI and EcoT22I. After eliminating a DNA fragment of 0.3 kb, the obtained DNA was ligated with a DNA fragment (1.1 kb) of URA3 gene which had been obtained by cleaving a plasmid pYEUra3 (manufactured by Clontech Laboratories, Inc.) with HindIII and EcoRI and blunting. Thus a plasmid pUSCAR3. ST22::URA3$^+$ and another plasmid pUSCAR3.ST22::URA3A, in which the URA3 gene had been inserted in the opposite direction, were obtained. These disrupted gene were excised in the EcoRI site in the scaur1$^S$ gene and the EcoRI site in the pUC119 vector by cleaving with EcoRI. The scaur1$^S$ DNA fragments containing URA3, SCAR3.ST22::URA3+ and SCAR3.ST22::URA3A (FIG. 5), were purified. The purified DNA fragments were transformed into diploid cells of S. cerevisiae AOD1 (mating type a/α, genotype ura3-52/ura3-52, leu2-3 112/leu2-3 112, trp1/TRp1, thr4/THR4, his4/HIS4) by the above-mentioned method of R.H. Schiestl and transformants were screened on an SD agar plate containing leucine. The transformants thus obtained were allowed to undergo sporulation on a sporulation Admedium SP (1% of potassium acetate, 2% of agar) and subjected to the tetrad analysis. As a result, it was found out that two of the four ascospores underwent germination and formed colonies but the residual two spores did not undergo colony formation. That is to say, the spores suffering from the replacement of the scaur1$^S$ gene by the disrupted gene were not propagated. It has been thus revealed that the scaur1$^S$ gene is essentially required for the growth of the cells.

EXAMPLE 4

Figure 10:
FIG. 10 shows the results of the northern hybridization of the spaurl gene of *Schizo. pombe*.

Examination on the Expression of Aureobasidin Sensitive Gene Spaur1 by Northern Hybridization From a normal strain or a resistant strain of Schizo. pombe, the whole RNAs were extracted and purified by the method of R. Jensen et al. [Proc. Natl. Acad. Sci. USA, 80, 3035–3039 (1983)]. Further, poly(A)$^+$RNA was purified by using Oligotex™-dT30 (manufactured by Takara Shuzo Co., Ltd.). The purified poly(A)$^+$RNA (2.5 μg) was separated by the electrophoresis on a 1.2% agarose gel containing formaldehyde and transferred onto a nylon membrane (Hybond™-N). After immobilizing, the hybridization was performed with the use of a HindIII-SacI fragment (2 kb) of the spaur1$^R$ gene labeled with [α-$^{32}$P]dCTP as a probe. As a result, both of the normal cells and the resistant cells showed a band of the same amount of about 2 kb. In both cases, this amount underwent no change in the logarithmic growth phase and the stationary phase (FIG. 10). FIG. 10 is an autoradiogram showing the results of the northern hybridization wherein mRNAs obtained from cells of a sensitive strain of Schizo. pombe in the logarithmic growth phase (lane 1), cells of a resistant strain in the logarithmic growth phase (lane 2), cells of the sensitive strain in the stationary phase (lane 3) and cells of the resistant strain in the stationary phase (lane 4) are electrophoresed on a 1.2% agarose gel containing formaldehyde.

EXAMPLE 5

Determination of the Activity of scaur1$^S$ Gene
5-a) Construction of plasmid YEpSCARW3 (FIG. 9) and YEpSCARW1

Figure 9:
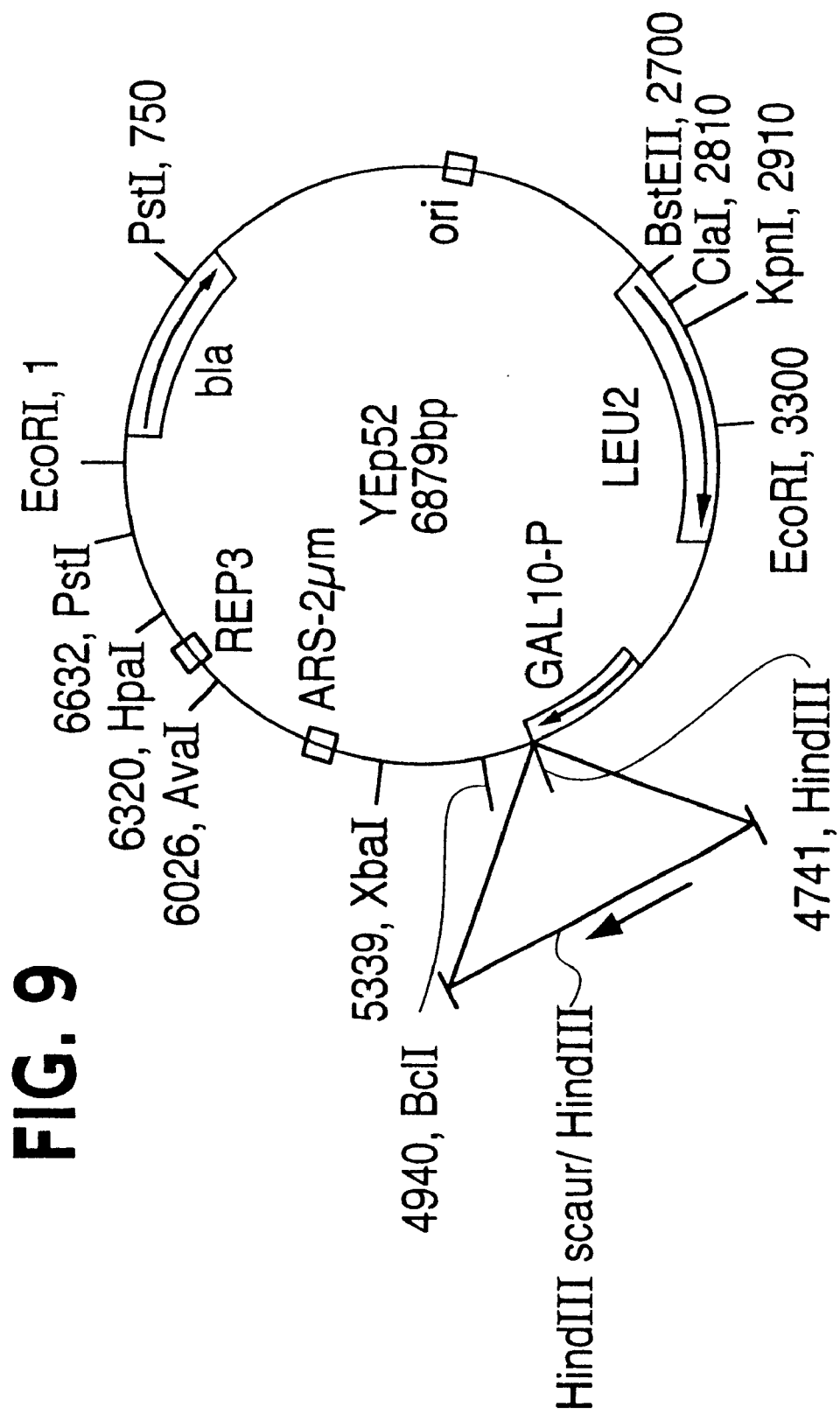
FIG. 9 shows the structure of a plasmid YEpSCARW3 for expressing the scaurl gene.

The plasmid pSCAR1 prepared in Example 2-e) was cleaved with HindIII and a fragment of 2 kb containing the whole ORF was excised. This fragment was inserted into the HindIII site of a expression-plasmid YEp52 having a promoter Gal10, the expression of which was induced by galactose in a medium. The plasmid having the scaur1$^S$ gene which had been inserted in such a direction as to be normally transcribed by the promoter Gal10 was named YEpSCARW3. FIG. 9 shows the structure of this plasmid. Further, the plasmid having the scaur1$^S$ gene inserted in the opposite direction was named YEpSCARW1.

5-b) Transformation by plasmids YEpSCARW3 and YEpSCARW1

By using 5 μg portions of the plasmids YEpSCARW3 and YEpSCARW1, the diploid S. cerevisiae cells with the disrupted scaur1$^S$ gene prepared in Example 3-b) were transformed. Then transformants were screened on an SD agar plate. These transformants were allowed to undergo sporulation on an SP medium and then subjected to the tetrad analysis. When the expression of the scaur1$^S$ gene was induced by using a YPGal medium (1% of yeast extract, 2% of polypeptone, 2% of galactose), the ascospores formed from the diploid cells transformed by YEpSCARW3 all underwent germination while two of the four ascospores formed from the diploid cells transformed by YEpSCARW1 underwent germination but not the remaining two. It is thus conceivable that the cells with the disrupted scaur1$^S$ gene have reverted to the normal state by introducing YEpSCARW3 containing the scaur1$^S$ gene into these cells. Accordingly, the use of these cells with the disrupted scaur1$^S$ gene as a host makes it possible to determine the activity of normal aur1-analogous genes carried by other organisms.

EXAMPLE 6

Confirmation and Cloning of aur1 and aur2 Genes (caaur1, caaur2) Carried by C. albicans 6-a) Detection of aur1 gene by the PCR method Poly(A)$^+$RNA was extracted and purified from an aureobasidin sensitive strain C. albicans TIMM0136 by the same method as the one employed in Example 4. By using the poly(A)$^+$RNA (5 μg) as a template, a double-stranded cDNA was synthesized on a cDNA synthesizing system Plus (manufactured by Amersham) with the use of an oligo(dT) primer. Mixed primers for PCR corresponding to amino acid sequence regions being common to the amino acid sequences of S. cerevisiae and Schizo. pombe were synthesized on a DNA synthesizer and purified. That is to say, a primer of SEQ ID No. 11 in Sequence Listing corresponding to the region of amino acids at the 184- to 192-positions of SEQ ID No. 4 in Sequence Listing of Schizo. pombe (from the 184- to 192-positions of SEQ ID No. 8 in Sequence Listing of S. cerevisiae) and another primer of SEQ ID No. 12 in Sequence Listing corresponding to the region of amino acids from the 289- to 298- positions of Schizo. pombe (from the 289- to 298-positions of SEQ ID No. 8 in Sequence Listing of S. cerevisiae) were employed.

Figure 6:
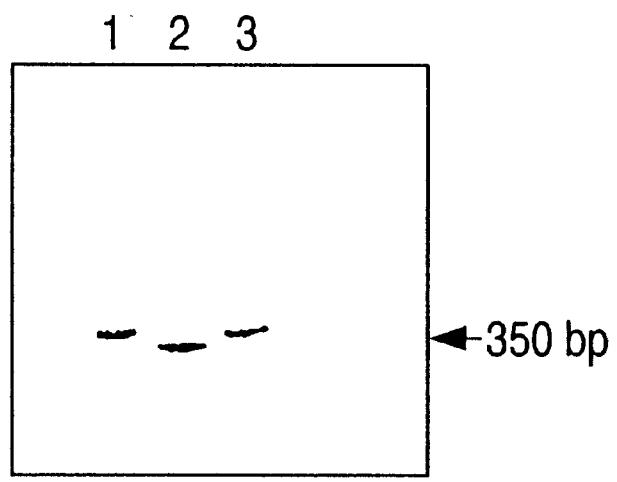
FIG. 6 shows the results of the detection of the aurl gene caaurl carried by *C. albicans* by the PCR method.

PCR was performed by using these primers and the above-mentioned cDNA as a template by repeating a cycle comprising treatment at 94° C. for 30 seconds, one at 48° C. for 1 minute and one at 72° C. for 2 minutes 25 times. As a result, a DNA (about 350 bp) being almost the same as S. cerevisiae and Schizo. pombe in length was amplified (FIG. 6). FIG. 6 shows a pattern obtained by carrying out PCR with the use of cDNA of C. albicans (lane 1), cDNA of S. cerevisiae (lane 2) and cDNA of Schizo. pombe (lane 3) as a template, electrophoresing each PCR product on an agarose gel and staining with ethidium bromide.

Figure 7:
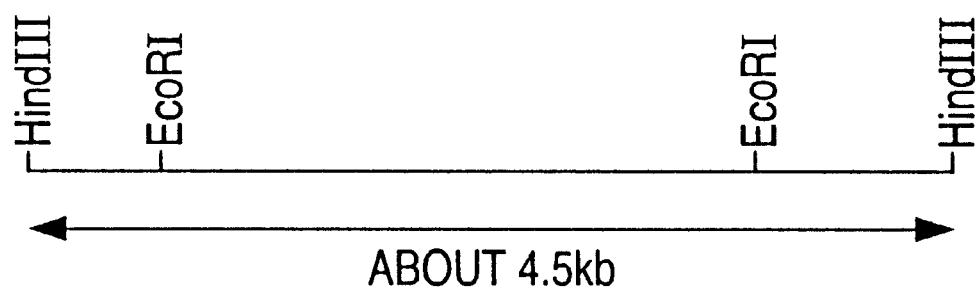
FIG. 7 is a restriction enzyme map of the caaurl gene carried by *C. albicans*.

6-b) Cloning of aur1 gene (caaur1) of C. albicans (i) Genomic DNA was extracted and purified from a strain C. albicans TIMM0136 by the same method as the one described in Example 1-c). After partially digesting with HindIII, the DNA fragment was ligated with a Traplexll9 vector which had been completely digested with HindIII and transformed into E. coli HB101. Thus a genomic library of C. albicans was prepared. From this library, a DNA fragment of 4.5 kb containing the aur1 gene of C. albicans was cloned by using the DNA fragment of C. albicans obtained by the PCR described in Example 6-a), which had been labeled with [α-$^{32}$P]dCTP by using a random primer DNA labeling kit (manufactured by Takara Shuzo Co., Ltd.), as a probe. This DNA fragment had a restriction enzyme map shown in FIG. 7 and the DNA nucleotide sequence thereof is represented by SEQ ID No. 13 in Sequence Listing. Based on this nucleotide sequence, it was estimated that the caaur1 gene coded for a protein having the amino acid sequence represented by SEQ ID No. 14 in Sequence Listing. When compared with the scaur1$^S$ protein, a homology of as high as 53% was observed. A Traplexll9 vector having this caaur1 gene integrated therein was named pCAAR1, while E. coli HB101 transformed by this plasmid was named and designated as Escherichia coli HB101/pCAAR1. This strain has been deposited at National Institute of Bioscience and Human-Technology, Agency of Industrial Science and Technology in accordance with the Budapest Treaty under the accession number FERM BP-4482.

Next, pCAAR1 was treated with HindIII to thereby give caaur1 of 4.5 kb. Further, it was integrated into pTV118 which had been completely digested with HindIII to thereby prepare a plasmid for expressing caaur1. This plasmid was named pTCAAR1.

(ii) Genomic DNA was extracted and parified from a strain C. albicans TIMM1768 [The Journal of Antibiotics, 46, 1414–1420(1993)] by the same method as the one described in Example 1-c). After partially digesting with HindIII, the DNA fragment was ligated with a pUC118 vector which had been completely digested with HindIII and transformed into E. coli HB101. Thus a genomic library of C. albicans TIMM1768 was prepared. From this library, a DNA fragment of 4.5 kb containing the aur1 gene of C. albicans TIMM1768 was cloned by the colony hybridization with the same probe as that described in Example 6-b)-(i). This DNA fragment had the same restriction enzyme map as that shown in FIG. 7. Next, a part of the DNA sequence containing a ORF in this DNA fragment was determined. The DNA nucleotide sequence thereof is represented by SEQ ID No. 21 in Sequence Listing. Based on this nucleotide sequence, it was estimated that this gene coded for a protein having the amino acid sequence represented by SEQ ID No. 22 in Sequence Listing. When the amino acid sequence of the caaur1 protein C. albicans TIMM1768 was compared with that of the caaur1 protein of C. albicans TIMM0136, the amino acid sequences of the 1- to 381-positions and the 383- to 423-positions and the 425- to 471-positions of caaur1 protein (SEQ ID No. 14 in Sequence Listing) in C. albicans TIMM0136 were identical with the amino acid sequences of the 2- to 382-positions and the 384- to 424-positions and the 426- to 472-positions, respectively, of caaur1 protein (SEQ ID No. 22 in Sequence Listing) in C. albicans TIMM1768.

However, serines at the 382- and 424-positions of SEQ ID No. 14 in Sequence Listing were replaced with prolines at the 383- and 425-positions of SEQ ID No. 22 in Sequence Listing. 6-c) Cloning of aur2 gene (caaur2) of *C. albicans*

Figure 8:
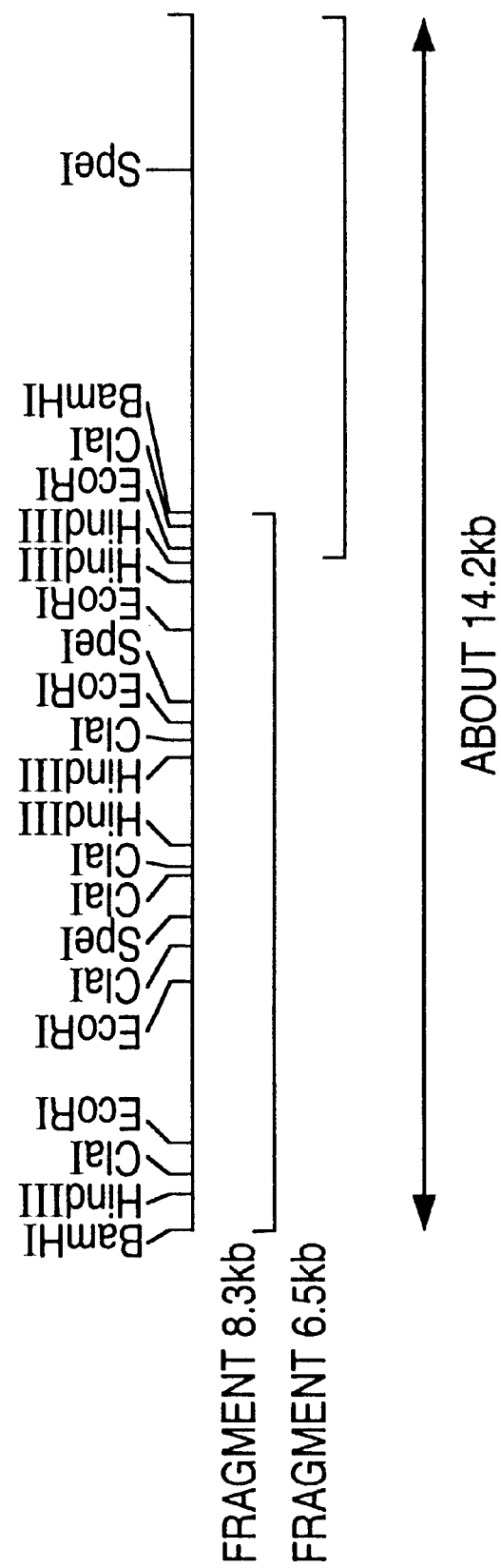
FIG. 8 is a restriction enzyme map of the caaur2 gene.

Genomic DNA of a strain *C. albicans* TIMM0136 was digested with BamHI and ligated with a pTV118 vector which had been completely digested with BamHI. Then it was transformed into *E. coli* HB101 to thereby prepare a genomic library of *C. albicans*. On the other hand, the DNA fragment containing the scaur2$^S$ gene obtained in Example 2-h) was cleaved with HindIII and PstI to thereby give a DNA fragment of 1.2 kb. This DNA fragment was labeled with [α-$^{32}$P]dCTP by using a random primer DNA labeling kit. By using this labeled DNA fragment as a probe, the above-mentioned *C. albicans* genomic library was screened by the colony hybridization. Thus a plasmid containing a DNA fragment of 8.3 kb was obtained. A part of the DNA sequence upstream of the BamHI site of this DNA fragment was determined (SEQ ID No. 15 in Sequence Listing). Based on this sequence, an amino acid sequence represented by SEQ ID No. 16 in Sequence Listing was estimated. It corresponded to the amino acid sequence of the 1230- to 1309-positions of the amino acid sequence of the scaur2 gene (SEQ ID No. 10), having a homology of as high as 77%. Since this DNA fragment lacked a part of the C-end, the genomic library prepared in Example 6-b) was further screened by using this DNA fragment as a probe. Thus a DNA fragment of 6.5 kb having the C-terminal part was obtained. FIG. 8 shows the restriction enzyme map of the DNA region containing the caaur2 gene thus clarified.

A pTV118 vector having the above-mentioned caaur2 gene of 8.3 kb integrated therein was named pCAAR2N, while *E. coli* HB101 transformed by this plasmid was named and designated as *Escherichia coli* HB101/pCAAR2N. This strain has been deposited at National Institute of Bioscience and Human-Technology, Agency of Industrial Science and Technology in accordance with the Budapest Treaty under the accession number FERM BP-4481.

EXAMPLE 7

Preparation of Antibody Against Protein Coded for by scaur1$^S$ Gene and Staining of *S. cerevisiae* Cells and Detection of Said Protein by Using this Antibody.

7-a) Preparation of antibody

SCAR1-1 (SEQ ID No. 19 in Sequence Listing) comprising a peptide corresponding to the amino acids at the residue 103 to 113 in the amino acid sequence of SEQ ID No. 8 in Sequence Listing having cysteine added to the N-end thereof and SCAR1-2 (SEQ ID No. 20 in Sequence Listing) comprising a peptide corresponding to the amino acids at the residue 331 to 348 in the amino acid sequence of SEQ ID No. 8 having cysteine added to the N-end thereof were synthesized by the Fmoc solid phase synthesis method and purified by reverse phase HPLC. Thus 10 mg portions of these peptides were obtained. To the N-terminal cysteine of each of these synthetic peptides, KLH was bound as a carrier protein. By using this binding product as an antigen, a rabbit was immunized and an antiserum was obtained. This antiserum was further purified on an affinity column prepared by binding the synthetic peptide employed as the antigen to an agarose gel. This a polyclonal antibody being specific for the synthetic peptide was prepared.

7-b) Staining of *S. cerevisiae* cells with antibody

A strain *S. cervisiae* ATCC 9763 was cultured in a YNBG medium [0.67% of yeast nitrogen base (manufactured by Difco), 2% of glucose] to thereby give a suspension of a concentration of 3×10$^7$ cells/ml. To 1 ml of this cell suspension were added 0.11 ml of a 1 M phosphate buffer (pH 6.5) and 0.17 ml of 37% formaldehyde. After slowly stirring at room temperature for 1 hour, the cells were harvested by centrifugation and then suspended in 20 ml of an SS buffer (1 M of sorbitol, 0.2% of β-mercaptoethanol, 0.1 M phosphate buffer, pH 7.5) containing 20 μg/ml of Zymolyase 20T. After treating at 30° C. for 1 hour, the cells were harvested, washed with the SS buffer, suspended in 1 ml of the SS buffer containing 0.1% of Triton X-100 and then allowed to stand for 10 minutes. This cell suspension was placed on a slide glass which had been coated with poly(L-lysine) and allowed to stand for 10 minutes. Next, a PBS solution containing 1% of albumin (BSA) was dropped thereinto. After allowing to stand at room temperature for 15 minutes, the excessive liquid was removed and then a PBS solution containing BSA containing 0.02 mg/ml of the antiSCAR1-1 antibody was dropped thereinto. After allowing to stand at room temperature for 60 minutes and washing with PBS containing BSA three times, antirabbit IgG antibody labeled with FITC (antibody concentration 0.02 mg/ml) was layered over and allowed to stand at room temperature for 1 hour. After washing with a PBS solution containing BSA, a small amount of a mounting solution, which was a solution prepared by dissolving 0.1 g of p-phenylenediamine in 10 ml of CBS (150 mM of NaCl, 50 mM of CHES, pH 9.5), adjusting the pH value to 9.0 with 10 N NaOH and further adding 90 ml of glycerol, was layered over. Then a cover glass was placed thereon to thereby give a specimen. This specimen was observed under a fluorescence microscope to thereby examine the intracellular distribution of the scaur1 protein. As a result, it was found out that this protein was distributed all over the cells.

7-c) Detection of Protein Coded for by scaur1 Gene by Using Antibody

Figure 11:
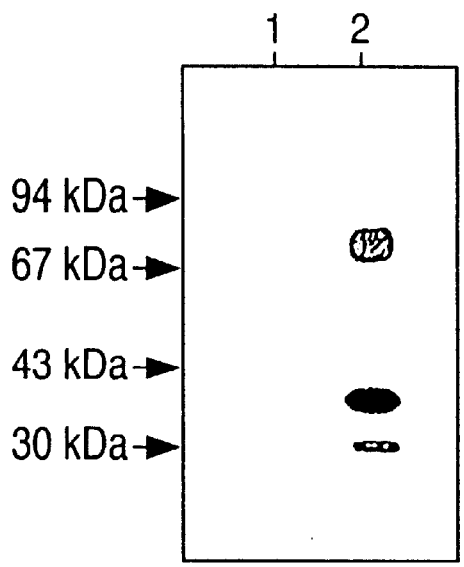
FIG. 11 shows the results of the detection of the scaurl protein by using an antibody.

The plasmid YEpSCARW3 prepared in Example 5-a) was introduced into a normal haploid *S. cerevisiae* SH3328 to thereby give a transformant. This transformant was cultured in a YPGal medium or a YPD medium and the cells were harvested by centrifugation. The cells thus obtained were suspended in a buffer (1% of Triton X-100, 1% of SDS, 20 mM of Tris-HCl, pH 7.9, 10 mM of EDTA, 1 mM of DTT, 1 mM of PMSF). Further, glass beads were added thereto to disrupt the cells by vigorous vortex. Then an SDS loading solution was added thereto and the protein was denatured by treating at 95° C. for 5 minutes. After centrifuging, a part of the obtained supernatant was subjected to SDS-PAGE and the protein thus separated was transfered onto an Immobilon membrane (manufactured by MILLIPORE). This Immobilon membrane was treated with Block Ace (manufactured by Dainippon Pharmaceutical Co., Ltd.). Then the antiSCAR1-2 antibody prepared in 7-a) was reacted therewith as a primary antibody. After washing, antirabbit IgG antibody labeled with peroxidase was reacted therewith as a secondary antibody and the mixture was thoroughly washed. Next, it was color-developed with diaminobenzidine and a band of the scaur1 protein was detected. FIG. 11 shows the results.

FIG. 11 shows the results of the detection of the protein prepared from the cells incubated in the YPD medium (lane 1) and the protein prepared from the cells incubated in the YPGal medium (lane 2), each subjected to SDS-PAGE, by using the antiSCAR1-2 antibody. The cells incubated in the YPGal medium, of which scaur1 gene had been induced, showed a specific band.

EXAMPLE 8

Construction of Chromosome Integration Vector Containing Aureobasidin Resistant Gene 8-a) Construction of replication vector containing scaur1$^R$ A plasmid pSCAR1 was prepared from *Escherichia coli* HB101/pSCAR1 (FERM BP-4483) which carried a plasmid pSCAR1 containing scaur1$^S$. Then the obtained plasmid was partially cleaved with HindIII and thus a DNA of 3.5 kb containing scaur1$^S$ was separated therefrom. This DNA (3.5 kb) was ligated to a vector pUC118 cleaved with HindIII to thereby prepare a plasmid puscaur1$^S$. This plasmid puscaur1$^S$ was transformed into *Escherichia coli* CJ236 to thereby prepare ssDNA.

Next, a site-specific DNA mutation was introduced by using Mutan-K kit (manufactured by Takara Shuzo Co., Ltd.) with the use of a synthetic oligonucleotide for introducing mutation represented by SEQ ID No. 23 in the Sequence Listing, which had been synthesized and purified, and the above-mentioned ssDNA. That is to say, the use of the oligonucleotide represented by SEQ ID No. 23 in the Sequence Listing made it possible to obtain scaur1$^R$ wherein the codon TTT of the 158th amino acid residue Phe in the ORF of the gene scaur1$^S$ had been replaced by the codon TAT of Tyr. This plasmid having a DNA coding for Aur1$^R$p (F158Y) was designated as pUscaur1R.

8-b) Amplification of scaur1$^R$ by PCR method

By using the plasmid puscaur1$^R$ which carried a HindIII fragment of 3.5 kb containing scaur1$^R$, scaur1$^R$ (about 1.9 kb) was amplified by the PCR method. Regarding primers employed herein, XhoI and KpnI sites had been designed in primers in order to clone the amplified scaur1$^R$ into the plasmid vector pYES2 (manufactured by Invitrogen corporation) and thus primers represented by SEQ ID Nos. 24 and 25 in the Sequence Listing were synthesized.

The reaction was effected in the following manner. 100 μl of a PCR solution containing 28 μl of a PCR buffer [capable of giving final concentrations of 10 mM of Tris-HCl (pH 8.3), 50 mM of KCl, 1.5 mM of MgCl$_2$, 0.1 mM of dATP, 0.1 mM of dCTP, 0.1 mM of dTTP and 0.1 mM of dGTP], 1 μl of 2.5 U of Ampli Taq DNA polymerase (Manufactured by Perkin-Elmer), 0.5 μl portions of 20 pmol of the primers represented by SEQ ID Nos. 24 and 25 in the Sequence Listing, 1 μl of the plasmid and 69 μl of H$_2$O was maintained at an initial temperature of 94° C. for 1 minute, and then heated successively at 94° C. for 1 minute, at 50° C. for 2 minutes and at 72° C. for 3 minutes. This heating cycle was repeated 35 times. Next, the reaction mixture was maintained at 72° C. for 10 minutes to thereby effect the amplification by PCR. Then the PCR amplification product was cleaved with KonI and XhoI and electrophoresed on an agarose gel and the target DNA fragment of about 1.9 kb was recovered from the gel and purified by using Suprec™-01 (manufactured by Takara Shuzo Co., Ltd.).

8-c) DNA ligation and transformation

About 0.3 μg of the DNA fragment (about 1.9 kb) purified in the above step was ligated to about 0.1 μg of pYES2, which had been digested with XhoI and KpnI, by using a DNA ligation kit (manufactured by Takara Shuzo Co., Ltd.).

Next, 7 μl of the above-mentioned ligation mixture was added to 200 μl of competent cells of *Escherichia coli* HB101. These cells were allowed to stand on ice for 30 minutes, at 42° C. for 1 minute and then on ice again for 1 minute. Then 800 μl of an SOC medium [Sambrook et al., "*Molecular Cloning, A Laboratory Manual*", Cold Spring Harbor Laboratory Press (1989)] was added thereto. After incubating at 37° C. for 1 hour, these *Escherichia coli* cells were spread onto an L-broth agar medium containing 50 μg/ml of ampicillin and incubated at 37° C. overnight. Thus a transformant was obtained.

This transformant was incubated in 5 ml of an L-broth medium containing 50 μg/ml of ampicillin at 37° C. overnight. From this culture, a plasmid DNA was prepared in accordance with the alkali method ("*Molecular Cloning*", cited above). The plasmid thus obtained was named pYES2aur1.

8-d) Construction of chromosome integration vector

About 0.4 μg of the above-mentioned plasmid pYES2aur1 was digested with XbaI and KonI and electrophoresed on an agarose gel. Then a DNA fragment of about 1.9 kb containing scaur1$^R$ was recovered from the gel and purified by using Suprec-O1.

Similarly, about 0.4 μg of the plasmid vector pUC19 was digested with SspI and PvuII and electrophoresed on an agarose gel. Then a DNA fragment (about 1.8 kb) containing an ampicillin resistant gene and ColE1 origin was recovered from the gel and purified. About 0.1 μg portions of these DNA fragments thus 15 purified were blunt-ended with the use of a DNA blunting kit (manufactured by Takara Shuzo Co., Ltd.). Further, about 0.1 μg portions of these blunted DNA fragments were subjected to a ligation reaction. The ligation reaction was effected by using a DNA ligation kit (manufactured by Takara Shuzo Co.,Ltd.).

Subsequently, the plasmid was integrated into *Escherichia coli* JM109. After incubating, a transformant and a plasmid DNA were prepared. The plasmid thus obtained was named plasmid pAUR1. Next, this plasmid was cleaved with StuI to thereby prepare a chromosome integration vector.

EXAMPLE 9

Construction of Chromosome Integration Vector Containing Aureobasidin Resistant Gene 9-a) Amplification of DNA fragment of scaur1$^R$ having mutation introduced therein by PCR In order to replace the 240th amino acid residue Ala of Aur1$^R$p (F158Y) by Cys, a primer, wherein the codon GCT of Ala had been changed into the codon TGT of Cys, represented by SEQ ID No. 34 in the Sequence Listing was synthesized and purified. By using the plasmid pUscaur1R described in Example 8-a), which carried a HindIII fragment (3.5 kb) containing scaur,R at the HindIII site of pUC119, as a template, was amplified a DNA fragment (about 1.4 kb) which contained a sequence of about 500 bp coding for the amino acid sequence on the C-terminal side of Aur1$^R$p (F158Y, A240C), wherein GCT had been changed into TGT, by the PCR method with the use of the primer represented by SEQ ID No. 34 in the Sequence Listing and a primer M13M4. The PCR was effected in the following manner. To 28 μl of a PCR buffer [capable of giving final concentrations of 10 mM of Tris-HCl (pH 8.3), 50 mM of KCl, 1.5 mM of MgCl$_2$, 0.1 mM of dATP, 0.1 mM of dCTP, 0.1 mM of dTTP and 0.1 mM of dGTP] were added 2.5 U of Ampli Taq DNA polymerase, 100 pmol portions of the primer represented by SEQ ID No. 34 in the Sequence Listing and the primer M13M4, 1 ng of pUscaur1R and distilled water to thereby give 100 μl of a PCR solution. This reaction mixture was then heated successively at 94° C. for 1 minute, at 55° C. for 1.5 minutes and at 72° C. for 1.5 minutes. This cycle was repeated 30 times. Next, the PCR product was cleaved with SalI and SnaI and electrophoresed on an agarose gel. The target DNA fragment of about 1.3 kb was recovered from the gel and purified.

9-b) Construction of plasmid containing DNA coding for Aur1$^R$p (F158Y, A240C)

pUscaur1R was cleaved with SalI and SnaI and electrophoresed on an agarose gel. The target DNA fragment of 5.3 kb was recovered and purified. To this DNA fragment was ligated the DNA fragment of 1.3 kb obtained in Example 9-a). The obtained plasmid, which had a DNA (scaur1$^R$-C) coding for Aur1$^R$p (F158Y, A240C), was named pUscaur1$^R$-C. To effect transformation by integrating it into the chromosome of sake yeast, pUscaur1$^R$-C was linearized by cleaving with StuI prior to use. As a control, pUscaur1R was also linearized with StuI.

9-c) Construction of plasmid containing DNA coding for Aur1$^R$p (A24C)

puscaur1$^S$ was cleaved with SalI and SnaI and electrophoresed on an agarose gel. The target DNA fragment of 5.3 kb was recovered and purified. This DNA fragment was ligated the DNA fragment of 1.3 kb obtained in Example 9-a). The obtained plasmid, which had a DNA coding for Aur1$^R$p (A240C) wherein the 240th residue Ala of Aur1$^S$p had been replaced by Cys, was named pUscaur1A240C, To effect transformation by integrating it into the chromosome of sake yeast, pUscaur1A240C was linearized by cleaving with StuI prior to use.

EXAMPLE 10

Transformation by Using Sake Yeast as Host 10-a) About 10 μg of the linearized vector of the plasmid pAUR1 described in Example 8 was introduced into Sake yeast Kyokai k-701 by the lithium acetate method [*Journal of Bacteriology*, 153, 163 (1983)].

Namely, to Sake yeast Kyokai K-701, which had been suspended in a 0.1 M lithium acetate solution (about 1.3×10$^8$ cells/100 μl of 0.1 M lithium acetate), was added 10 μg of the vector which had been prepared through the linearization of scaur1$^R$ by cleaving with StuI at one position. After treating at 30° C. for 30 minutes and then at 42° C. for 15 minutes, the cells were harvested by centrifugation and pre-incubated in 5 ml of a YPD liquid medium. After pre-incubating in a YPD liquid medium containing 0.4 μg/ml of aureobasidin A, transformants were obtained on a YPD agar medium containing 0.8 μg/ml of aureobasidin A. This transformant was named Sake yeast Kyokai K-701/pAUR1.

This transformant was subcultured over three generations in the absence of aureobasidin A and then the sensitivity to aureobasidin was assayed. As a result, it showed eight times as much aureobasidin resistance (MIC 1.56 μg/ml) as that of the parent strain (i.e., Sake yeast Kyokai K-701), which indicated that the aureobasidin resistance was sustained. Thus it has been confirmed that the aureobasidin resistance introduced on the host chromosome is usable as a selective marker.

10-b) To compare the activities of pUscaur1$^R$-C prepared in Example 9-b), pUscaur1A240C prepared in Example 9-c) and pUscaur1R repared in Example 8-a), 5 μg of the plasmid, which had been linearized with StuI, was introduced into Sake yeast Kyokai K-701 by the lithium acetate method. Namely, to sake yeast, which had been suspended in a 0.1 M lithium acetate solution (pH 7.5) and made competent, were added 5 μg of the plasmid, which had been linearized by cleaving with StuI at one position, and 850 μl of 40% polyethylene glycol/0.1 M lithium acetate. After treating at 30° C. for 30 minutes and then maintaining at 42° C. for 15 minutes, the cells were harvested, pre-incubated in 5 ml of a YPD liquid medium for 1 hour or overnight and then smeared on a YPD agar medium containing aureobasidin A at various concentration. After incubating at 30° C. for 3 to 4 days, transformants having a resistance to aureobasidin A were obtained. As Table 4 shows, the transformant prepared by using the StuI-linearized puscaur1$^R$-C could grow even in the medium containing 5 μg/ml of aureobasidin A. These transformants sustained an aureobasidin A resistance at least 10 times higher than that of the parent strain even after being subcultured over several generations. The transformant obtained by using the linearized puscaur1$^R$-C showed an MIC to aureobasidin A of 20 μg/ml or above. Thus it has been confirmed that the Aur1$^R$p (F158Y, A240C) is usable as an effective selective marker for sake yeast. As Table 4 shows, the StuI-linearized pUscaur1A240C exceeded the StuI-linearized pUscaur1R in the activity of imparting resistance, That is to say, the mutation at the 240th residue Ala resulted in the expression of the activity of imparting a stronger resistance.

TABLE 4

| Plasmid | Pre-incubation time | No. of transformants/μg DNA Aureobasidin A concn. (μg/ml) | | |
|---|---|---|---|---|
| | | 0.5 | 1.0 | 5.0 |
| StuI-linearized pUscaur1R | 1 hr | 0 | 0 | 0 |
| | overnight | 5 | 4 | 0 |
| StuI-linearized pUscaur1R-C | 1 hr | 170 | 73 | 0 |
| | overnight | 2368 | 2024 | 64 |
| StuI-linearized pUscaur1A240C | 1 hr | 18 | 1 | 0 |
| | overnight | 160 | 152 | 0 |
| no plasmid (control) | 1 hr | 0 | 0 | 0 |
| | overnight | 0 | 0 | 0 |

EXAMPLE 11

Transformation by Chromosome Integration Vector Having Aureobasidin Resistant Gene and AARE Gene 11-a) Construction of plasmid containing AARE gene 0.5 μg of the plasmid pAUR1 was cleaved with SphI and electrophoresed on an agarose gel. Then the linearized plasmid pAUR1 was recovered from the gel and purified.

Next, a plasmid pYHA201 was prepared from a yeast BJ2168, which carried a plasmid pYHA201 containing the AARE gene described in Japanese Patent Laid-Open No. 254680/1991 (i.e., *Saccharomyces cerevisiae* BJ2168/pYHA201; FERM P-11570). 0.5 μg of this plasmid pYHA201 was digested with SphI and the DNA fragments (about 3.2 kb) were isolated and purified.

This DNA fragment of about 3.2 kb contained the AARE gene bound to the downstream of the ADHI promotor.

By using each 0.2 μg portions of both the purified SvhI-cleaved DNA fragments, a ligation reaction was effected by using a DNA ligation kit (manufactured by Takara Shuzo Co., Ltd.). Subsequently, the plasmid was integrated into *Escherichia coli* JM109 and incubated to thereby give a transformant and a plasmid DNA. The plasmid thus obtained was named plasmid pAUR1aare, while the transformant thus obtained was named and indicated as *Escherichia coli* JM109/pAUR1aare and has been deposited at National Institute of Bioscience and Human-Technology, Agency of Industrial Science and Technology under the accession number FERM P-14366. 11-b) Expression of AARE in sake yeast By using about 10 μg of the above-mentioned plasmid pAUR1aare, the plasmid pAUR1aare linearized was transformed into Sake yeast Kyokai K-701 in the same manner as the one described in Example 10. Then an aureobasidin resistant transformant was obtained on a YPD agar medium containing 0.4 μg/ml of aureobasidin A.

The transformant thus obtained was named and indicated as *Saccharomyces cerevisiae* K701/pAUR1aare and has been deposited at National Institute of Bioscience and Human-Technology, Agency of Industrial Science and Technology under the accession number FERM P-14379.

Next, this transformant was inoculated into 5 ml of a minimal medium [0.67% of Bacto Yeast Nitrogen Base w/o Amino Acid (manufactured by Difco), 2% of glucose] and incubated at 30° C. for two days and then the cells were harvested by centrifugation.

After discarding the supernatant, the cells were washed with 2 ml of water and harvested again by centrifugation.

Subsequently, the cells were suspended in 700 μl of a 0.2 M sodium phosphate buffer Solution (pH 7.2).

To this suspension were added 400 μl of glass beads (0.40 to 0.60 mm in diameter) and the cells were disrupted by vigorously stirring under ice-cooling.

After centrifuging, the supernatant was recovered and regarded as a extract.

Also, extracts of Sake yeast Kyokai K-701 and Sake yeast Kyokai K-701/pAUR1 obtained in Example 10 were prepared in the same manner.

The acylamino acid releasing enzyme activity of each of the extracts thus obtained was measured by the following method. 0.89 ml of a 0.5% dimethylformamide-0.2 M sodium phosphate buffer solution (pH 7.2) containing 0.020 mM of an amide prepared from N-acetyl-L-methionine and 7-amino-4-methylcoumarin (AMC) was preheated at 37° C. for about 5 minutes. Then 100 μl of the above-mentioned extract was added thereto and the resulting mixture was incubated at 37° C. for 15 minutes. After the completion of the reaction, 10 μl of 10% SDS was added to thereby cease the reaction and the intensity of fluorescence was measured with a fluorophotometer. Namely, the excitation wavelength and the measurement wavelength were set respectively to 380 nm and 440 nm. The amount of the liberated AMC was determined by preparing a standard curve with the use of AMC samples of known concentrations and comparing the obtained data therewith.

100 μl of the extract of S. cerevisiae K701/pAUR1aare had an activity of liberating about 25 pmol of AMC in 15 minutes in the above reaction system.

On the other hand, the extract of Sake yeast Kyokai K-701 having no plasmid and the extract of Sake yeast Kyokai K-701/pAUR1 obtained in Example 10 showed each no AARE activity.

Further, an analysis was effected by the southern ahybridization with the use of the aureobasidin resistant gene as a probe. As a probe in the hybridization, use was made of an scaur1$^R$ fragment (about 1.6 kb) which had been amplified by the PCR method with the use of the plasmid pAUR1 as a template and the primers represented by SEQ ID Nos. 26 and 27 in the Sequence Listing. 100 ng of the fragment thus obtained was labeled with [$^{32}$P]dCTP by using a Bca-BEST™ labeling kit. The genomic DNAs of Sake yeast Kyokai K-701 and Saccharomyces cerevisiae K701/pAUR1aare were cleaved with various restriction enzymes (HPaI having no cleavage site on pAUR1aare, BamHI having two cleavage sites on pAUR1aare), electrophoresed on an agarose gel and transferred onto the hybridization filter.

Figure 14:
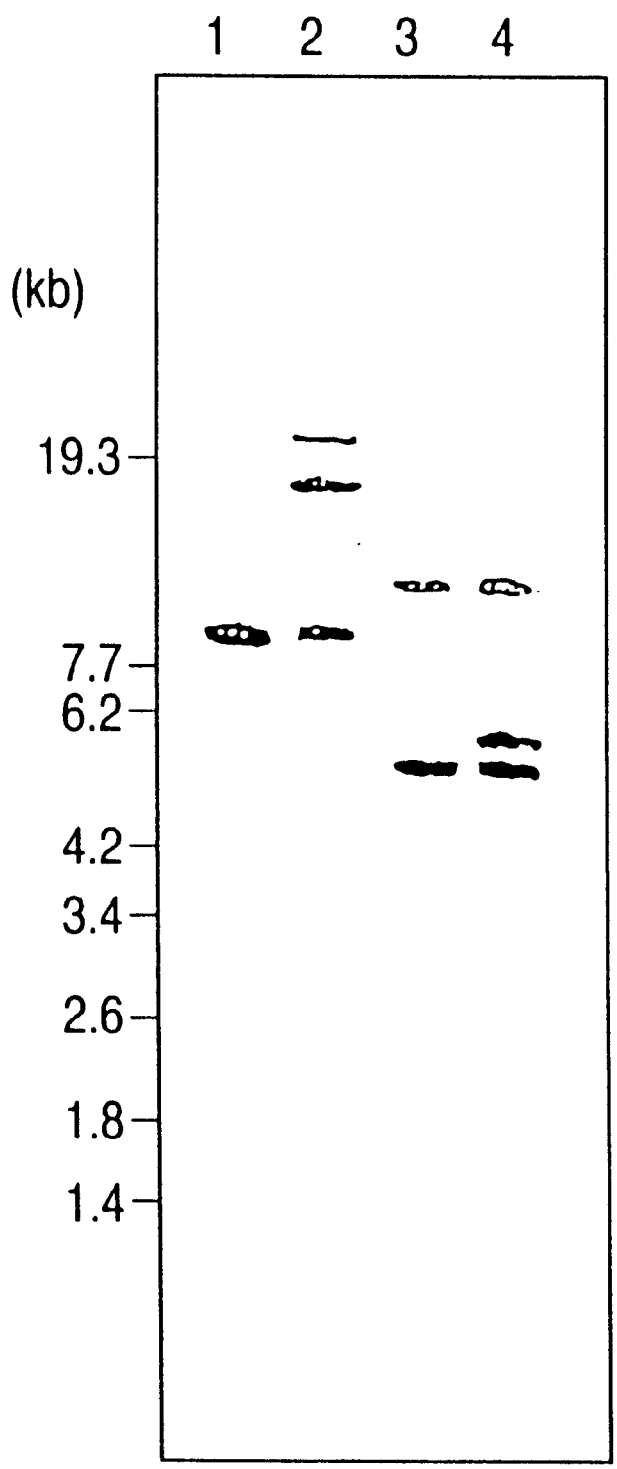
FIG. 14 shows a pattern of the southern hybridization after electrophoresis of the genomic DNA digested by a restriction enzyme.

In FIG. 14, the lanes 1 and 2 show the results obtained by cleaving the genomic DNA of Sake yeast Kyokai K-701 with HpaI (lane 1) or BamHI (lane 3) and subjected to southern hybridization, while the lanes 2 and 4 show the results obtained by cleaving the genomic DNA of Saccharomyces cerevisiae K701/pAUR1aare with HpaI (lane 2) or BamHI (lane 4) and subjected to southern hybridization. Since HpaI had no cleaving site on the plasmid pAUR1aare but cleaved exclusively the genomic DNA, it was proved from the lanes 1 and 2 that the aureobasidin resistant gene had been integrated into one of a pair of chromosomes.

It was confirmed from the lanes 3 and 4 that the aureobasidin resistant gene had been homologously integrated into the aureobasidin sensitive gene on the chromosome of the sake yeast.

These result indicate that genes of the sake yeast were not disrupted by the random integration of the aureobasidin resistant gene.

As described above, by using the chromosome integration vector of the present invention, the resistance could be imparted to an aureobasidin sensitive fungi and, furthermore, a foreign gene could be expressed.

EXAMPLE 12

Construction of Recombinant Plasmid Containing Aureobasidin Resistant Gene 12-a) Construction of pYC vector carrying DNA coding for Aur1$^R$p (F158Y, A240C)

By employing pUscaur1$^R$-C as a template, PCR was effected with the use of primers represented by SEQ ID Nos. 35 and 36 in the Sequence Listing. The PCR product (about 2.2 kb), which contained the DNA coding for the amplified Aur1$^R$p (F158Y, A240C), was cleaved with XhoI and KpnI and blunt-ended with the use of a blunting kit (manufactured by Takara Shuzo Co., Ltd.).

A pYC vector pYEUra3 (manufactured by Clontech Laboratories, Inc.) was cleaved with EcoRI and BamHI and blunt-ended with the use of a blunting kit. Then it was ligated to the blunt-ended PCR product (about 2.2 kb) described above. The plasmid thus obtained was named pYCscaur1$^R$-C. By employing pUscaur1R as a template, PCR was effected in the same manner with the use of primers represented by SEQ ID Nos. 35 and 36 in the Sequence Listing. The PCR product (about 2.2 kb), which contained the DNA coding for the amplified Aur1$^R$p (F158Y), was cleaved with XhoI and KpnI and blunt-ended with the use of a blunting kit (manufactured by Takara Shuzo Co., Ltd.). A pYEUra3 was cleaved with EcoRI and BamHI and blunt-ended with the use of a blunting kit. Then it was ligated to the blunt-ended PCR product (about 2.2 kb) described above. The plasmid thus obtained was named pYCscaur1R.

12-b) Construction of pYE vector carrying DNA coding for Aur1$^R$p (Fl58Y, A240C)

By using pUscaur1$^R$-C as a template, the DNA fragment (about 2.2 kb), which contained the DNA coding for Aur1$^R$p (F158Y, A240C), was amplified by the PCR method with the use of a primer represented by SEQ ID No. 35 in the Sequence Listing and a primer M13M4. The PCR product was cleaved with BamHI and electrophoresed on an agarose gel. Then the target DNA fragment (about 1.8 kb) was recovered from the gel and purified. The plasmid pSCAR1 was cleaved with BamHI and thus a DNA fragment of 11.7 kb, from which a DNA fragment of 2.8 kb containing scaur1$^S$ had been deleted, was obtained. This DNA fragment of 11.7 kb was ligated to the above-mentioned DNA fragment of 1.8 kb containing the DNA coding for Aur1$^R$p (F158Y, A240C). Then a plasmid having the fragment of 1.8 kb inserted thereinto in the desired direction was selected. This plasmid containing the DNA coding for Aur1$^R$p (F158Y, A240C) was named pWscaur1$^R$-C and employed in the transformation of a yeast for laboratory use.

EXAMPLE 13

Transformation with the Use of Yeast as Host 13-a) Transformation of sake yeast by pYCscaur1$^R$-C By using 5 μg of a pYC plasmid pYCscaur1$^R$-C, Sake yeast Kyokai K-701 was transformed by the lithium acetate method described in Example 8-a). As Table 5 shows, the obtained results are similar to those obtained in the cases of the linearized plasmids. These transformants sustained each an aureobasidin A resistance at least 10 times higher than that of the parent strain even after being subcultured over several generations. Thus it has been confirmed that Aur1$^R$p (F158Y, A240C) is usable as an effective selective marker for sake yeast in the transformation by a replication vector.

TABLE 5

| Plasmid | Pre-incubation time | No. of transformants/µg DNA Aureobasidin A concn. (µg/ml) | | | |
|---|---|---|---|---|---|
| | | 0.5 | 1.0 | 2.0 | 5.0 |
| pYCscaur1R | 1 hr | 0 | 0 | 0 | 0 |
| | overnight | 24 | 21 | 0 | 0 |
| pYCscaur1$^R$-C | 1 hr | 386 | 172 | 18 | 1 |
| | overnight | 4824 | 4792 | 1692 | 136 |

13-b) Transformation of laboratory yeast by pWscaur1$^R$-C

By using a monoploid yeast DKD-5D for laboratory use (a, his3, 1-D trp1, leu2-3, 112) as a host, 5 µg of pWscaur1$^R$-C was transformed by the lithium acetate method described in Example 10-a).

For comparison, a transformant was screened on a minimal medium by using an auxotrophic marker contained in the plasmid. As Table 6 shows, it has been confirmed that Aur1$^R$p (F158Y, A240C) is usable as a selective marker which is comparable to the conventional auxotrophic markers in a monoploid yeast.

TABLE 6

| Plasmid | Pre incuba-tion time | No. of transformants/µg DNA Minimal Aureobasidin A concn. (µg/ml) | | | |
|---|---|---|---|---|---|
| | | medium | 0.5 | 1.0 | 5.0 |
| pWscaur1$^R$-C | 1 hr | 192 | 248 | 181 | 58 |
| | overnight | 2500 | 2780 | 2524 | 2044 |

EXAMPLE 14

Transformation by Using *C. albicans* as Host 14-a)

5 µg of a linear plasmid, which had been prepared by cleaving puscaur1$^R$-C with SalI capable of cleaving at one point in the pUC119 region, was transformed into *C. albicans* TIMM0136 by the lithium acetate method. After the completion of the transformation, the cells were incubated in a YPD medium for 1 hour or overnight and then smeared on a YPD agar medium containing aureobasidin A. As Table 7 shows, transformants having the resistance to aureobasidin were obtained by effecting the pre-incubation overnight. These transformants showed each an MIC of 10 µg/ml or above.

TABLE 7

| Plasmid | Pre-incuba-tion time | No. of transformants/µg DNA Aureobasidin A concn. (µg/ml) | |
|---|---|---|---|
| | | 0.25 | 1.0 |
| SalI-linearized pUscaur1$^R$-C | 1 hr | 0 | 0 |
| | overnight | 180 | 0 |

According to the present invention, a novel protein regulating aureobasidin sensitivity and a gene coding for the protein, i.e., a gene regulating aureobasidin sensitivity are provided. These substances are useful in the diagnosis and treatment for diseases caused by organisms having the above-mentioned gene, such as mycoses. The present invention further provides an antisense DNA and an antisense RNA of this gene, a nucleic acid probe being hybridizable with the gene, a process for detecting the gene by using this nucleic acid probe, a process for producing a protein regulating aureobasidin sensitivity by using a transformant having the gene introduced thereinto, an antibody for the protein and a process for detecting the protein by using this antibody. They are also useful in the diagnosis and treatment of diseases including mycoses.

In addition, the present invention provides a chromosome integration vector with the use of a resistance to aureobasidin as a selective marker, which is useful in genetic recombination of fungi (in particular, industrial fungi), a process for producing a transformant having this vector introduced thereinto, and a transformant obtained by this process. They are effectively applicable to, for example the creation of a transformant for producing a useful protein and breeding. The present invention also provides a protein capable of imparting a strong resistance to aureobasidin and a DNA coding for this protein. They imparted a resistance to an organism having an aureobasidin sensitivity and are useful as a selective marker for screening the organism thus acquiring the resistance. They are highly useful particularly in, for example, the genetic engineering breeding of a practically usable yeast and the analysis of genetic information of *C. albicans*. In particular, an aureobasidin resistant gene originating in *S. cerevisiae* is highly useful in the breeding of *S. cerevisiae* and the preparation of a transformant for producing a useful protein, because *S. cerevisiae* is a yeast which is not only widely employed as an industrial yeast but also highly safe in genetic recombination.

What is claimed is:

1. An isolated protein comprising the amino acid sequence according to SEQ ID NO: 8, or, a contiguous fragment thereof, wherein:

(a) said isolated protein and contiguous fragment confer aureobasidin resistance to a cell, and (b) said protein and contiguous fragment have amino acid residue 240, Ala, replaced with another amino acid.

2. The isolated protein according to claim 1, wherein the amino acid 240, Ala, is replaced with Cys.

3. The isolated protein according to claim 26, having the amino acid sequence according to SEQ ID NO: 28 or SEQ ID NO: 29.

4. An isolated protein comprising the amino acid sequence according to SEQ ID NO: 8, or, a contiguous fragment thereof, wherein:

(a) said isolated protein and contiguous fragment confer aureobasidin resistance to a cell, and (b) said protein and contiguous fragment have amino acid substitution at amino acid residue 240 or 158 or both.

* * * * *